(12) United States Patent
Sidhu et al.

(10) Patent No.: US 10,746,743 B2
(45) Date of Patent: Aug. 18, 2020

(54) MOLECULAR DISPLAY SYSTEM

(71) Applicant: The Governing Council of the University of Toronto, Toronto (CA)

(72) Inventors: Sachdev Sidhu, Toronto (CA); Jason Moffat, Toronto (CA); Helena Persson, Lund (SE); Nish Patel, Scarborough (CA); Saravanan Sundararajan, Gaithersburg, MD (US); Amandeep Gakhal, Toronto (CA); Wei Ye, Toronto (CA); Jelena Tomic, Toronto (CA); Megan Elizabeth Mclaughlin, Toronto (CA)

(73) Assignee: The Governing Council of the University of Toronto, Toronto (CA)

( * ) Notice: Subject to any disclaimer, the term of this patent is extended or adjusted under 35 U.S.C. 154(b) by 0 days.

(21) Appl. No.: 15/344,971

(22) Filed: Nov. 7, 2016

(65) Prior Publication Data

US 2017/0184608 A1    Jun. 29, 2017

Related U.S. Application Data

(63) Continuation of application No. 13/629,520, filed on Sep. 27, 2012, now abandoned.

(60) Provisional application No. 61/539,546, filed on Sep. 27, 2011.

(51) Int. Cl.
*C40B 30/04* (2006.01)
*G01N 33/68* (2006.01)
*C12N 15/10* (2006.01)

(52) U.S. Cl.
CPC ..... *G01N 33/6854* (2013.01); *C12N 15/1037* (2013.01); *G01N 33/6857* (2013.01); *C40B 30/04* (2013.01)

(58) Field of Classification Search
None
See application file for complete search history.

(56) References Cited

U.S. PATENT DOCUMENTS

2007/0059755 A1    3/2007    Janssen et al.

OTHER PUBLICATIONS

'T Hoen, P. A. C. et al., "Phage Display Screening Without Repetitious Selection Rounds," Analytical Biochemistry 421: 622-631 (2011).
Adams, G. P. et al., "Monoclonal Antibody Therapy of Cancer," Nat Biotech 23: 1147-1157 (2005).
Berns, K. et al., "A Functional Genetic Approach Identifies the PI3K Pathway as a Major Determinant of Trastuzumab Resistance in Breast Cancer," Cancer Cell 12: 395-402 (2007).
Burton, D. R., "Antibodies, Viruses and Vaccines," Nat Rev Immunol 2: 706-713 (2002).
Carter, P. et al., "Humanization of an Anti-p185HER2 Antibody for Human Cancer Therapy," Proc Natl Acad Sci USA 89: 4285-4289 (1992).
Christian, S. et al., "Nucleolin Expressed at the Cell Surface is a Marker of Endothelial Cells in Angiogenic Blood Vessels," Journal of Cancer Cell Biology 163: 871-878 (2003).

(Continued)

*Primary Examiner* — Christian C Boesen
(74) *Attorney, Agent, or Firm* — Carmela De Luca; Bereskin & Parr LLP

(57) ABSTRACT

There is provided herein a method for identifying and/or recovering at least one genetically encoded affinity reagent specific for a target molecule by screening using molecular display in conjunction with the sequencing of positive and negative selection pools from the screen.

19 Claims, 16 Drawing Sheets

Specification includes a Sequence Listing.

(56) References Cited

OTHER PUBLICATIONS

Cock, P. J. et al., "The Sanger FASTQ File Format for Sequences With Quality Scores, and the Solexa/Illumina FASTQ Variants," Nucleic Acids Res 38: 1767-1771 (2010).
Desiderio, A. et al., "A Semi-synthetic Repertoire of Intrinsically Stable Antibody Fragments Derived from a Single-framework Scaffold," Journal of Mol Biol 310: 603-615 (2001).
Di Niro, R. et al., "Rapid Interactome Profiling by Massive Sequencing," Nucleic Acids Res 38(9): document e110 (2010).
Economopoulos, N. O. et al., "The Generation of Affinity Reagents Using High-throughput Phage Display and Building the Foundations of a Novel High-throughput Intrabody Pipeline," (Master's Thesis). Retrieved from http://hdl.handle.net/1807/30584 (2011).
Eisenhardt, S. U. et al., "Subtractive Single-chain Antibody (scFv) Phage-display: Tailoring Phage-display for High Specificity Against Function-specific Conformations of Cell Membrane Molecules," Nat Protoc 2: 3063-3073 (2007).
Fellouse, F. A. et al., "High-throughput Generation of Synthetic Antibodies from Highly Functional Minimalist Phage-displayed Libraries," J Mol Biol 373: 924-940 (2007).
Fellouse, F. A. et al., "Methods for the Construction of Phage-Displayed Libraries," in Phage Display in Biotechnology and Drug Discovery. Boca Raton: CRC Press (2005).
Ge, X. et al., "Rapid Construction and Characterization of Synthetic Antibody Libraries Without DNA Amplification," Biotechnol Bioeng 106: 347-357 (2010).
Giordano, R. J. et al., "Biopanning and Rapid Analysis of Selective Interactive Ligands," Nat Med 7: 1249-1253 (2001).
Greulich, H. et al., "Oncogenic Transformation by Inhibitor-sensitive and -resistant EGFR mutants, PLoS Med 2: 313 (2005).
Hoet, R. M. et al., "Generation of High-affinity Human Antibodies by Combining Donor-derived and Synthetic Complementarity-determining-region Diversity," Nature Biotechnology 23(3): 344-348 (2005).
Hoogenboom, H. R. et al., "Antibody Phage Display Technology and its Applications," Immunotechnology 4: 1-20 (1998).
Huie, M. A. et al., "Antibodies to Human Fetal Erythroid Cells from a Nonimmune Phage Antibody Library," Proc Natl Acad Sci USA 98: 2682-2687 (2001).
Li, Y. M. et al., "Upregulation of CXCR4 is Essential for HER2-mediated Tumor Metastasis," Cancer Cell 6: 459-469 (2004).
Lonza Technical Reference Guide [online] Guidelines for Generation of Stable Cell Lines 2009 [retrieved on Oct. 23, 2014]. Retrieved from the Internet: <http://bio.lonza.com/uploads/tx_mwaxmarketingmaterial/Lonza_TechREF_Generation_of_Stable_Cell_Lines_low_res.pdf>, pp. 1-8.
Lundstrom, K., "Structural Genomics and Drug Discovery," J Cell Mol Med 11: 224-238 (2007).
Matthews, D. J. et al., "Substrate Phage: Selection of Protease Substrates by Monovalent Phage Display," Science 260: 1113-1117 (1993).
Nahta, R. et al., "HER-2-targeted Therapy: Lessons Learned and Future Directions," Clin Cancer Res 9: 5078-5084 (2003).
Noronha, E. J. et al., "Limited Diversity of Human scFv Fragments Isolated by Panning a Synthetic Phage-display scFv Library with Cultured Human Melanoma Cells," J Immunol 161: 2968-2976 (1998).
Osbourn, J. K. et al., "Directed Selection of MIP-1 Alpha Neutralizing CCR5 Antibodies from a Phage Display Human Antibody Library," Nat Biotechnol 16: 778-781 (1998).
Osbourn, J. K. et al., "Pathfinder Selection: In Situ Isolation of Novel Antibodies," Immunotechnology 3: 293-302 (1998).
Overington, J. P. et al., "How Many Drug Targets Are There?" Nat Rev Drug Discov 5: 993-996 (2006).
Phage Display Technology Review [online] Phage Display 2010 [retrieved on Oct. 24, 2017]. Retrieved from the Internet: <URL: http://phagedisplay.net>, pp. 1-3.
Ravn, U. et al., "By-passing In Vitro Screening—Next Generation Sequencing Technologies Applied to Antibody Display and In Silico Candidate Selection," Nuc Acids Res 38(21): 1-11 (2010).
Reddy, S. T. et al., "Monoclonal Antibodies Isolated Without Screening by Analyzing the Variable-gene Repertoire of Plasma Cells," Nat Biotechnol 28: 965-969 (2010).
Ridgway, J. B. et al., "Identification of a Human Anti-CD55 Single-chain Fv by Subtractive Panning of a Phage Library Using Tumor and Nontumor Cell Lines," Cancer Res 59: 2718-2723 (1999).
Ross, J. S. et al., "The HER-2/neu Oncogene in Breast Cancer: Prognostic Factor, Predictive Factor, and Target for Therapy," Oncologist 3: 237-252 (1998).
Rubin, I. et al., "The Basic Biology of HER2," Ann Oncol 12 Suppl 1: S3-8 (2001).
Sancak, Y. et al., "The Rag GTPases Bind Raptor and Mediate Amino Acid Signaling to mTORC1," Science 320: 1496-1501 (2008).
Shadidi, M. et al., "An Anti-leukemic Single Chain Fv Antibody Selected from a Synthetic Human Phage Antibody Library," Biochemical and Biophysical Research Comm 280: 548-552 (2001).
Sidhu, S. S. et al., "Synthetic Therapeutic Antibodies," Nature Chem Biol 2: 682-688 (2006).
Slamon, D. J. et al., "Human Breast Cancer: Correlation of Relapse and Survival and Amplification of the HER-2/neu Oncogene," Science 235: 177-182 (1987).
Slamon, D. J. et al., "Studies of the HER-2/ne Proto-oncogene in Human Breast and Ovarian Cancer," Science 244: 707-712 (1989).
Tonikian, R. et al., "Identifying Specificity Profiles for Peptide Recognition Modules from Phage-displayed Peptide Libraries," Nat Protoc 2: 1368-1386 (2007).
Van Den Beucken, T. et al., "Affinity Maturation of Fab Antibody Fragments by Fluorescent-activated Cell Sorting of Yeast-displayed Libraries," FEBS Letters 546:288-294 (2003).
Van Ewijk, W. et al., "Subtractive Isolation of Phage-displayed Single-chain Antibodies to Thymic Stromal Cells by Using Intact Thymic Fragments," Proc Natl Acad Sci USA 94: 3903-3908 (1997).
Vodnik, M. et al., "Phage Display: Selecting Straws Instead of a Needle from a Haystack," Molecules 16: 790-817 (published online Jan. 19, 2011).
Vogel, C. L. et al., "Efficacy and Safety of Trastuzumab as a Single Agent in First-line Treatment of HER2-overexpressing Metastatic Breast Cancer," J Clin Oncol 20: 719-726 (2002).
Weiner, L. M. et al., "Monoclonal Antibodies: Versatile Platforms for Cancer Immunotherapy," Nat Rev Immunol 10: 317-327 (2010).
Williams, B. R. et al., "Polyclonal Anti-colorectal Cancer Fab Phage Display Library Selected in One Round Using Density Gradient Centrifugation to Separate Antigen-bound and Free Phage," Immunol Lett 81: 141-148 (2002).
Yarden, Y. et al., "Untangling the ErbB Signaling Network," Nat Rev Mol Cell Biol 2: 127-137 (2001).
Zhang, H. et al., "Phenotype-information-phenotype Cycle for Deconvolution of Combinatorial Antibody Libraries Selected Against Complex Systems," Proc Natl Acad Sci USA 108(33): 13456-13461(2011).
Zhou, B. P. et al., "Dysregulation of Cellular Signaling by HER2/neu in Breast Cancer," Semin Oncol 30: 38-48 (2003).

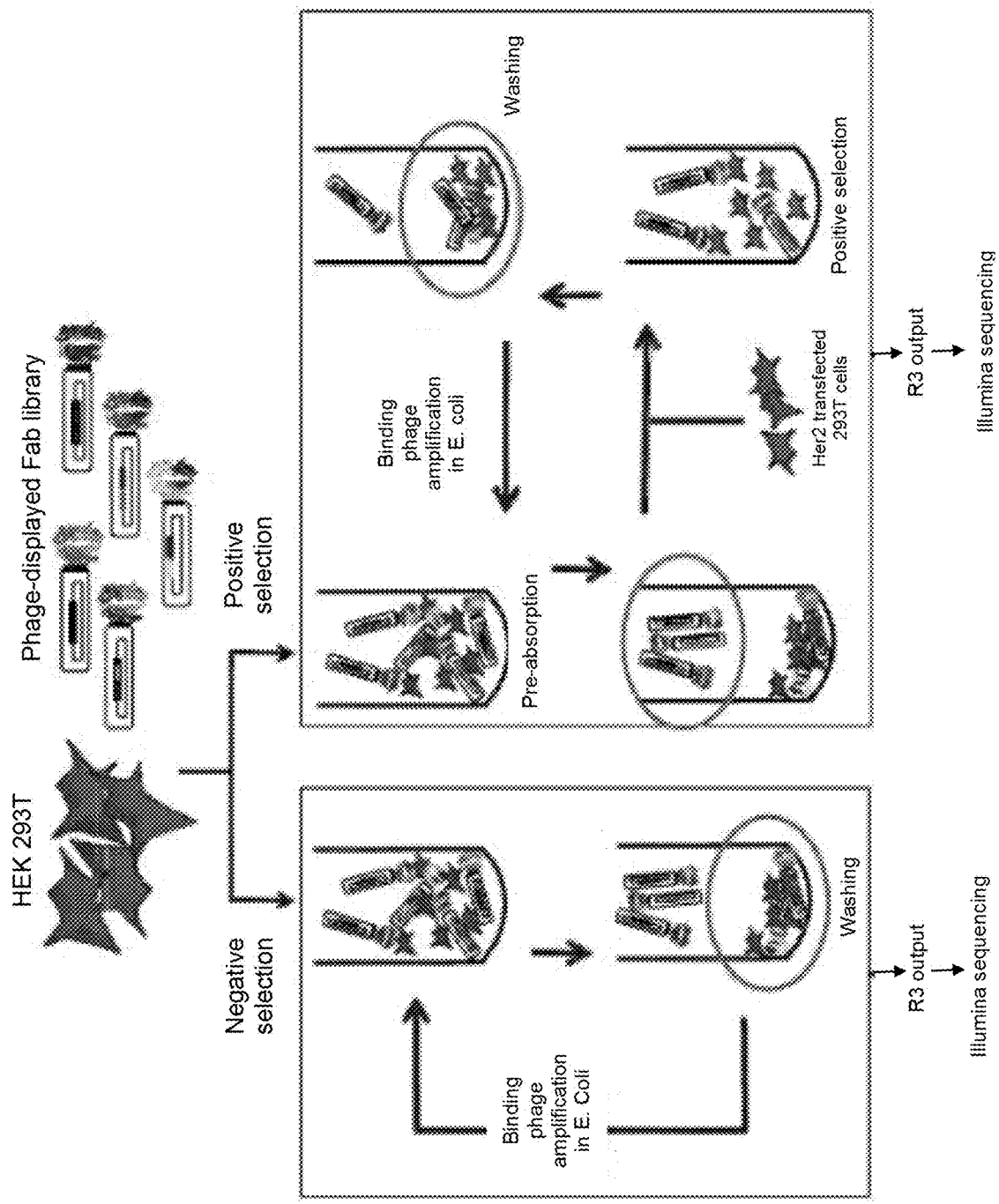

dsDNA pool isolated binding clone

PCR
Ligate
Dpn1 digest

FIGURE 2

| Clone | Counts in Illumina pools | | | CDR sequences | | | |
|---|---|---|---|---|---|---|---|
| | Positive | % of total | Negative | L3 | H1 | H2 | H3 |
| WY574B | 8136 | 2.95 | 0 | QQWH--YAFIT (SEQ ID NO: 17) | GFNLYSSSM (SEQ ID NO: 18) | YISFYGYTY (SEQ ID NO: 19) | ARAVHWY----GYVSGFDY (SEQ ID NO: 20) |
| WY574E | 3290 | 1.19 | 0 | QQGWS--AYLIT (SEQ ID NO: 21) | GFNISYSSI (SEQ ID NO: 22) | SIYSSYGYTS (SEQ ID NO: 23) | ARGWVPAY------PSYGLDY (SEQ ID NO: 24) |
| WY574F | 2060 | 0.75 | 0 | AASSY---SLIT (SEQ ID NO: 25) | GFNLYSYYY (SEQ ID NO: 26) | SIYPSYGYTS (SEQ ID NO: 27) | ARWGSSVYAWSPASWSPFCGMDY (SEQ ID NO: 28) |
| WY677C | 1605 | 0.65 | 0 | QQSSF---WPIT (SEQ ID NO: 29) | GFNISSSYM (SEQ ID NO: 30) | SIYPSYGYTS (SEQ ID NO: 31) | ARSYYWWGF----WSGYSGMDY (SEQ ID NO: 32) |
| WY677D | 677 | 0.25 | 0 | QQSWY---SLIT (SEQ ID NO: 33) | GFRISSSSM (SEQ ID NO: 34) | SIYSSYSSTY (SEQ ID NO: 35) | ARPHPYIPYYS-YWGFYYSGLDY (SEQ ID NO: 36) |

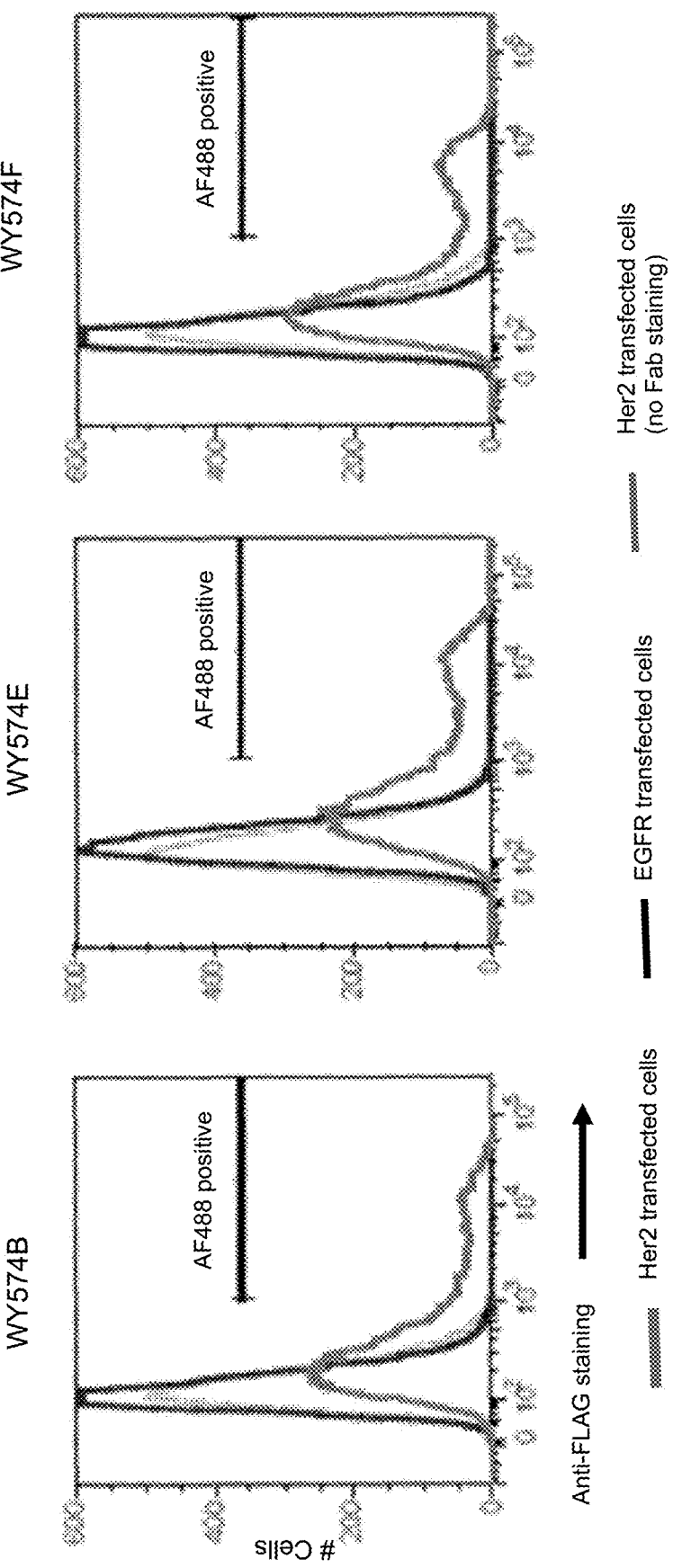

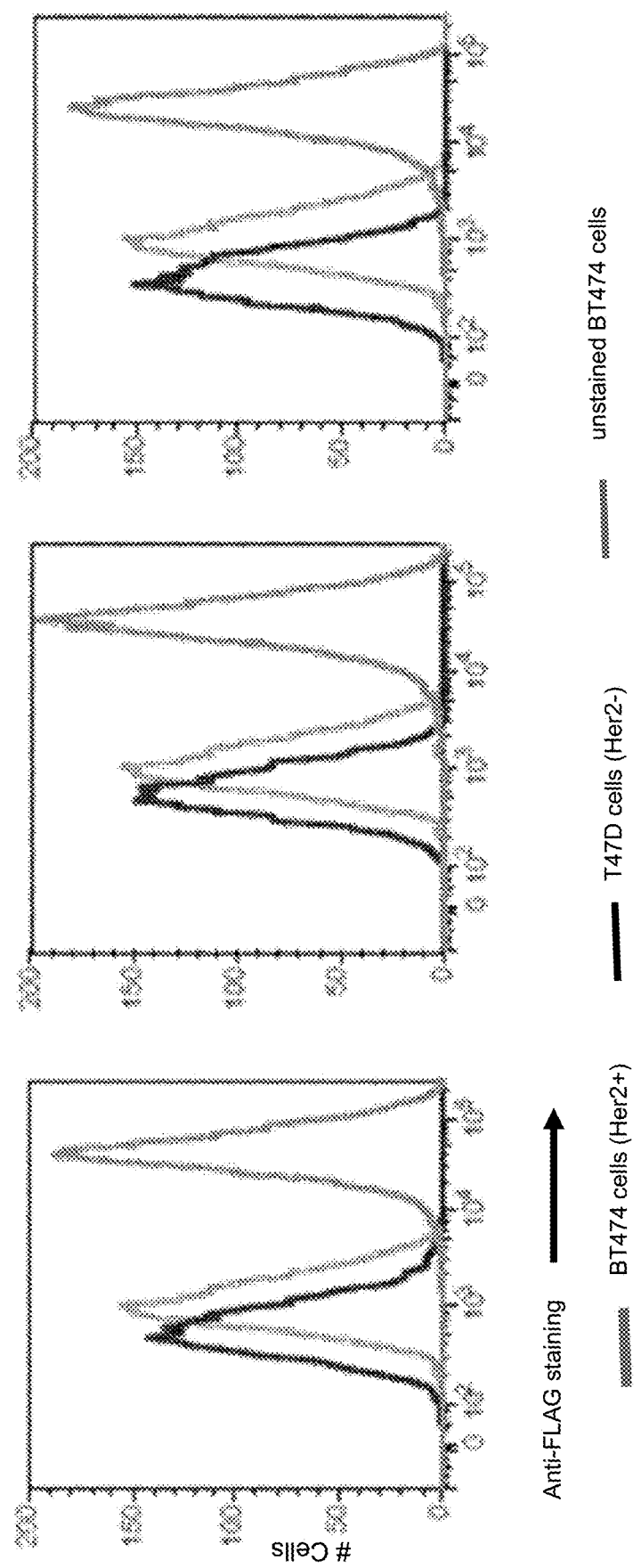

FIGURE 5
Top 100 Illumina sequence results from the positive selection pool

| Sample Number | SEQ ID NO: | CDR H3 sequence | Positive pool Counts | % of total | Negative pool Counts | % of total | Naive pool Counts | % of total |
|---|---|---|---|---|---|---|---|---|
| 1 | 37 | YYWSYYSGGGGFDY | 41262 | 14.94 | 0 | 0.00 | 0 | 0.00 |
| 2 | 38 | NRMDY | 28045 | 10.16 | 179 | 0.08 | 1070 | 0.16 |
| 3 | 39 | YAYSVAGLDY | 9520 | 3.45 | 0 | 0.00 | 0 | 0.00 |
| 4 | 40 | AVVHYWYGYVGGFDY | 8136 | 2.95 | 0 | 0.00 | 0 | 0.00 |
| 5 | 41 | FGWYGLDY | 3810 | 1.38 | 0 | 0.00 | 0 | 0.00 |
| 6 | 42 | GWVPAYPSYGLDY | 3290 | 1.19 | 0 | 0.00 | 0 | 0.00 |
| 7 | 43 | YYWGWFYVSRYSSGASFDY | 2965 | 1.07 | 0 | 0.00 | 0 | 0.00 |
| 8 | 44 | HSAYYRGIDY | 2849 | 1.03 | 0 | 0.00 | 0 | 0.00 |
| 9 | 45 | YYWSYYGYAMDY | 2812 | 1.02 | 0 | 0.00 | 0 | 0.00 |
| 10 | 46 | GYYYPALDY | 2670 | 0.97 | 0 | 0.00 | 0 | 0.00 |
| 11 | 47 | SGMDY | 2685 | 0.97 | 373 | 0.17 | 1634 | 0.24 |
| 12 | 48 | WGSSVYANSPASWSFPFDY | 2060 | 0.75 | 0 | 0.00 | 0 | 0.00 |
| 13 | 49 | YVRGSERDYYGNAMDY | 1919 | 0.69 | 5344 | 2.40 | 12600 | 1.83 |
| 14 | 50 | SYYWWGPWGSYSGMDY | 1805 | 0.65 | 0 | 0.00 | 0 | 0.00 |
| 15 | 51 | YGYWWYWYAFDY | 1593 | 0.58 | 0 | 0.00 | 0 | 0.00 |
| 16 | 52 | GSVYHFPASYYWGWSYGDY | 1334 | 0.48 | 0 | 0.00 | 0 | 0.00 |
| 17 | 53 | AYGMDY | 1027 | 0.37 | 48 | 0.02 | 266 | 0.04 |
| 18 | 54 | YYYFGLDY | 1012 | 0.37 | 61 | 0.03 | 10 | 0.00 |
| 19 | 55 | GWWYGRDY | 989 | 0.36 | 0 | 0.00 | 11 | 0.00 |
| 20 | 56 | YAFDY | 900 | 0.33 | 69 | 0.03 | 282 | 0.04 |
| 21 | 57 | GYWGSFWRAGGDY | 887 | 0.32 | 0 | 0.00 | 0 | 0.00 |
| 22 | 58 | VHSWYGSYGFDY | 811 | 0.29 | 0 | 0.00 | 0 | 0.00 |
| 23 | 59 | VAWYGLDY | 778 | 0.28 | 0 | 0.00 | 2 | 0.00 |
| 24 | 60 | WGYYGLDY | 755 | 0.27 | 0 | 0.00 | 0 | 0.00 |
| 25 | 61 | VSAYYYWGFDY | 748 | 0.27 | 0 | 0.00 | 0 | 0.00 |
| 26 | 62 | PHPYIPYYSYWGPYYSGDY | 677 | 0.25 | 0 | 0.00 | 0 | 0.00 |
| 27 | 63 | VWPSSASYVGFDY | 663 | 0.24 | 0 | 0.00 | 0 | 0.00 |
| 28 | 64 | YASYWGAFDY | 644 | 0.23 | 0 | 0.00 | 0 | 0.00 |
| 29 | 65 | YYWYWGLDY | 616 | 0.22 | 0 | 0.00 | 0 | 0.00 |
| 30 | 66 | FGYYGLDY | 613 | 0.22 | 1 | 0.00 | 1 | 0.00 |
| 31 | 67 | HSYYGYALDY | 612 | 0.22 | 0 | 0.00 | 0 | 0.00 |
| 32 | 68 | GYSYGYSYYSWSSYGAMDY | 610 | 0.22 | 0 | 0.00 | 0 | 0.00 |
| 33 | 69 | AYSYAYGLDY | 557 | 0.20 | 0 | 0.00 | 0 | 0.00 |
| 34 | 70 | ASARYGPNAFDY | 537 | 0.19 | 0 | 0.00 | 0 | 0.00 |
| 35 | 71 | GSSWSFYWYRGGIDY | 518 | 0.19 | 0 | 0.00 | 0 | 0.00 |
| 36 | 72 | GPWWGGYGLDY | 480 | 0.17 | 196 | 0.09 | 0 | 0.00 |
| 37 | 73 | SWARGYAMDY | 462 | 0.17 | 0 | 0.00 | 0 | 0.00 |
| 38 | 74 | SWAVYPSASWGGFDY | 435 | 0.16 | 0 | 0.00 | 0 | 0.00 |
| 39 | 75 | YGPGWSYYGYWGYAAPADY | 413 | 0.15 | 0 | 0.00 | 0 | 0.00 |
| 40 | 76 | YGGSSYWAYYSALDY | 406 | 0.15 | 0 | 0.00 | 0 | 0.00 |
| 41 | 77 | SSSGSGVHGLDY | 397 | 0.14 | 0 | 0.00 | 0 | 0.00 |
| 42 | 78 | YSGRSALDY | 396 | 0.14 | 0 | 0.00 | 0 | 0.00 |
| 43 | 79 | HSAYYSYALDY | 390 | 0.14 | 0 | 0.00 | 0 | 0.00 |
| 44 | 80 | SYGVWNYASSSAAAGLDY | 371 | 0.13 | 141 | 0.06 | 0 | 0.00 |
| 45 | 81 | WSYYGRDY | 370 | 0.13 | 0 | 0.00 | 3 | 0.00 |
| 46 | 82 | YYGRALDY | 337 | 0.12 | 1 | 0.00 | 5 | 0.00 |

FIGURE 5, cont'd

| Sample Number | SEQ ID NO: | CDR H3 sequence | Positive pool | | Negative pool | | Naive pool | |
|---|---|---|---|---|---|---|---|---|
| | | | Counts | % of total | Counts | % of total | Counts | % of total |
| 47 | 83 | GSSYSGYYNSSSSSGLDY | 329 | 0.12 | 0 | 0.00 | 0 | 0.00 |
| 48 | 84 | AGIDY | 321 | 0.12 | 61 | 0.03 | 236 | 0.03 |
| 49 | 85 | WAFDY | 320 | 0.12 | 30 | 0.01 | 169 | 0.02 |
| 50 | 86 | SSWYSPGYGASYGLDY | 318 | 0.12 | 0 | 0.00 | 0 | 0.00 |
| 51 | 87 | YGGGGYWAYVSAFDY | 308 | 0.11 | 0 | 0.00 | 0 | 0.00 |
| 52 | 88 | YWYYGYYAFDY | 306 | 0.11 | 0 | 0.00 | 0 | 0.00 |
| 53 | 89 | PGYVGVGFDY | 304 | 0.11 | 0 | 0.00 | 0 | 0.00 |
| 54 | 90 | SSPYYGLDY | 302 | 0.11 | 0 | 0.00 | 0 | 0.00 |
| 55 | 91 | HVASSFNYSNSYGIDY | 301 | 0.11 | 0 | 0.00 | 0 | 0.00 |
| 56 | 92 | SGASGFDY | 299 | 0.11 | 0 | 0.00 | 1 | 0.00 |
| 57 | 93 | WALDY | 280 | 0.11 | 112 | 0.05 | 583 | 0.08 |
| 58 | 94 | WSGGYYRSMGGMDY | 283 | 0.10 | 0 | 0.00 | 0 | 0.00 |
| 59 | 95 | VSAASSVGFDY | 280 | 0.10 | 0 | 0.00 | 0 | 0.00 |
| 60 | 96 | SYGHYYYGSNNNYYGADY | 279 | 0.10 | 0 | 0.00 | 0 | 0.00 |
| 61 | 97 | HSPTHYSPYYGNGAYADY | 264 | 0.10 | 0 | 0.00 | 0 | 0.00 |
| 62 | 98 | YSSHFAAYYPNSVEALDY | 268 | 0.09 | 0 | 0.00 | 0 | 0.00 |
| 63 | 99 | WYHRAMDY | 249 | 0.09 | 0 | 0.00 | 1 | 0.00 |
| 64 | 100 | VYNNVGMDY | 247 | 0.09 | 0 | 0.00 | 0 | 0.00 |
| 65 | 101 | WYYGSYYGAYXLDY | 245 | 0.09 | 0 | 0.00 | 0 | 0.00 |
| 66 | 102 | GNSNSGLDY | 240 | 0.09 | 0 | 0.00 | 1 | 0.00 |
| 67 | 103 | YSRVWSSHSRANEALDY | 238 | 0.09 | 0 | 0.00 | 0 | 0.00 |
| 68 | 104 | YGRGFDY | 233 | 0.08 | 0 | 0.00 | 8 | 0.00 |
| 69 | 105 | GAHMYGIDY | 228 | 0.08 | 0 | 0.00 | 0 | 0.00 |
| 70 | 106 | VYGRANDY | 223 | 0.08 | 4 | 0.00 | 4 | 0.00 |
| 71 | 107 | VGLDY | 222 | 0.08 | 53 | 0.02 | 272 | 0.04 |
| 72 | 108 | YAAYYSYALDY | 219 | 0.08 | 0 | 0.00 | 0 | 0.00 |
| 73 | 109 | SPYNYYNNWNSAGFDY | 219 | 0.08 | 0 | 0.00 | 0 | 0.00 |
| 74 | 110 | APWSGSSAFDY | 214 | 0.08 | 0 | 0.00 | 0 | 0.00 |
| 75 | 111 | VAAYWVANDY | 212 | 0.08 | 0 | 0.00 | 0 | 0.00 |
| 76 | 112 | YSAGGYYYGFDY | 211 | 0.08 | 0 | 0.00 | 0 | 0.00 |
| 77 | 113 | SYSNYFAMDY | 207 | 0.07 | 0 | 0.00 | 0 | 0.00 |
| 78 | 114 | ANVSALDY | 203 | 0.07 | 0 | 0.00 | 0 | 0.00 |
| 79 | 115 | GHHVVPSGFFNSAIDY | 200 | 0.07 | 0 | 0.00 | 0 | 0.00 |
| 80 | 116 | GSSYSMDY | 196 | 0.07 | 0 | 0.00 | 0 | 0.00 |
| 81 | 117 | FPAYNSNAFDY | 196 | 0.07 | 0 | 0.00 | 0 | 0.00 |
| 82 | 118 | GAPSCYHASYAMDY | 194 | 0.07 | 0 | 0.00 | 0 | 0.00 |
| 83 | 119 | WSYYSGSVYASSNSWSNDY | 194 | 0.07 | 0 | 0.00 | 0 | 0.00 |
| 84 | 120 | YVGNGVSSYNSSYVGASY | 193 | 0.07 | 0 | 0.00 | 0 | 0.00 |
| 85 | 121 | YAMDY | 191 | 0.07 | 455 | 0.20 | 2694 | 0.39 |
| 86 | 122 | PGNSYELDY | 191 | 0.07 | 3 | 0.00 | 0 | 0.00 |
| 87 | 123 | HGIDY | 188 | 0.07 | 35 | 0.02 | 165 | 0.02 |
| 88 | 124 | WYGYYHAYSAMYYSSAGNY | 184 | 0.07 | 0 | 0.00 | 0 | 0.00 |
| 89 | 125 | SGGYAYGNDY | 182 | 0.07 | 0 | 0.00 | 0 | 0.00 |
| 90 | 126 | YSNGYYGIDY | 181 | 0.07 | 3 | 0.00 | 0 | 0.00 |
| 91 | 127 | APYNGYGYYSNAYGYGVSY | 178 | 0.06 | 0 | 0.00 | 0 | 0.00 |
| 92 | 128 | VNSYGRGFDY | 177 | 0.06 | 0 | 0.00 | 0 | 0.00 |
| 93 | 129 | YSSGGYNAYVSSLDY | 175 | 0.06 | 0 | 0.00 | 0 | 0.00 |

FIGURE 5, cont'd

| Sample Number | SEQ ID NO: | CDR H3 sequence | Positive pool | | Negative pool | | Naive pool | |
|---|---|---|---|---|---|---|---|---|
| | | | Counts | % of total | Counts | % of total | Counts | % of total |
| 94 | 130 | YWTGSWSSAMDY | 174 | 0.06 | 14 | 0.01 | 0 | 0.00 |
| 95 | 131 | VRGVGLDY | 171 | 0.06 | 0 | 0.00 | 0 | 0.00 |
| 96 | 132 | YGLDY | 171 | 0.06 | 421 | 0.19 | 1709 | 0.35 |
| 97 | 133 | AYPWGKSGWYSHAYVFDY | 169 | 0.06 | 0 | 0.00 | 0 | 0.00 |
| 98 | 134 | GYGRAWSPAFDY | 163 | 0.06 | 0 | 0.00 | 0 | 0.00 |
| 99 | 135 | SAWGKVFPYSYASSMDY | 154 | 0.06 | 0 | 0.00 | 0 | 0.00 |
| 100 | 136 | YSYSASAWTGAWDY | 152 | 0.06 | 0 | 0.00 | 0 | 0.00 |

FIGURE 9

| Row # | Target Receptor | Cell line | Positive Selection | Negative Selection | Library (F: Fab; G: scFv) | Rescue Strategy 1. Clonal ELISA 2. cdr3 PCR 3. cdrL3: cdrH3 PCR | R&D positive Rank | CDR L3 | SEQ ID NO: | CDR H3 | SEQ ID NO: |
|---|---|---|---|---|---|---|---|---|---|---|---|
| 1 | CD133 | 293 | Antigen+ | Antigen- | G | 3 | 6 | GVWSLI | 137 | HAHSGYGRTAVYGI | 138 |
| 2 | CD133 | 293 | Antigen+ | Antigen- | G | 3 | 28 | SYXGWPLF | 139 | HAHSGYGRTAVYGI | 140 |
| 3 | CD133 | 293 | Antigen+ | Antigen- | G | 3 | 30 | GVWSLI | 141 | HAHSGYGRTAVYGI | 142 |
| 4 | CD133 | 293 | Antigen+ | Antigen- | G | 3 | 31 | GVWSLI | 143 | YHYYXWPHSGXGSF | 144 |
| 5 | CD133 | 293 | Antigen+ | Antigen- | G | 3 | 38 | AYPXLI | 145 | FXYFSYSAMSL | 146 |
| 6 | CD133 | 293 | Antigen+ | Antigen- | G | 3 | 40 | GVWSLI | 147 | HVHSGYGRTAVYGI | 148 |
| 7 | CD133 | 293 | Antigen+ | Antigen- | G | 3 | 47 | SYALI | 149 | HAHSGYGRTAVYGI | 150 |
| 8 | CD133 | 293 | Antigen+ | Antigen- | G | 3 | 51 | GVWSLI | 151 | HAPSGXGRTAVYGI | 152 |
| 9 | CD133 | 293 | Antigen+ | Antigen- | G | 3 | 53 | GVWSLI | 153 | HAHSYGRTAVYGI | 154 |
| 10 | CD133 | 293 | Antigen+ | Antigen- | G | 3 | 94 | GVWSLI | 155 | HAHSGYGRTAVYGI | 156 |
| 11 | CD133 | 293 | Antigen+ | Antigen- | G | 3 | 126 | GVWSLI | 157 | XWHYYSYSLL | 158 |
| 12 | CD133 | 293 | Antigen+ | Antigen- | G | 3 | 322 | YGSYSSLI | 159 | SYYAAWDL | 160 |
| 13 | ErbB3 | 293F | Antigen+ | Antigen- | G | 3 | 12 | SPYGLF | 161 | GXGYFXGM | 162 |
| 14 | ErbB3 | 293F | Antigen+ | Antigen- | G | 3 | 13 | PYWLM | 163 | WSHYYGAM | 164 |
| 15 | ErbB3 | 293F | Antigen+ | Antigen- | G | 3 | 19 | SYRALI | 165 | CGWYWHYYGMGMGLL | 166 |
| 16 | ErbB3 | 293F | Antigen+ | Antigen- | G | 3 | 20 | YGYPF | 167 | GYHSDM | 168 |
| 17 | ErbB3 | 293F | Antigen+ | Antigen- | G | 3 | 28 | YSYYHPWPI | 169 | FXFXFVSGPSLL | 170 |
| 18 | ErbB3 | 293F | Antigen+ | Antigen- | G | 3 | 31 | YHYYSSLF | 171 | YYWHGXWMWVGXA DM | 172 |
| 19 | ErbB3 | 293F | Antigen+ | Antigen- | G | 3 | 35 | SSYSLI | 173 | WSYSSYAPLAL | 174 |
| 20 | ErbB3 | 293F | Antigen+ | Antigen- | G | 3 | 42 | YYYSSPI | 175 | SHYYGYWGHYYGM | 176 |
| 21 | Fzd7 | 293F | Antigen+ | Antigen- | P | 1 | 2 | XGSYPI | 177 | GPGYHYYSYYSSSW DM | 178 |
| 22 | Fzd7 | 293F | Antigen+ | Antigen- | F | 1 | 4 | WGSYSSLI | 179 | GSYYWWYPGM | 180 |
| 23 | Fzd7 | 293F | Antigen+ | Antigen- | F | 2 | 9 | YWYYAYPI | 181 | YGGYYPGMWAL | 182 |
| 24 | ROR1 | 293F | Antigen+ | Antigen- | F | 1 | 1 | YGYYPI | 183 | GAL | 184 |
| 25 | ROR1 | 293F | Antigen+ | Antigen- | F | 1 | 3 | YAYYPI | 185 | GAL | 186 |
| 26 | ROR1 | 293F | Antigen+ | Antigen- | F | 3 | 4 | SYSYAPI | 187 | GAL | 188 |

FIGURE 9, cont'd

| Row # | Target receptor | Cell line | Positive selection | Negative selection | Library (F + Rabbit diverse) | Rescue Strategy 1. Clonal ELISA 2. cdrh3 PCR 3. cdrh1 cdrh3 PCR | BRD positive + Rank | CDRL3 | SEQ ID NO: | CDRH3 | SEQ ID NO: |
|---|---|---|---|---|---|---|---|---|---|---|---|
| 27 | ROR2 | 293T | Antigens+ | Antigens- | F | 1 | 1 | NGTFI | 189 | YDAGGYNNAY | 190 |
| 28 | ROR2 | 293T | Antigens+ | Antigens- | R | 1 | 5 | NGVFI | 191 | DRAGGGDWAP | 192 |
| 29 | ROR2 | 293T | Antigens+ | Antigens- | R | 3 | 30 | YPNIGLF | 193 | YDAGGYNNAY | 194 |
| 30 | ROR2 | 293T | Antigens+ | Antigens- | R | 3 | 78 | YVNIGLF | 195 | GNGYFGLL | 196 |
| 31 | ROR2 | 293T | Antigens+ | Antigens- | R | 3 | 50 | BNGSGVHLI | 197 | SYOL | 198 |
| 32 | ROR2 | 293T | Antigens+ | Antigens- | R | 4 | 10% | ATFFI | 199 | YANGM | 200 |
| 33 | exon16 deleted ErbB2 | 293T | | wt Antigens | R | 3 | 1 | YPGYAGPF | 201 | GGDGAL | 202 |
| 34 | exon16 deleted ErbB2 | 293T | wt Antigens | wt Antigens | F | 1 | 2 | TSALI | 203 | GGGTYGTGP | 204 |
| 35 | exon16 deleted ErbB2 | 293T | wt Antigens | wt Antigens | F | 1 | 5 | TWGPIX | 205 | GYGI | 206 |
| 36 | ITGA11 | CHO | Antigens+ | ITGA2 | F | 1 | 1 | YAARLI | 207 | SAN | 208 |
| 37 | ITGA11 | CHO | Antigens+ | ITGA2 | F | 1 | 3 | RNGSLI | 209 | SAN | 210 |
| 38 | ITGA11 | CHO | Antigens+ | ITGA3 | F | 1 | 12 | BGYELI | 211 | YNTAY | 212 |
| 39 | ITGA11 | C2C12 | Antigens+ | ITGA2 | R | 1 | 50 | YERLI | 213 | YGARFGM | 214 |
| 40 | O-glcNAc modification | MCF7 | Antigens+ with GUP | without GUP | F | 1 | 1 | DYGSBS | 215 | GAAEFTGGRM | 216 |
| 41 | O-glcNAc modification | MCF7 | with GUP | without GUP | R | 1 | 3 | GSRLI | 217 | YGYGL | 218 |
| 42 | O-glcNAc modification | MCF7 | with GUP | without GUP | R | 1 | 4 | | 219 | GGGGAAASGM | 220 |
| 43 | O-glcNAc modification | MCF7 | with GUP | without GUP | R | 1 | 7 | YYGLF | 221 | YHRGYYAGM | 222 |

| Row | Target Receptor | B4O positive Raw counts | Percentage | B3O positive Raw counts | Percentage | B4O negative Raw counts | Percentage | B4O/B3O Raw counts | Enrichment Percentage | Validated For Cell Binding | Aliases |
|---|---|---|---|---|---|---|---|---|---|---|---|
| 30 | ROR2 | 1578 | 0.07% | 20989 | 0.82% | 0 | 0% | 0.08 | 0.08 | ELISA | SD100-1 |
| 31 | RORI | 1038 | 0.05% | 12285 | 0.46% | 0 | 0% | 0.08 | 0.10 | ELISA | SD100-T4 |
| 32 | RORI | 608 | 0.03% | 24843 | 0.96% | 0 | 0% | 0.02 | 0.03 | ELISA | SD100-T5 |
| 33 | ssemi deleted ErbB2 | 895320 | 37.95% | 126265 | 7.05% | 513426 | 27.72% | 6.65 | 3.96 | | C64 ED |
| 34 | ssemi deleted ErbB2 | 334076 | 11.12% | 97574 | 5.45% | 200860 | 10.84% | 3.42 | 2.04 | | |
| 35 | ssemi deleted ErbB2 | 112668 | 3.75% | 46720 | 2.61% | 144086 | 7.02% | 2.41 | 1.44 | | A9, D11, G10, C60 |
| 36 | TRAIL1 | 1199922 | 10.13% | 2251 | 1.45% | 1388 | 0.05% | 532.76 | 12.60 | ELISA, FACS | |
| 37 | TRAIL1 | 1046748 | 15.02% | 6154 | 3.97% | 4951 | 0.17% | 170.00 | 3.90 | ELISA, FACS | |
| 38 | TRAIL1 | 62433 | 0.94% | 402 | 0.26% | 39882 | 1.06% | 155.31 | 3.64 | ELISA, FACS | |
| 39 | TRAIL1 | 4697 | 0.07% | 690 | 0.44% | 0 | 0 | 6.81 | 0.14 | ELISA, FACS | |
| 40 | C-HcMAb modif-ication | 16746 | 0.31% | 1873 | 0.12% | 5870 | 0.20% |

FIGURE 10
Strategy 1 – CDRs L3 and H3, Illumina (custom)
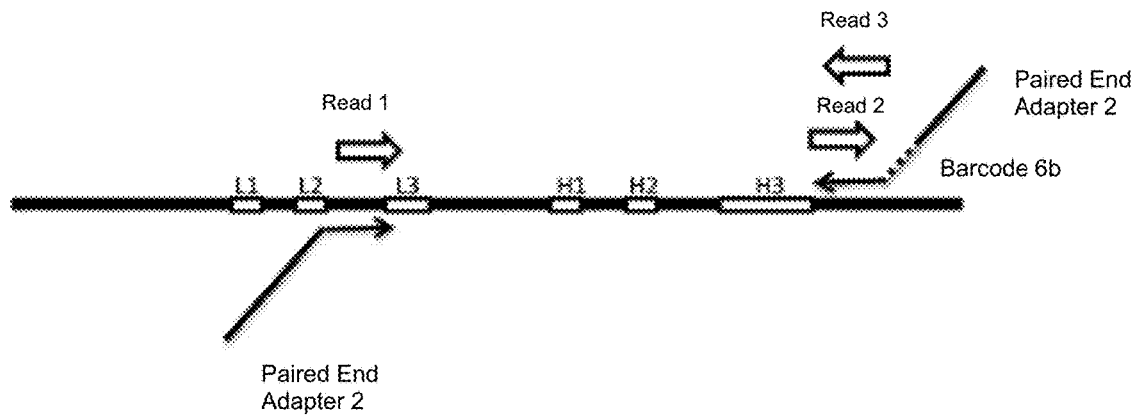
Strategy 2 – CDRs L3 and H3, and optionally H2 and H1, Illumina (standard)
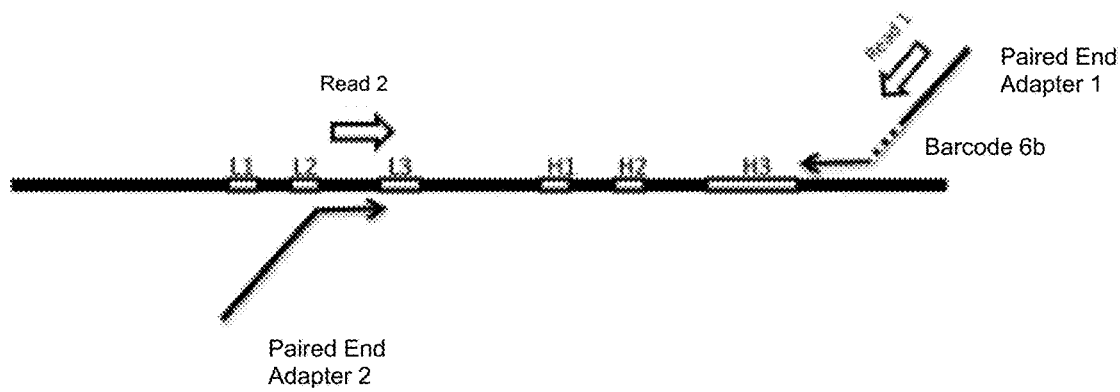
Strategy 3 – CDRs H3 only, IonTorrent (standard)
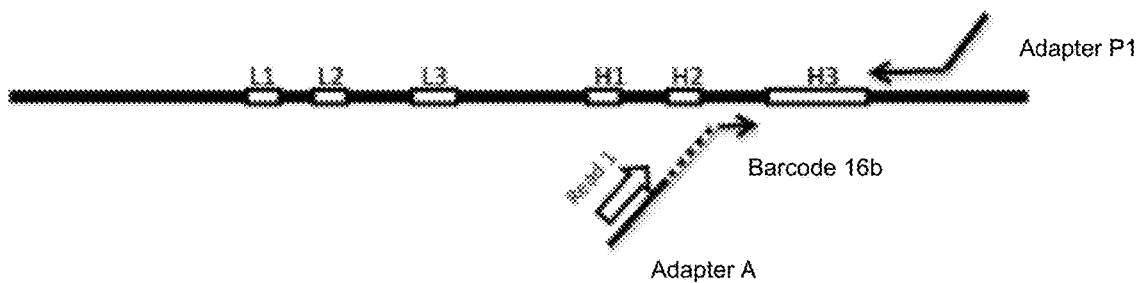

SEQUENCE LISTING

```
<160> NUMBER OF SEQ ID NOS: 266

<210> SEQ ID NO 1
<211> LENGTH: 58
<212> TYPE: DNA
<213> ORGANISM: Artificial Sequence
<220> FEATURE:
<223> OTHER INFORMATION: chemically synthesized

<400> SEQUENCE: 1
aatgatacgg cgaccaccga gatctacact ctttccctac acgacgctct tccgatct        58

<210> SEQ ID NO 2
<211> LENGTH: 5
<212> TYPE: DNA
<213> ORGANISM: Artificial Sequence
<220> FEATURE:
<223> OTHER INFORMATION: chemically synthesized

<400> SEQUENCE: 2 gagta                                                                    5

<210> SEQ ID NO 3
<211> LENGTH: 5
<212> TYPE: DNA
<213> ORGANISM: Artificial Sequence
<220> FEATURE:
<223> OTHER INFORMATION: chemically synthesized

<400> SEQUENCE: 3 ccaaa                                                                    5

<210> SEQ ID NO 4
<211> LENGTH: 5
<212> TYPE: DNA
<213> ORGANISM: Artificial Sequence
<220> FEATURE:
<223> OTHER INFORMATION: chemically synthesized
```

<400> SEQUENCE: 4 ttgtt                                                                    5

<210> SEQ ID NO 5
<211> LENGTH: 18
<212> TYPE: DNA
<213> ORGANISM: Artificial Sequence
<220> FEATURE:
<223> OTHER INFORMATION: chemically synthesized

<400> SEQUENCE: 5
gtctattatt gtgctcgc                                                     18

<210> SEQ ID NO 6
<211> LENGTH: 28
<212> TYPE: DNA
<213> ORGANISM: Artificial Sequence
<220> FEATURE:
<223> OTHER INFORMATION: chemically synthesized

<400> SEQUENCE: 6
caagcagaag acggcatacg agctcttc                                          28

<210> SEQ ID NO 7
<211> LENGTH: 18
<212> TYPE: DNA
<213> ORGANISM: Artificial Sequence
<220> FEATURE:
<223> OTHER INFORMATION: chemically synthesized

<400> SEQUENCE: 7
tccttgaccc cagtagtc                                                     18

<210> SEQ ID NO 8
<211> LENGTH: 18
<212> TYPE: DNA
<213> ORGANISM: Artificial Sequence
<220> FEATURE:
<223> OTHER INFORMATION: chemically synthesized

<400> SEQUENCE: 8
tacggttacg tttctggt                                                     18

<210> SEQ ID NO 9
<211> LENGTH: 18
<212> TYPE: DNA
<213> ORGANISM: Artificial Sequence
<220> FEATURE:
<223> OTHER INFORMATION: chemically synthesized

<400> SEQUENCE: 9
tacccgtctt acggtttg                                                     18

<210> SEQ ID NO 10
<211> LENGTH: 21
<212> TYPE: DNA
<213> ORGANISM: Artificial Sequence
<220> FEATURE:
<223> OTHER INFORMATION: chemically synthesized

<400> SEQUENCE: 10
tggtctccgg cttcttggtc t                                                 21

<210> SEQ ID NO 11

<210> SEQ ID NO 11
<211> LENGTH: 18
<212> TYPE: DNA
<213> ORGANISM: Artificial Sequence
<220> FEATURE:
<223> OTHER INFORMATION: chemically synthesized

<400> SEQUENCE: 11
ccgtggtctg gttactct                                              18

<210> SEQ ID NO 12
<211> LENGTH: 24
<212> TYPE: DNA
<213> ORGANISM: Artificial Sequence
<220> FEATURE:
<223> OTHER INFORMATION: chemically synthesized

<400> SEQUENCE: 12
tactcttact ggggtccgta ctac                                       24

<210> SEQ ID NO 13
<211> LENGTH: 36
<212> TYPE: DNA
<213> ORGANISM: Artificial Sequence
<220> FEATURE:
<223> OTHER INFORMATION: chemically synthesized

<400> SEQUENCE: 13
tgtaaaacga cggccagtgg acgcatcgtg gcccta                          36

<210> SEQ ID NO 14
<211> LENGTH: 35
<212> TYPE: DNA
<213> ORGANISM: Artificial Sequence
<220> FEATURE:
<223> OTHER INFORMATION: chemically synthesized

<400> SEQUENCE: 14
caggaaacag ctatgacccc ttggtggagg ccgag                           35

<210> SEQ ID NO 15
<211> LENGTH: 38
<212> TYPE: DNA
<213> ORGANISM: Artificial Sequence
<220> FEATURE:
<223> OTHER INFORMATION: chemically synthesized

<400> SEQUENCE: 15
tgtaaaacga cggccagtct gtcataaagt tgtcacgg                        38

<210> SEQ ID NO 16
<211> LENGTH: 35
<212> TYPE: DNA
<213> ORGANISM: Artificial Sequence
<220> FEATURE:
<223> OTHER INFORMATION: chemically synthesized

<400> SEQUENCE: 16
caggaaacag ctatgacccc ttggtaccct gtccg                           35

<210> SEQ ID NO 17
<211> LENGTH: 10
<212> TYPE: PRT
<213> ORGANISM: Artificial Sequence
<220> FEATURE:
<223> OTHER INFORMATION: chemically synthesized

<400> SEQUENCE: 17

Gln Gln Gly Trp His Tyr Ala Pro Ile Thr
1               5                   10

<210> SEQ ID NO 18
<211> LENGTH: 9
<212> TYPE: PRT
<213> ORGANISM: Artificial Sequence
<220> FEATURE:
<223> OTHER INFORMATION: chemically synthesized

<400> SEQUENCE: 18

Gly Phe Asn Leu Tyr Ser Ser Ser Met
1               5

<210> SEQ ID NO 19
<211> LENGTH: 10
<212> TYPE: PRT
<213> ORGANISM: Artificial Sequence
<220> FEATURE:
<223> OTHER INFORMATION: chemically synthesized

<400> SEQUENCE: 19

Tyr Ile Ser Pro Tyr Tyr Gly Tyr Thr Tyr
1               5                   10

<210> SEQ ID NO 20
<211> LENGTH: 17
<212> TYPE: PRT
<213> ORGANISM: Artificial Sequence
<220> FEATURE:
<223> OTHER INFORMATION: chemically synthesized

<400> SEQUENCE: 20

Ala Arg Ala Val Val His Tyr Trp Tyr Gly Tyr Val Ser Gly Phe Asp
1               5                   10                  15

Tyr

<210> SEQ ID NO 21
<211> LENGTH: 10
<212> TYPE: PRT
<213> ORGANISM: Artificial Sequence
<220> FEATURE:
<223> OTHER INFORMATION: chemically synthesized

<400> SEQUENCE: 21

Gln Gln Gly Trp Ser Ala Tyr Leu Ile Thr
1               5                   10

<210> SEQ ID NO 22
<211> LENGTH: 9
<212> TYPE: PRT
<213> ORGANISM: Artificial Sequence
<220> FEATURE:
<223> OTHER INFORMATION: chemically synthesized

<400> SEQUENCE: 22

Gly Phe Asn Ile Ser Tyr Ser Ser Ile
1               5

<210> SEQ ID NO 23
<211> LENGTH: 10
<212> TYPE: PRT
<213> ORGANISM: Artificial Sequence
<220> FEATURE:
<223> OTHER INFORMATION: chemically synthesized

```
<400> SEQUENCE: 23

Ser Ile Tyr Ser Ser Tyr Gly Tyr Thr Ser
1               5                   10

<210> SEQ ID NO 24
<211> LENGTH: 15
<212> TYPE: PRT
<213> ORGANISM: Artificial Sequence
<220> FEATURE:
<223> OTHER INFORMATION: chemically synthesized

<400> SEQUENCE: 24

Ala Arg Gly Trp Val Pro Ala Tyr Pro Ser Tyr Gly Leu Asp Tyr
1               5                   10                  15

<210> SEQ ID NO 25
<211> LENGTH: 9
<212> TYPE: PRT
<213> ORGANISM: Artificial Sequence
<220> FEATURE:
<223> OTHER INFORMATION: chemically synthesized

<400> SEQUENCE: 25

Gln Gln Ser Ser Tyr Ser Leu Ile Thr
1               5

<210> SEQ ID NO 26
<211> LENGTH: 9
<212> TYPE: PRT
<213> ORGANISM: Artificial Sequence
<220> FEATURE:
<223> OTHER INFORMATION: chemically synthesized

<400> SEQUENCE: 26

Gly Phe Asn Leu Tyr Ser Tyr Tyr Ile
1               5

<210> SEQ ID NO 27
<211> LENGTH: 10
<212> TYPE: PRT
<213> ORGANISM: Artificial Sequence
<220> FEATURE:
<223> OTHER INFORMATION: chemically synthesized

<400> SEQUENCE: 27

Ser Ile Tyr Ser Tyr Ser Ser Ser Thr Ser
1               5                   10

<210> SEQ ID NO 28
<211> LENGTH: 23
<212> TYPE: PRT
<213> ORGANISM: Artificial Sequence
<220> FEATURE:
<223> OTHER INFORMATION: chemically synthesized

<400> SEQUENCE: 28

Ala Arg Trp Gly Ser Ser Val Tyr Ala Trp Ser Pro Ala Ser Trp Ser
1               5                   10                  15

Pro Pro Pro Gly Met Asp Tyr
            20

<210> SEQ ID NO 29
<211> LENGTH: 9
<212> TYPE: PRT
<213> ORGANISM: Artificial Sequence
<220> FEATURE:
```

```
<223> OTHER INFORMATION: chemically synthesized

<400> SEQUENCE: 29

Gln Gln Ser Ser Phe Trp Pro Ile Thr
1               5

<210> SEQ ID NO 30
<211> LENGTH: 9
<212> TYPE: PRT
<213> ORGANISM: Artificial Sequence
<220> FEATURE:
<223> OTHER INFORMATION: chemically synthesized

<400> SEQUENCE: 30

Gly Phe Asn Ile Ser Ser Ser Tyr Met
1               5

<210> SEQ ID NO 31
<211> LENGTH: 10
<212> TYPE: PRT
<213> ORGANISM: Artificial Sequence
<220> FEATURE:
<223> OTHER INFORMATION: chemically synthesized

<400> SEQUENCE: 31

Ser Ile Tyr Pro Ser Tyr Gly Tyr Thr Ser
1               5                   10

<210> SEQ ID NO 32
<211> LENGTH: 18
<212> TYPE: PRT
<213> ORGANISM: Artificial Sequence
<220> FEATURE:
<223> OTHER INFORMATION: chemically synthesized

<400> SEQUENCE: 32

Ala Arg Ser Tyr Tyr Trp Trp Gly Pro Trp Ser Gly Tyr Ser Gly Met
1               5                   10                  15

Asp Tyr

<210> SEQ ID NO 33
<211> LENGTH: 9
<212> TYPE: PRT
<213> ORGANISM: Artificial Sequence
<220> FEATURE:
<223> OTHER INFORMATION: chemically synthesized

<400> SEQUENCE: 33

Gln Gln Ser Trp Tyr Ser Leu Ile Thr
1               5

<210> SEQ ID NO 34
<211> LENGTH: 9
<212> TYPE: PRT
<213> ORGANISM: Artificial Sequence
<220> FEATURE:
<223> OTHER INFORMATION: chemically synthesized

<400> SEQUENCE: 34

Gly Phe Asn Ile Ser Ser Ser Ser Met
1               5

<210> SEQ ID NO 35
<211> LENGTH: 10
<212> TYPE: PRT
<213> ORGANISM: Artificial Sequence
```

```
<220> FEATURE:
<223> OTHER INFORMATION: chemically synthesized

<400> SEQUENCE: 35

Ser Ile Tyr Ser Ser Tyr Ser Ser Thr Tyr
1               5                   10

<210> SEQ ID NO 36
<211> LENGTH: 22
<212> TYPE: PRT
<213> ORGANISM: Artificial Sequence
<220> FEATURE:
<223> OTHER INFORMATION: chemically synthesized

<400> SEQUENCE: 36

Ala Arg Pro His Pro Tyr Ile Pro Tyr Tyr Ser Tyr Trp Gly Pro Tyr
1               5                   10                  15

Tyr Ser Gly Leu Asp Tyr
            20

<210> SEQ ID NO 37
<211> LENGTH: 14
<212> TYPE: PRT
<213> ORGANISM: Artificial Sequence
<220> FEATURE:
<223> OTHER INFORMATION: chemically synthesized

<400> SEQUENCE: 37

Tyr Tyr Trp Ser Tyr Tyr Ser Gly Gly Gly Gly Phe Asp Tyr
1               5                   10

<210> SEQ ID NO 38
<211> LENGTH: 5
<212> TYPE: PRT
<213> ORGANISM: Artificial Sequence
<220> FEATURE:
<223> OTHER INFORMATION: chemically synthesized

<400> SEQUENCE: 38

Trp Ala Met Asp Tyr
1               5

<210> SEQ ID NO 39
<211> LENGTH: 10
<212> TYPE: PRT
<213> ORGANISM: Artificial Sequence
<220> FEATURE:
<223> OTHER INFORMATION: chemically synthesized

<400> SEQUENCE: 39

Tyr Ala Tyr Ser Val Ala Gly Leu Asp Tyr
1               5                   10

<210> SEQ ID NO 40
<211> LENGTH: 15
<212> TYPE: PRT
<213> ORGANISM: Artificial Sequence
<220> FEATURE:
<223> OTHER INFORMATION: chemically synthesized

<400> SEQUENCE: 40

Ala Val Val His Tyr Trp Tyr Gly Tyr Val Ser Gly Phe Asp Tyr
1               5                   10                  15

<210> SEQ ID NO 41
<211> LENGTH: 8
```

```
<212> TYPE: PRT
<213> ORGANISM: Artificial Sequence
<220> FEATURE:
<223> OTHER INFORMATION: chemically synthesized

<400> SEQUENCE: 41

Phe Gly Trp Tyr Gly Ile Asp Tyr
1               5

<210> SEQ ID NO 42
<211> LENGTH: 13
<212> TYPE: PRT
<213> ORGANISM: Artificial Sequence
<220> FEATURE:
<223> OTHER INFORMATION: chemically synthesized

<400> SEQUENCE: 42

Gly Trp Val Pro Ala Tyr Pro Ser Tyr Gly Leu Asp Tyr
1               5                   10

<210> SEQ ID NO 43
<211> LENGTH: 19
<212> TYPE: PRT
<213> ORGANISM: Artificial Sequence
<220> FEATURE:
<223> OTHER INFORMATION: chemically synthesized

<400> SEQUENCE: 43

Tyr Val Trp Gly Trp Phe Tyr Val Ser His Tyr Ser Ser Gly Ala Ser
1               5                   10                  15

Phe Asp Tyr

<210> SEQ ID NO 44
<211> LENGTH: 11
<212> TYPE: PRT
<213> ORGANISM: Artificial Sequence
<220> FEATURE:
<223> OTHER INFORMATION: chemically synthesized

<400> SEQUENCE: 44

His Ser Ala Tyr Tyr Trp Pro Gly Ile Asp Tyr
1               5                   10

<210> SEQ ID NO 45
<211> LENGTH: 12
<212> TYPE: PRT
<213> ORGANISM: Artificial Sequence
<220> FEATURE:
<223> OTHER INFORMATION: chemically synthesized

<400> SEQUENCE: 45

Phe Tyr Trp Ser Tyr Pro Ser Tyr Ala Met Asp Tyr
1               5                   10

<210> SEQ ID NO 46
<211> LENGTH: 9
<212> TYPE: PRT
<213> ORGANISM: Artificial Sequence
<220> FEATURE:
<223> OTHER INFORMATION: chemically synthesized

<400> SEQUENCE: 46

Gly Tyr Tyr Tyr Pro Ala Leu Asp Tyr
1               5

<210> SEQ ID NO 47
```

```
<211> LENGTH: 5
<212> TYPE: PRT
<213> ORGANISM: Artificial Sequence
<220> FEATURE:
<223> OTHER INFORMATION: chemically synthesized

<400> SEQUENCE: 47

Ser Gly Met Asp Tyr
1               5

<210> SEQ ID NO 48
<211> LENGTH: 19
<212> TYPE: PRT
<213> ORGANISM: Artificial Sequence
<220> FEATURE:
<223> OTHER INFORMATION: chemically synthesized

<400> SEQUENCE: 48

Trp Gly Ser Ser Val Tyr Ala Trp Ser Pro Ala Ser Trp Ser Pro Pro
1               5                   10                  15

Pro Asp Tyr

<210> SEQ ID NO 49
<211> LENGTH: 17
<212> TYPE: PRT
<213> ORGANISM: Artificial Sequence
<220> FEATURE:
<223> OTHER INFORMATION: chemically synthesized

<400> SEQUENCE: 49

Thr Val Arg Gly Ser Lys Lys Pro Tyr Phe Ser Gly Trp Ala Met Asp
1               5                   10                  15

Tyr

<210> SEQ ID NO 50
<211> LENGTH: 16
<212> TYPE: PRT
<213> ORGANISM: Artificial Sequence
<220> FEATURE:
<223> OTHER INFORMATION: chemically synthesized

<400> SEQUENCE: 50

Ser Tyr Tyr Trp Trp Gly Pro Trp Ser Gly Tyr Ser Gly Met Asp Tyr
1               5                   10                  15

<210> SEQ ID NO 51
<211> LENGTH: 12
<212> TYPE: PRT
<213> ORGANISM: Artificial Sequence
<220> FEATURE:
<223> OTHER INFORMATION: chemically synthesized

<400> SEQUENCE: 51

Tyr Gly Tyr Trp Trp Val Trp Tyr Ala Phe Asp Tyr
1               5                   10

<210> SEQ ID NO 52
<211> LENGTH: 19
<212> TYPE: PRT
<213> ORGANISM: Artificial Sequence
<220> FEATURE:
<223> OTHER INFORMATION: chemically synthesized

<400> SEQUENCE: 52

Gly Ser Val Val His Ser Phe Ala Ser Tyr Val Trp Gly Trp Ser Val
1               5                   10                  15
```

Gly Asp Tyr

```
<210> SEQ ID NO 53
<211> LENGTH: 6
<212> TYPE: PRT
<213> ORGANISM: Artificial Sequence
<220> FEATURE:
<223> OTHER INFORMATION: chemically synthesized

<400> SEQUENCE: 53

Ala Tyr Gly Met Asp Tyr
1               5

<210> SEQ ID NO 54
<211> LENGTH: 8
<212> TYPE: PRT
<213> ORGANISM: Artificial Sequence
<220> FEATURE:
<223> OTHER INFORMATION: chemically synthesized

<400> SEQUENCE: 54

Tyr Tyr Tyr Phe Gly Leu Asp Tyr
1               5

<210> SEQ ID NO 55
<211> LENGTH: 8
<212> TYPE: PRT
<213> ORGANISM: Artificial Sequence
<220> FEATURE:
<223> OTHER INFORMATION: chemically synthesized

<400> SEQUENCE: 55

Gly Trp Trp Tyr Gly Met Asp Tyr
1               5

<210> SEQ ID NO 56
<211> LENGTH: 5
<212> TYPE: PRT
<213> ORGANISM: Artificial Sequence
<220> FEATURE:
<223> OTHER INFORMATION: chemically synthesized

<400> SEQUENCE: 56

Tyr Ala Phe Asp Tyr
1               5

<210> SEQ ID NO 57
<211> LENGTH: 13
<212> TYPE: PRT
<213> ORGANISM: Artificial Sequence
<220> FEATURE:
<223> OTHER INFORMATION: chemically synthesized

<400> SEQUENCE: 57

Gly Tyr Trp Gly Ser Phe Trp Ser Ala Gly Ser Asp Tyr
1               5                   10

<210> SEQ ID NO 58
<211> LENGTH: 12
<212> TYPE: PRT
<213> ORGANISM: Artificial Sequence
<220> FEATURE:
<223> OTHER INFORMATION: chemically synthesized

<400> SEQUENCE: 58

Val His Gly His Tyr Gly Ser Tyr Gly Phe Asp Tyr
```

```
1               5                   10

<210> SEQ ID NO 59
<211> LENGTH: 8
<212> TYPE: PRT
<213> ORGANISM: Artificial Sequence
<220> FEATURE:
<223> OTHER INFORMATION: chemically synthesized

<400> SEQUENCE: 59

Val Ala Trp Tyr Gly Leu Asp Tyr
1               5

<210> SEQ ID NO 60
<211> LENGTH: 8
<212> TYPE: PRT
<213> ORGANISM: Artificial Sequence
<220> FEATURE:
<223> OTHER INFORMATION: chemically synthesized

<400> SEQUENCE: 60

Trp Gly Tyr Phe Gly Leu Asp Tyr
1               5

<210> SEQ ID NO 61
<211> LENGTH: 12
<212> TYPE: PRT
<213> ORGANISM: Artificial Sequence
<220> FEATURE:
<223> OTHER INFORMATION: chemically synthesized

<400> SEQUENCE: 61

Val Ser Ala Tyr Tyr Tyr Trp Val Gly Phe Asp Tyr
1               5                   10

<210> SEQ ID NO 62
<211> LENGTH: 19
<212> TYPE: PRT
<213> ORGANISM: Artificial Sequence
<220> FEATURE:
<223> OTHER INFORMATION: chemically synthesized

<400> SEQUENCE: 62

Pro His Pro Tyr Ile Pro Tyr Ser Tyr Trp Gly Pro Tyr Tyr Ser
1               5                   10                  15

Gly Asp Tyr

<210> SEQ ID NO 63
<211> LENGTH: 13
<212> TYPE: PRT
<213> ORGANISM: Artificial Sequence
<220> FEATURE:
<223> OTHER INFORMATION: chemically synthesized

<400> SEQUENCE: 63

Val Trp Pro Ser Ser Ala Ser Tyr Val Gly Phe Asp Tyr
1               5                   10

<210> SEQ ID NO 64
<211> LENGTH: 10
<212> TYPE: PRT
<213> ORGANISM: Artificial Sequence
<220> FEATURE:
<223> OTHER INFORMATION: chemically synthesized

<400> SEQUENCE: 64
```

Tyr Ala Ser Tyr Trp Gly Ala Phe Asp Tyr
1               5                   10

<210> SEQ ID NO 65
<211> LENGTH: 10
<212> TYPE: PRT
<213> ORGANISM: Artificial Sequence
<220> FEATURE:
<223> OTHER INFORMATION: chemically synthesized

<400> SEQUENCE: 65

Tyr Tyr Val Trp Tyr Trp Gly Leu Asp Tyr
1               5                   10

<210> SEQ ID NO 66
<211> LENGTH: 8
<212> TYPE: PRT
<213> ORGANISM: Artificial Sequence
<220> FEATURE:
<223> OTHER INFORMATION: chemically synthesized

<400> SEQUENCE: 66

Phe Gly Tyr Tyr Gly Leu Asp Tyr
1               5

<210> SEQ ID NO 67
<211> LENGTH: 11
<212> TYPE: PRT
<213> ORGANISM: Artificial Sequence
<220> FEATURE:
<223> OTHER INFORMATION: chemically synthesized

<400> SEQUENCE: 67

His Ser Ser Tyr Tyr Ser Tyr Ala Leu Asp Tyr
1               5                   10

<210> SEQ ID NO 68
<211> LENGTH: 19
<212> TYPE: PRT
<213> ORGANISM: Artificial Sequence
<220> FEATURE:
<223> OTHER INFORMATION: chemically synthesized

<400> SEQUENCE: 68

Gly Tyr Ser Tyr Gly Tyr Ser Val Tyr Ser Trp Ser Gly Tyr Gly Ala
1               5                   10                  15

His Asp Tyr

<210> SEQ ID NO 69
<211> LENGTH: 10
<212> TYPE: PRT
<213> ORGANISM: Artificial Sequence
<220> FEATURE:
<223> OTHER INFORMATION: chemically synthesized

<400> SEQUENCE: 69

Ala Tyr Ser Tyr Ala Tyr Gly Leu Asp Tyr
1               5                   10

<210> SEQ ID NO 70
<211> LENGTH: 12
<212> TYPE: PRT
<213> ORGANISM: Artificial Sequence
<220> FEATURE:
<223> OTHER INFORMATION: chemically synthesized

<400> SEQUENCE: 70

```
Ala Ser Ala His Tyr Gly Pro Trp Ala Phe Asp Tyr
1               5                   10
```

<210> SEQ ID NO 71
<211> LENGTH: 15
<212> TYPE: PRT
<213> ORGANISM: Artificial Sequence
<220> FEATURE:
<223> OTHER INFORMATION: chemically synthesized

<400> SEQUENCE: 71

```
Gly Ser Ser Trp Ser Phe Phe His Tyr Phe Gly Gly Ile Asp Tyr
1               5                   10                  15
```

<210> SEQ ID NO 72
<211> LENGTH: 11
<212> TYPE: PRT
<213> ORGANISM: Artificial Sequence
<220> FEATURE:
<223> OTHER INFORMATION: chemically synthesized

<400> SEQUENCE: 72

```
Gly Pro Trp His Gly Ser Tyr Gly Leu Asp Tyr
1               5                   10
```

<210> SEQ ID NO 73
<211> LENGTH: 10
<212> TYPE: PRT
<213> ORGANISM: Artificial Sequence
<220> FEATURE:
<223> OTHER INFORMATION: chemically synthesized

<400> SEQUENCE: 73

```
Ser Trp Ala Ala Gly Tyr Ala Met Asp Tyr
1               5                   10
```

<210> SEQ ID NO 74
<211> LENGTH: 15
<212> TYPE: PRT
<213> ORGANISM: Artificial Sequence
<220> FEATURE:
<223> OTHER INFORMATION: chemically synthesized

<400> SEQUENCE: 74

```
Ser Trp Ala Val Tyr Pro Ser Ala Ser Trp Ser Gly Phe Asp Tyr
1               5                   10                  15
```

<210> SEQ ID NO 75
<211> LENGTH: 19
<212> TYPE: PRT
<213> ORGANISM: Artificial Sequence
<220> FEATURE:
<223> OTHER INFORMATION: chemically synthesized

<400> SEQUENCE: 75

```
Tyr Gly Pro Gly Trp Ser Tyr Tyr Gly Tyr Trp Gly Tyr Ala Ala Pro
1               5                   10                  15

Ala Asp Tyr
```

<210> SEQ ID NO 76
<211> LENGTH: 15
<212> TYPE: PRT
<213> ORGANISM: Artificial Sequence
<220> FEATURE:
<223> OTHER INFORMATION: chemically synthesized

```
<400> SEQUENCE: 76

Tyr Gly Gly Gly Gly Tyr Trp Ala Tyr Val Ser Ala Leu Asp Tyr
1               5                   10                  15

<210> SEQ ID NO 77
<211> LENGTH: 12
<212> TYPE: PRT
<213> ORGANISM: Artificial Sequence
<220> FEATURE:
<223> OTHER INFORMATION: chemically synthesized

<400> SEQUENCE: 77

Ser Ser Ser Gly Ser Gly Val His Gly Ile Asp Tyr
1               5                   10

<210> SEQ ID NO 78
<211> LENGTH: 9
<212> TYPE: PRT
<213> ORGANISM: Artificial Sequence
<220> FEATURE:
<223> OTHER INFORMATION: chemically synthesized

<400> SEQUENCE: 78

Tyr Ser Gly His Ser Ala Leu Asp Tyr
1               5

<210> SEQ ID NO 79
<211> LENGTH: 11
<212> TYPE: PRT
<213> ORGANISM: Artificial Sequence
<220> FEATURE:
<223> OTHER INFORMATION: chemically synthesized

<400> SEQUENCE: 79

His Ser Ala Tyr Tyr Ser Tyr Ala Leu Asp Tyr
1               5                   10

<210> SEQ ID NO 80
<211> LENGTH: 18
<212> TYPE: PRT
<213> ORGANISM: Artificial Sequence
<220> FEATURE:
<223> OTHER INFORMATION: chemically synthesized

<400> SEQUENCE: 80

Ser Tyr Gly Val Val Trp Tyr Ala Ser Ser Ala Ala Ala Gly Leu
1               5                   10                  15

Asp Tyr

<210> SEQ ID NO 81
<211> LENGTH: 8
<212> TYPE: PRT
<213> ORGANISM: Artificial Sequence
<220> FEATURE:
<223> OTHER INFORMATION: chemically synthesized

<400> SEQUENCE: 81

Trp Ser Tyr His Gly Met Asp Tyr
1               5

<210> SEQ ID NO 82
<211> LENGTH: 8
<212> TYPE: PRT
<213> ORGANISM: Artificial Sequence
<220> FEATURE:
<223> OTHER INFORMATION: chemically synthesized
```

<400> SEQUENCE: 82

Tyr Tyr Ser Ala Ala Leu Asp Tyr
1               5

<210> SEQ ID NO 83
<211> LENGTH: 19
<212> TYPE: PRT
<213> ORGANISM: Artificial Sequence
<220> FEATURE:
<223> OTHER INFORMATION: chemically synthesized

<400> SEQUENCE: 83

Gly Ser Ser Tyr Ser Gly Tyr Tyr Tyr Ser Ser Ser Ser Ser Gly
1               5                   10                  15

Leu Asp Tyr

<210> SEQ ID NO 84
<211> LENGTH: 5
<212> TYPE: PRT
<213> ORGANISM: Artificial Sequence
<220> FEATURE:
<223> OTHER INFORMATION: chemically synthesized

<400> SEQUENCE: 84

Ala Gly Ile Asp Tyr
1               5

<210> SEQ ID NO 85
<211> LENGTH: 5
<212> TYPE: PRT
<213> ORGANISM: Artificial Sequence
<220> FEATURE:
<223> OTHER INFORMATION: chemically synthesized

<400> SEQUENCE: 85

Trp Ala Phe Asp Tyr
1               5

<210> SEQ ID NO 86
<211> LENGTH: 16
<212> TYPE: PRT
<213> ORGANISM: Artificial Sequence
<220> FEATURE:
<223> OTHER INFORMATION: chemically synthesized

<400> SEQUENCE: 86

Ser Ser Trp Tyr Ser Phe Gly Val Gly Ala Ser Tyr Gly Leu Asp Tyr
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: chemically synthesized

<400> SEQUENCE: 87

Tyr Gly Gly Gly Gly Tyr Trp Ala Tyr Val Ser Ala Phe Asp Tyr
1               5                   10                  15

<210> SEQ ID NO 88
<211> LENGTH: 11
<212> TYPE: PRT
<213> ORGANISM: Artificial Sequence
<220> FEATURE:

```
<223> OTHER INFORMATION: chemically synthesized

<400> SEQUENCE: 88

Tyr Trp Tyr Tyr Gly Tyr Tyr Ala Phe Asp Tyr
1               5                   10

<210> SEQ ID NO 89
<211> LENGTH: 10
<212> TYPE: PRT
<213> ORGANISM: Artificial Sequence
<220> FEATURE:
<223> OTHER INFORMATION: chemically synthesized

<400> SEQUENCE: 89

Pro Gly Tyr Val Ser Val Gly Phe Asp Tyr
1               5                   10

<210> SEQ ID NO 90
<211> LENGTH: 10
<212> TYPE: PRT
<213> ORGANISM: Artificial Sequence
<220> FEATURE:
<223> OTHER INFORMATION: chemically synthesized

<400> SEQUENCE: 90

Ser Gly Pro Tyr Phe Tyr Gly Leu Asp Tyr
1               5                   10

<210> SEQ ID NO 91
<211> LENGTH: 16
<212> TYPE: PRT
<213> ORGANISM: Artificial Sequence
<220> FEATURE:
<223> OTHER INFORMATION: chemically synthesized

<400> SEQUENCE: 91

His Val Ala Ser Ser Phe Trp Tyr Ser Trp Ser Tyr Gly Ile Asp Tyr
1               5                   10                  15

<210> SEQ ID NO 92
<211> LENGTH: 8
<212> TYPE: PRT
<213> ORGANISM: Artificial Sequence
<220> FEATURE:
<223> OTHER INFORMATION: chemically synthesized

<400> SEQUENCE: 92

Ser Gly Ala Ser Gly Phe Asp Tyr
1               5

<210> SEQ ID NO 93
<211> LENGTH: 5
<212> TYPE: PRT
<213> ORGANISM: Artificial Sequence
<220> FEATURE:
<223> OTHER INFORMATION: chemically synthesized

<400> SEQUENCE: 93

Trp Ala Leu Asp Tyr
1               5

<210> SEQ ID NO 94
<211> LENGTH: 14
<212> TYPE: PRT
<213> ORGANISM: Artificial Sequence
<220> FEATURE:
<223> OTHER INFORMATION: chemically synthesized
```

```
<400> SEQUENCE: 94

Trp Ser Ser Gly Tyr Tyr Trp Ser Trp Gly Gly Met Asp Tyr
1               5                   10

<210> SEQ ID NO 95
<211> LENGTH: 11
<212> TYPE: PRT
<213> ORGANISM: Artificial Sequence
<220> FEATURE:
<223> OTHER INFORMATION: chemically synthesized

<400> SEQUENCE: 95

Val Ser Ala Ala Ser Ser Val Gly Phe Asp Tyr
1               5                   10

<210> SEQ ID NO 96
<211> LENGTH: 19
<212> TYPE: PRT
<213> ORGANISM: Artificial Sequence
<220> FEATURE:
<223> OTHER INFORMATION: chemically synthesized

<400> SEQUENCE: 96

Ser Tyr Gly His Tyr Gly Val Tyr Gly Ser Trp Trp Trp Tyr Gly
1               5                   10                  15

Ala Asp Tyr

<210> SEQ ID NO 97
<211> LENGTH: 19
<212> TYPE: PRT
<213> ORGANISM: Artificial Sequence
<220> FEATURE:
<223> OTHER INFORMATION: chemically synthesized

<400> SEQUENCE: 97

His Ser Pro Pro Tyr His Tyr Ser Pro Tyr Tyr Ser Trp Ser Ala Tyr
1               5                   10                  15

Ala Asp Tyr

<210> SEQ ID NO 98
<211> LENGTH: 18
<212> TYPE: PRT
<213> ORGANISM: Artificial Sequence
<220> FEATURE:
<223> OTHER INFORMATION: chemically synthesized

<400> SEQUENCE: 98

Tyr Ser Ser His Phe Ala Ala Tyr Tyr Phe Trp Ser Val Trp Ala Leu
1               5                   10                  15

Asp Tyr

<210> SEQ ID NO 99
<211> LENGTH: 8
<212> TYPE: PRT
<213> ORGANISM: Artificial Sequence
<220> FEATURE:
<223> OTHER INFORMATION: chemically synthesized

<400> SEQUENCE: 99

Trp Tyr His Ser Ala Met Asp Tyr
1               5

<210> SEQ ID NO 100
```

<211> LENGTH: 9
<212> TYPE: PRT
<213> ORGANISM: Artificial Sequence
<220> FEATURE:
<223> OTHER INFORMATION: chemically synthesized

<400> SEQUENCE: 100

Val Tyr Trp Trp Val Gly Met Asp Tyr
1               5

<210> SEQ ID NO 101
<211> LENGTH: 14
<212> TYPE: PRT
<213> ORGANISM: Artificial Sequence
<220> FEATURE:
<223> OTHER INFORMATION: chemically synthesized

<400> SEQUENCE: 101

Trp Tyr Tyr Gly Gly Tyr Tyr Gly Ala Tyr Ala Leu Asp Tyr
1               5                   10

<210> SEQ ID NO 102
<211> LENGTH: 9
<212> TYPE: PRT
<213> ORGANISM: Artificial Sequence
<220> FEATURE:
<223> OTHER INFORMATION: chemically synthesized

<400> SEQUENCE: 102

Gly Trp Gly Trp Ser Gly Leu Asp Tyr
1               5

<210> SEQ ID NO 103
<211> LENGTH: 18
<212> TYPE: PRT
<213> ORGANISM: Artificial Sequence
<220> FEATURE:
<223> OTHER INFORMATION: chemically synthesized

<400> SEQUENCE: 103

Tyr Ser Ala Trp Val Trp Ser Ser His Ser Trp Ala Trp His Ala Leu
1               5                   10                  15

Asp Tyr

<210> SEQ ID NO 104
<211> LENGTH: 7
<212> TYPE: PRT
<213> ORGANISM: Artificial Sequence
<220> FEATURE:
<223> OTHER INFORMATION: chemically synthesized

<400> SEQUENCE: 104

Tyr Gly His Gly Phe Asp Tyr
1               5

<210> SEQ ID NO 105
<211> LENGTH: 9
<212> TYPE: PRT
<213> ORGANISM: Artificial Sequence
<220> FEATURE:
<223> OTHER INFORMATION: chemically synthesized

<400> SEQUENCE: 105

Gly Ala His Trp Tyr Gly Ile Asp Tyr
1               5

```
<210> SEQ ID NO 106
<211> LENGTH: 8
<212> TYPE: PRT
<213> ORGANISM: Artificial Sequence
<220> FEATURE:
<223> OTHER INFORMATION: chemically synthesized

<400> SEQUENCE: 106

Val Tyr Gly His Ala Met Asp Tyr
1               5

<210> SEQ ID NO 107
<211> LENGTH: 5
<212> TYPE: PRT
<213> ORGANISM: Artificial Sequence
<220> FEATURE:
<223> OTHER INFORMATION: chemically synthesized

<400> SEQUENCE: 107

Val Gly Leu Asp Tyr
1               5

<210> SEQ ID NO 108
<211> LENGTH: 11
<212> TYPE: PRT
<213> ORGANISM: Artificial Sequence
<220> FEATURE:
<223> OTHER INFORMATION: chemically synthesized

<400> SEQUENCE: 108

Tyr Ala Ala Tyr Tyr Ser Tyr Ala Leu Asp Tyr
1               5                   10

<210> SEQ ID NO 109
<211> LENGTH: 16
<212> TYPE: PRT
<213> ORGANISM: Artificial Sequence
<220> FEATURE:
<223> OTHER INFORMATION: chemically synthesized

<400> SEQUENCE: 109

Ser Pro Tyr Trp Tyr Tyr Trp Trp Val Trp Ser Ala Gly Phe Asp Tyr
1               5                   10                  15

<210> SEQ ID NO 110
<211> LENGTH: 11
<212> TYPE: PRT
<213> ORGANISM: Artificial Sequence
<220> FEATURE:
<223> OTHER INFORMATION: chemically synthesized

<400> SEQUENCE: 110

Ala Pro Trp Ser Gly Ser Ser Ala Phe Asp Tyr
1               5                   10

<210> SEQ ID NO 111
<211> LENGTH: 10
<212> TYPE: PRT
<213> ORGANISM: Artificial Sequence
<220> FEATURE:
<223> OTHER INFORMATION: chemically synthesized

<400> SEQUENCE: 111

Val Ala Ala Tyr Trp Val Ala Met Asp Tyr
1               5                   10

<210> SEQ ID NO 112
```

```
<211> LENGTH: 12
<212> TYPE: PRT
<213> ORGANISM: Artificial Sequence
<220> FEATURE:
<223> OTHER INFORMATION: chemically synthesized

<400> SEQUENCE: 112

Tyr Ser Ala Gly Gly Trp Val Tyr Gly Phe Asp Tyr
1               5                   10

<210> SEQ ID NO 113
<211> LENGTH: 10
<212> TYPE: PRT
<213> ORGANISM: Artificial Sequence
<220> FEATURE:
<223> OTHER INFORMATION: chemically synthesized

<400> SEQUENCE: 113

Ser Tyr Ser Trp Tyr Phe Ala Met Asp Tyr
1               5                   10

<210> SEQ ID NO 114
<211> LENGTH: 8
<212> TYPE: PRT
<213> ORGANISM: Artificial Sequence
<220> FEATURE:
<223> OTHER INFORMATION: chemically synthesized

<400> SEQUENCE: 114

Ala Trp Val Ser Ala Leu Asp Tyr
1               5

<210> SEQ ID NO 115
<211> LENGTH: 16
<212> TYPE: PRT
<213> ORGANISM: Artificial Sequence
<220> FEATURE:
<223> OTHER INFORMATION: chemically synthesized

<400> SEQUENCE: 115

Gly Trp His Val Val Pro Ser Gly Phe Phe Trp His Ala Ile Asp Tyr
1               5                   10                  15

<210> SEQ ID NO 116
<211> LENGTH: 8
<212> TYPE: PRT
<213> ORGANISM: Artificial Sequence
<220> FEATURE:
<223> OTHER INFORMATION: chemically synthesized

<400> SEQUENCE: 116

Gly Ser Ser Tyr Asp Met Asp Tyr
1               5

<210> SEQ ID NO 117
<211> LENGTH: 11
<212> TYPE: PRT
<213> ORGANISM: Artificial Sequence
<220> FEATURE:
<223> OTHER INFORMATION: chemically synthesized

<400> SEQUENCE: 117

Phe Pro Ala Tyr His Ser His Ala Phe Asp Tyr
1               5                   10

<210> SEQ ID NO 118
<211> LENGTH: 14
```

```
<212> TYPE: PRT
<213> ORGANISM: Artificial Sequence
<220> FEATURE:
<223> OTHER INFORMATION: chemically synthesized

<400> SEQUENCE: 118

Gly Ala Tyr Trp Gly Tyr His Ala Ser Tyr Ala Met Asp Tyr
1               5                   10

<210> SEQ ID NO 119
<211> LENGTH: 19
<212> TYPE: PRT
<213> ORGANISM: Artificial Sequence
<220> FEATURE:
<223> OTHER INFORMATION: chemically synthesized

<400> SEQUENCE: 119

Trp Ser Tyr Tyr Ser Gly Gly Val Tyr Ala Ser Ser Trp Ser Trp Gly
1               5                   10                  15

Ala Asp Tyr

<210> SEQ ID NO 120
<211> LENGTH: 19
<212> TYPE: PRT
<213> ORGANISM: Artificial Sequence
<220> FEATURE:
<223> OTHER INFORMATION: chemically synthesized

<400> SEQUENCE: 120

Tyr Val Gly Trp Gly Val Ser Ser Tyr His Ser Ser Tyr Val Val Gly
1               5                   10                  15

Ala Asp Tyr

<210> SEQ ID NO 121
<211> LENGTH: 5
<212> TYPE: PRT
<213> ORGANISM: Artificial Sequence
<220> FEATURE:
<223> OTHER INFORMATION: chemically synthesized

<400> SEQUENCE: 121

Tyr Ala Met Asp Tyr
1               5

<210> SEQ ID NO 122
<211> LENGTH: 9
<212> TYPE: PRT
<213> ORGANISM: Artificial Sequence
<220> FEATURE:
<223> OTHER INFORMATION: chemically synthesized

<400> SEQUENCE: 122

Pro Gly Trp Ser Tyr Gly Leu Asp Tyr
1               5

<210> SEQ ID NO 123
<211> LENGTH: 5
<212> TYPE: PRT
<213> ORGANISM: Artificial Sequence
<220> FEATURE:
<223> OTHER INFORMATION: chemically synthesized

<400> SEQUENCE: 123

His Gly Ile Asp Tyr
1               5
```

<210> SEQ ID NO 124
<211> LENGTH: 19
<212> TYPE: PRT
<213> ORGANISM: Artificial Sequence
<220> FEATURE:
<223> OTHER INFORMATION: chemically synthesized

<400> SEQUENCE: 124

Trp Tyr Gly Tyr Val His Ala Tyr Ser Ala Trp Tyr Tyr Ser Ser Ala
1               5                   10                  15

Gly Asp Tyr

<210> SEQ ID NO 125
<211> LENGTH: 10
<212> TYPE: PRT
<213> ORGANISM: Artificial Sequence
<220> FEATURE:
<223> OTHER INFORMATION: chemically synthesized

<400> SEQUENCE: 125

Ser Gly Gly Tyr Ala Tyr Gly Met Asp Tyr
1               5                   10

<210> SEQ ID NO 126
<211> LENGTH: 10
<212> TYPE: PRT
<213> ORGANISM: Artificial Sequence
<220> FEATURE:
<223> OTHER INFORMATION: chemically synthesized

<400> SEQUENCE: 126

Tyr Gly Trp Gly Val Val Gly Ile Asp Tyr
1               5                   10

<210> SEQ ID NO 127
<211> LENGTH: 19
<212> TYPE: PRT
<213> ORGANISM: Artificial Sequence
<220> FEATURE:
<223> OTHER INFORMATION: chemically synthesized

<400> SEQUENCE: 127

Ala Pro Tyr Trp Gly Tyr Gly Tyr Tyr Ser Trp Ala Tyr Gly Tyr Gly
1               5                   10                  15

Val Asp Tyr

<210> SEQ ID NO 128
<211> LENGTH: 10
<212> TYPE: PRT
<213> ORGANISM: Artificial Sequence
<220> FEATURE:
<223> OTHER INFORMATION: chemically synthesized

<400> SEQUENCE: 128

Val Trp Gly Tyr Gly Trp Gly Phe Asp Tyr
1               5                   10

<210> SEQ ID NO 129
<211> LENGTH: 15
<212> TYPE: PRT
<213> ORGANISM: Artificial Sequence
<220> FEATURE:
<223> OTHER INFORMATION: chemically synthesized

<400> SEQUENCE: 129

Tyr Gly Gly Gly Gly Tyr Trp Ala Tyr Val Ser Ser Leu Asp Tyr
1               5                   10                  15

<210> SEQ ID NO 130
<211> LENGTH: 12
<212> TYPE: PRT
<213> ORGANISM: Artificial Sequence
<220> FEATURE:
<223> OTHER INFORMATION: chemically synthesized

<400> SEQUENCE: 130

Tyr Trp Tyr Gly Ser Trp Ser Ser Ala Met Asp Tyr
1               5                   10

<210> SEQ ID NO 131
<211> LENGTH: 8
<212> TYPE: PRT
<213> ORGANISM: Artificial Sequence
<220> FEATURE:
<223> OTHER INFORMATION: chemically synthesized

<400> SEQUENCE: 131

Val His Gly Val Gly Leu Asp Tyr
1               5

<210> SEQ ID NO 132
<211> LENGTH: 5
<212> TYPE: PRT
<213> ORGANISM: Artificial Sequence
<220> FEATURE:
<223> OTHER INFORMATION: chemically synthesized

<400> SEQUENCE: 132

Tyr Gly Leu Asp Tyr
1               5

<210> SEQ ID NO 133
<211> LENGTH: 19
<212> TYPE: PRT
<213> ORGANISM: Artificial Sequence
<220> FEATURE:
<223> OTHER INFORMATION: chemically synthesized

<400> SEQUENCE: 133

Ala Tyr Pro Trp Gly Trp Ser Gly Trp Tyr Ser Trp Ala Tyr Val Tyr
1               5                   10                  15

Phe Asp Tyr

<210> SEQ ID NO 134
<211> LENGTH: 12
<212> TYPE: PRT
<213> ORGANISM: Artificial Sequence
<220> FEATURE:
<223> OTHER INFORMATION: chemically synthesized

<400> SEQUENCE: 134

Ser Tyr Gly Trp Ala Trp Ser Pro Ala Phe Asp Tyr
1               5                   10

<210> SEQ ID NO 135
<211> LENGTH: 19
<212> TYPE: PRT
<213> ORGANISM: Artificial Sequence
<220> FEATURE:
<223> OTHER INFORMATION: chemically synthesized

<400> SEQUENCE: 135

```
Ser Ala Trp Trp Ser Trp Val Phe Pro Tyr Ser Tyr Ala Ser Gly
1               5                   10                  15

Met Asp Tyr

<210> SEQ ID NO 136
<211> LENGTH: 14
<212> TYPE: PRT
<213> ORGANISM: Artificial Sequence
<220> FEATURE:
<223> OTHER INFORMATION: chemically synthesized

<400> SEQUENCE: 136

Tyr Ser Tyr Ser Ala Ser Ala Trp Pro Gly Ala Met Asp Tyr
1               5                   10

<210> SEQ ID NO 137
<211> LENGTH: 6
<212> TYPE: PRT
<213> ORGANISM: Artificial Sequence
<220> FEATURE:
<223> OTHER INFORMATION: chemically synthesized

<400> SEQUENCE: 137

Gly Val Trp Ser Leu Ile
1               5

<210> SEQ ID NO 138
<211> LENGTH: 14
<212> TYPE: PRT
<213> ORGANISM: Artificial Sequence
<220> FEATURE:
<223> OTHER INFORMATION: chemically synthesized

<400> SEQUENCE: 138

His Ser Ser Ser Gly Tyr Gly His Tyr Ala Val Tyr Gly Ile
1               5                   10

<210> SEQ ID NO 139
<211> LENGTH: 8
<212> TYPE: PRT
<213> ORGANISM: Artificial Sequence
<220> FEATURE:
<223> OTHER INFORMATION: chemically synthesized

<400> SEQUENCE: 139

Ser Tyr Tyr Gly Trp Phe Leu Phe
1               5

<210> SEQ ID NO 140
<211> LENGTH: 14
<212> TYPE: PRT
<213> ORGANISM: Artificial Sequence
<220> FEATURE:
<223> OTHER INFORMATION: chemically synthesized

<400> SEQUENCE: 140

His Ala Ser Ser Gly Tyr Gly His Tyr Ala Val Tyr Gly Ile
1               5                   10

<210> SEQ ID NO 141
<211> LENGTH: 6
<212> TYPE: PRT
<213> ORGANISM: Artificial Sequence
<220> FEATURE:
<223> OTHER INFORMATION: chemically synthesized
```

<400> SEQUENCE: 141

Gly Val Trp Ser Leu Ile
1               5

<210> SEQ ID NO 142
<211> LENGTH: 14
<212> TYPE: PRT
<213> ORGANISM: Artificial Sequence
<220> FEATURE:
<223> OTHER INFORMATION: chemically synthesized

<400> SEQUENCE: 142

His Ala Ser Ser Gly Tyr Gly His Tyr Ala Val Tyr Gly Val
1               5                   10

<210> SEQ ID NO 143
<211> LENGTH: 6
<212> TYPE: PRT
<213> ORGANISM: Artificial Sequence
<220> FEATURE:
<223> OTHER INFORMATION: chemically synthesized

<400> SEQUENCE: 143

Gly Val Trp Ser Leu Ile
1               5

<210> SEQ ID NO 144
<211> LENGTH: 14
<212> TYPE: PRT
<213> ORGANISM: Artificial Sequence
<220> FEATURE:
<223> OTHER INFORMATION: chemically synthesized

<400> SEQUENCE: 144

Val Ser Tyr Tyr Ala Trp Phe Ser Ser Gly Tyr Ser Gly Phe
1               5                   10

<210> SEQ ID NO 145
<211> LENGTH: 6
<212> TYPE: PRT
<213> ORGANISM: Artificial Sequence
<220> FEATURE:
<223> OTHER INFORMATION: chemically synthesized

<400> SEQUENCE: 145

Ala Tyr Pro Tyr Leu Ile
1               5

<210> SEQ ID NO 146
<211> LENGTH: 11
<212> TYPE: PRT
<213> ORGANISM: Artificial Sequence
<220> FEATURE:
<223> OTHER INFORMATION: chemically synthesized

<400> SEQUENCE: 146

Phe Tyr Tyr Phe Ser Tyr Ser Ala Ser Gly Leu
1               5                   10

<210> SEQ ID NO 147
<211> LENGTH: 6
<212> TYPE: PRT
<213> ORGANISM: Artificial Sequence
<220> FEATURE:
<223> OTHER INFORMATION: chemically synthesized

<400> SEQUENCE: 147

```
Gly Val Trp Ser Leu Ile
1               5

<210> SEQ ID NO 148
<211> LENGTH: 14
<212> TYPE: PRT
<213> ORGANISM: Artificial Sequence
<220> FEATURE:
<223> OTHER INFORMATION: chemically synthesized

<400> SEQUENCE: 148

His Val Ser Ser Gly Tyr Gly His Tyr Ala Val Tyr Gly Ile
1               5                   10

<210> SEQ ID NO 149
<211> LENGTH: 5
<212> TYPE: PRT
<213> ORGANISM: Artificial Sequence
<220> FEATURE:
<223> OTHER INFORMATION: chemically synthesized

<400> SEQUENCE: 149

Ser Tyr Ala Leu Ile
1               5

<210> SEQ ID NO 150
<211> LENGTH: 14
<212> TYPE: PRT
<213> ORGANISM: Artificial Sequence
<220> FEATURE:
<223> OTHER INFORMATION: chemically synthesized

<400> SEQUENCE: 150

His Ala Ser Ser Gly Tyr Gly His Tyr Ala Val Tyr Gly Ile
1               5                   10

<210> SEQ ID NO 151
<211> LENGTH: 6
<212> TYPE: PRT
<213> ORGANISM: Artificial Sequence
<220> FEATURE:
<223> OTHER INFORMATION: chemically synthesized

<400> SEQUENCE: 151

Gly Val Trp Ser Leu Ile
1               5

<210> SEQ ID NO 152
<211> LENGTH: 14
<212> TYPE: PRT
<213> ORGANISM: Artificial Sequence
<220> FEATURE:
<223> OTHER INFORMATION: chemically synthesized

<400> SEQUENCE: 152

His Ala Phe Ser Gly Tyr Gly His Tyr Ala Val Tyr Gly Ile
1               5                   10

<210> SEQ ID NO 153
<211> LENGTH: 6
<212> TYPE: PRT
<213> ORGANISM: Artificial Sequence
<220> FEATURE:
<223> OTHER INFORMATION: chemically synthesized

<400> SEQUENCE: 153
```

Gly Val Trp Ser Leu Ile
1               5

<210> SEQ ID NO 154
<211> LENGTH: 14
<212> TYPE: PRT
<213> ORGANISM: Artificial Sequence
<220> FEATURE:
<223> OTHER INFORMATION: chemically synthesized

<400> SEQUENCE: 154

His Ala Ser Ser Val Tyr Gly His Tyr Ala Val Tyr Gly Ile
1               5                   10

<210> SEQ ID NO 155
<211> LENGTH: 6
<212> TYPE: PRT
<213> ORGANISM: Artificial Sequence
<220> FEATURE:
<223> OTHER INFORMATION: chemically synthesized

<400> SEQUENCE: 155

Gly Val Trp Ser Leu Ile
1               5

<210> SEQ ID NO 156
<211> LENGTH: 14
<212> TYPE: PRT
<213> ORGANISM: Artificial Sequence
<220> FEATURE:
<223> OTHER INFORMATION: chemically synthesized

<400> SEQUENCE: 156

His Ala Ser Ser Gly Tyr Gly His Tyr Ala Val Tyr Ala Ile
1               5                   10

<210> SEQ ID NO 157
<211> LENGTH: 6
<212> TYPE: PRT
<213> ORGANISM: Artificial Sequence
<220> FEATURE:
<223> OTHER INFORMATION: chemically synthesized

<400> SEQUENCE: 157

Gly Val Trp Ser Leu Ile
1               5

<210> SEQ ID NO 158
<211> LENGTH: 10
<212> TYPE: PRT
<213> ORGANISM: Artificial Sequence
<220> FEATURE:
<223> OTHER INFORMATION: chemically synthesized

<400> SEQUENCE: 158

Tyr Trp His Tyr Tyr Ser Tyr Ser Ala Leu
1               5                   10

<210> SEQ ID NO 159
<211> LENGTH: 8
<212> TYPE: PRT
<213> ORGANISM: Artificial Sequence
<220> FEATURE:
<223> OTHER INFORMATION: chemically synthesized

<400> SEQUENCE: 159

Val Gly Tyr Ser Tyr Ser Leu Ile

```
1               5

<210> SEQ ID NO 160
<211> LENGTH: 9
<212> TYPE: PRT
<213> ORGANISM: Artificial Sequence
<220> FEATURE:
<223> OTHER INFORMATION: chemically synthesized

<400> SEQUENCE: 160

Ser Tyr Tyr Ala Ser Gly Tyr Gly Leu
1               5

<210> SEQ ID NO 161
<211> LENGTH: 6
<212> TYPE: PRT
<213> ORGANISM: Artificial Sequence
<220> FEATURE:
<223> OTHER INFORMATION: chemically synthesized

<400> SEQUENCE: 161

Ser Phe Tyr Gly Leu Phe
1               5

<210> SEQ ID NO 162
<211> LENGTH: 7
<212> TYPE: PRT
<213> ORGANISM: Artificial Sequence
<220> FEATURE:
<223> OTHER INFORMATION: chemically synthesized

<400> SEQUENCE: 162

Gly Gly Tyr Pro Tyr Gly Met
1               5

<210> SEQ ID NO 163
<211> LENGTH: 5
<212> TYPE: PRT
<213> ORGANISM: Artificial Sequence
<220> FEATURE:
<223> OTHER INFORMATION: chemically synthesized

<400> SEQUENCE: 163

Pro Tyr Trp Leu Met
1               5

<210> SEQ ID NO 164
<211> LENGTH: 8
<212> TYPE: PRT
<213> ORGANISM: Artificial Sequence
<220> FEATURE:
<223> OTHER INFORMATION: chemically synthesized

<400> SEQUENCE: 164

Trp Ser His Tyr Tyr Gly Ala Met
1               5

<210> SEQ ID NO 165
<211> LENGTH: 6
<212> TYPE: PRT
<213> ORGANISM: Artificial Sequence
<220> FEATURE:
<223> OTHER INFORMATION: chemically synthesized

<400> SEQUENCE: 165

Ser Pro Ala Ala Leu Ile
1               5
```

```
<210> SEQ ID NO 166
<211> LENGTH: 14
<212> TYPE: PRT
<213> ORGANISM: Artificial Sequence
<220> FEATURE:
<223> OTHER INFORMATION: chemically synthesized

<400> SEQUENCE: 166

Gly Gly Trp Tyr Trp Trp His Tyr Gly Trp Ser Gly Ala Leu
1               5                   10

<210> SEQ ID NO 167
<211> LENGTH: 5
<212> TYPE: PRT
<213> ORGANISM: Artificial Sequence
<220> FEATURE:
<223> OTHER INFORMATION: chemically synthesized

<400> SEQUENCE: 167

Tyr Gly Tyr Pro Phe
1               5

<210> SEQ ID NO 168
<211> LENGTH: 6
<212> TYPE: PRT
<213> ORGANISM: Artificial Sequence
<220> FEATURE:
<223> OTHER INFORMATION: chemically synthesized

<400> SEQUENCE: 168

Gly Tyr His Ser Ala Met
1               5

<210> SEQ ID NO 169
<211> LENGTH: 9
<212> TYPE: PRT
<213> ORGANISM: Artificial Sequence
<220> FEATURE:
<223> OTHER INFORMATION: chemically synthesized

<400> SEQUENCE: 169

Tyr Ala Tyr Val His Pro Trp Pro Ile
1               5

<210> SEQ ID NO 170
<211> LENGTH: 12
<212> TYPE: PRT
<213> ORGANISM: Artificial Sequence
<220> FEATURE:
<223> OTHER INFORMATION: chemically synthesized

<400> SEQUENCE: 170

Pro Tyr Phe Tyr Pro Val Ala Gly Pro Ser Ala Leu
1               5                   10

<210> SEQ ID NO 171
<211> LENGTH: 8
<212> TYPE: PRT
<213> ORGANISM: Artificial Sequence
<220> FEATURE:
<223> OTHER INFORMATION: chemically synthesized

<400> SEQUENCE: 171

Tyr His Val Tyr Ser Ser Leu Phe
1               5
```

<210> SEQ ID NO 172
<211> LENGTH: 17
<212> TYPE: PRT
<213> ORGANISM: Artificial Sequence
<220> FEATURE:
<223> OTHER INFORMATION: chemically synthesized

<400> SEQUENCE: 172

Val Tyr Trp His Gly His Trp Ser Trp Trp Gly Gly Tyr Ala Pro Ala
1               5                   10                  15
Met

<210> SEQ ID NO 173
<211> LENGTH: 6
<212> TYPE: PRT
<213> ORGANISM: Artificial Sequence
<220> FEATURE:
<223> OTHER INFORMATION: chemically synthesized

<400> SEQUENCE: 173

Ser Ser Tyr Ser Leu Ile
1               5

<210> SEQ ID NO 174
<211> LENGTH: 12
<212> TYPE: PRT
<213> ORGANISM: Artificial Sequence
<220> FEATURE:
<223> OTHER INFORMATION: chemically synthesized

<400> SEQUENCE: 174

Trp Ser Tyr Ser Ser Tyr Ala Phe Tyr Ala Ala Ile
1               5                   10

<210> SEQ ID NO 175
<211> LENGTH: 7
<212> TYPE: PRT
<213> ORGANISM: Artificial Sequence
<220> FEATURE:
<223> OTHER INFORMATION: chemically synthesized

<400> SEQUENCE: 175

Tyr Tyr Tyr Ser Ser Pro Ile
1               5

<210> SEQ ID NO 176
<211> LENGTH: 14
<212> TYPE: PRT
<213> ORGANISM: Artificial Sequence
<220> FEATURE:
<223> OTHER INFORMATION: chemically synthesized

<400> SEQUENCE: 176

Ser Ser Ser Val Tyr Ala Tyr Trp Gly His Tyr Tyr Gly Met
1               5                   10

<210> SEQ ID NO 177
<211> LENGTH: 5
<212> TYPE: PRT
<213> ORGANISM: Artificial Sequence
<220> FEATURE:
<223> OTHER INFORMATION: chemically synthesized

<400> SEQUENCE: 177

Tyr Gly Tyr Pro Ile
1               5

```
<210> SEQ ID NO 178
<211> LENGTH: 17
<212> TYPE: PRT
<213> ORGANISM: Artificial Sequence
<220> FEATURE:
<223> OTHER INFORMATION: chemically synthesized

<400> SEQUENCE: 178

Gly Pro Gly Val His Tyr Tyr Ser Tyr Tyr His Ser Ser Trp Pro Ala
1               5                   10                  15

Met

<210> SEQ ID NO 179
<211> LENGTH: 8
<212> TYPE: PRT
<213> ORGANISM: Artificial Sequence
<220> FEATURE:
<223> OTHER INFORMATION: chemically synthesized

<400> SEQUENCE: 179

Trp Gly Gly Tyr Ser Ser Leu Ile
1               5

<210> SEQ ID NO 180
<211> LENGTH: 11
<212> TYPE: PRT
<213> ORGANISM: Artificial Sequence
<220> FEATURE:
<223> OTHER INFORMATION: chemically synthesized

<400> SEQUENCE: 180

Gly Ala Ser Tyr Tyr Trp Trp Tyr Pro Gly Met
1               5                   10

<210> SEQ ID NO 181
<211> LENGTH: 9
<212> TYPE: PRT
<213> ORGANISM: Artificial Sequence
<220> FEATURE:
<223> OTHER INFORMATION: chemically synthesized

<400> SEQUENCE: 181

Ser Tyr Trp Tyr Tyr Ala Tyr Pro Ile
1               5

<210> SEQ ID NO 182
<211> LENGTH: 11
<212> TYPE: PRT
<213> ORGANISM: Artificial Sequence
<220> FEATURE:
<223> OTHER INFORMATION: chemically synthesized

<400> SEQUENCE: 182

Tyr Gly Gly Pro Ser Pro Gly Trp Trp Ala Leu
1               5                   10

<210> SEQ ID NO 183
<211> LENGTH: 6
<212> TYPE: PRT
<213> ORGANISM: Artificial Sequence
<220> FEATURE:
<223> OTHER INFORMATION: chemically synthesized

<400> SEQUENCE: 183

Tyr Gly Tyr Tyr Pro Ile
```

```
1               5
```

<210> SEQ ID NO 184
<211> LENGTH: 3
<212> TYPE: PRT
<213> ORGANISM: Artificial Sequence
<220> FEATURE:
<223> OTHER INFORMATION: chemically synthesized

<400> SEQUENCE: 184

```
Gly Ala Leu
1
```

<210> SEQ ID NO 185
<211> LENGTH: 6
<212> TYPE: PRT
<213> ORGANISM: Artificial Sequence
<220> FEATURE:
<223> OTHER INFORMATION: chemically synthesized

<400> SEQUENCE: 185

```
Tyr Ala Tyr Tyr Pro Ile
1               5
```

<210> SEQ ID NO 186
<211> LENGTH: 3
<212> TYPE: PRT
<213> ORGANISM: Artificial Sequence
<220> FEATURE:
<223> OTHER INFORMATION: chemically synthesized

<400> SEQUENCE: 186

```
Gly Ala Leu
1
```

<210> SEQ ID NO 187
<211> LENGTH: 7
<212> TYPE: PRT
<213> ORGANISM: Artificial Sequence
<220> FEATURE:
<223> OTHER INFORMATION: chemically synthesized

<400> SEQUENCE: 187

```
Ser Tyr Ser Val Ala Pro Ile
1               5
```

<210> SEQ ID NO 188
<211> LENGTH: 3
<212> TYPE: PRT
<213> ORGANISM: Artificial Sequence
<220> FEATURE:
<223> OTHER INFORMATION: chemically synthesized

<400> SEQUENCE: 188

```
Gly Ala Leu
1
```

<210> SEQ ID NO 189
<211> LENGTH: 5
<212> TYPE: PRT
<213> ORGANISM: Artificial Sequence
<220> FEATURE:
<223> OTHER INFORMATION: chemically synthesized

<400> SEQUENCE: 189

```
Trp Ser Val Pro Ile
1               5
```

<210> SEQ ID NO 190
<211> LENGTH: 10
<212> TYPE: PRT
<213> ORGANISM: Artificial Sequence
<220> FEATURE:
<223> OTHER INFORMATION: chemically synthesized

<400> SEQUENCE: 190

Tyr Ser Ala Gly Gly Val Trp Phe Ala Phe
1               5                   10

<210> SEQ ID NO 191
<211> LENGTH: 5
<212> TYPE: PRT
<213> ORGANISM: Artificial Sequence
<220> FEATURE:
<223> OTHER INFORMATION: chemically synthesized

<400> SEQUENCE: 191

Trp Ser Val Pro Ile
1               5

<210> SEQ ID NO 192
<211> LENGTH: 10
<212> TYPE: PRT
<213> ORGANISM: Artificial Sequence
<220> FEATURE:
<223> OTHER INFORMATION: chemically synthesized

<400> SEQUENCE: 192

Tyr Ser Ala Gly Gly Gly Trp Phe Ala Phe
1               5                   10

<210> SEQ ID NO 193
<211> LENGTH: 7
<212> TYPE: PRT
<213> ORGANISM: Artificial Sequence
<220> FEATURE:
<223> OTHER INFORMATION: chemically synthesized

<400> SEQUENCE: 193

Tyr Val Trp Tyr Ser Leu Phe
1               5

<210> SEQ ID NO 194
<211> LENGTH: 10
<212> TYPE: PRT
<213> ORGANISM: Artificial Sequence
<220> FEATURE:
<223> OTHER INFORMATION: chemically synthesized

<400> SEQUENCE: 194

Tyr Ser Ala Gly Gly Val Trp Phe Ala Phe
1               5                   10

<210> SEQ ID NO 195
<211> LENGTH: 7
<212> TYPE: PRT
<213> ORGANISM: Artificial Sequence
<220> FEATURE:
<223> OTHER INFORMATION: chemically synthesized

<400> SEQUENCE: 195

Tyr Val Trp Tyr Ser Leu Phe
1               5

```
<210> SEQ ID NO 196
<211> LENGTH: 9
<212> TYPE: PRT
<213> ORGANISM: Artificial Sequence
<220> FEATURE:
<223> OTHER INFORMATION: chemically synthesized

<400> SEQUENCE: 196

Gly His Tyr Gly Tyr Phe Gly Gly Leu
1               5

<210> SEQ ID NO 197
<211> LENGTH: 9
<212> TYPE: PRT
<213> ORGANISM: Artificial Sequence
<220> FEATURE:
<223> OTHER INFORMATION: chemically synthesized

<400> SEQUENCE: 197

Ser Trp Gly Tyr Pro Val His Leu Ile
1               5

<210> SEQ ID NO 198
<211> LENGTH: 4
<212> TYPE: PRT
<213> ORGANISM: Artificial Sequence
<220> FEATURE:
<223> OTHER INFORMATION: chemically synthesized

<400> SEQUENCE: 198

Ser Tyr Gly Leu
1

<210> SEQ ID NO 199
<211> LENGTH: 5
<212> TYPE: PRT
<213> ORGANISM: Artificial Sequence
<220> FEATURE:
<223> OTHER INFORMATION: chemically synthesized

<400> SEQUENCE: 199

Ala Tyr Tyr Pro Ile
1               5

<210> SEQ ID NO 200
<211> LENGTH: 5
<212> TYPE: PRT
<213> ORGANISM: Artificial Sequence
<220> FEATURE:
<223> OTHER INFORMATION: chemically synthesized

<400> SEQUENCE: 200

Tyr Ala His Gly Met
1               5

<210> SEQ ID NO 201
<211> LENGTH: 9
<212> TYPE: PRT
<213> ORGANISM: Artificial Sequence
<220> FEATURE:
<223> OTHER INFORMATION: chemically synthesized

<400> SEQUENCE: 201

Tyr Tyr Gly Ser Tyr Ala Ser Pro Phe
1               5
```

```
<210> SEQ ID NO 202
<211> LENGTH: 6
<212> TYPE: PRT
<213> ORGANISM: Artificial Sequence
<220> FEATURE:
<223> OTHER INFORMATION: chemically synthesized

<400> SEQUENCE: 202

Gly Gly Gly Trp Ala Leu
1               5

<210> SEQ ID NO 203
<211> LENGTH: 5
<212> TYPE: PRT
<213> ORGANISM: Artificial Sequence
<220> FEATURE:
<223> OTHER INFORMATION: chemically synthesized

<400> SEQUENCE: 203

Tyr Ser Trp Leu Ile
1               5

<210> SEQ ID NO 204
<211> LENGTH: 8
<212> TYPE: PRT
<213> ORGANISM: Artificial Sequence
<220> FEATURE:
<223> OTHER INFORMATION: chemically synthesized

<400> SEQUENCE: 204

Gly Trp Gly Tyr Trp Tyr Gly Phe
1               5

<210> SEQ ID NO 205
<211> LENGTH: 5
<212> TYPE: PRT
<213> ORGANISM: Artificial Sequence
<220> FEATURE:
<223> OTHER INFORMATION: chemically synthesized

<400> SEQUENCE: 205

Tyr Trp Val Pro Ile
1               5

<210> SEQ ID NO 206
<211> LENGTH: 4
<212> TYPE: PRT
<213> ORGANISM: Artificial Sequence
<220> FEATURE:
<223> OTHER INFORMATION: chemically synthesized

<400> SEQUENCE: 206

Gly Val Gly Leu
1

<210> SEQ ID NO 207
<211> LENGTH: 6
<212> TYPE: PRT
<213> ORGANISM: Artificial Sequence
<220> FEATURE:
<223> OTHER INFORMATION: chemically synthesized

<400> SEQUENCE: 207

Tyr Ala Ala His Leu Ile
1               5

<210> SEQ ID NO 208
```

```
<211> LENGTH: 3
<212> TYPE: PRT
<213> ORGANISM: Artificial Sequence
<220> FEATURE:
<223> OTHER INFORMATION: chemically synthesized

<400> SEQUENCE: 208

Ser Ala Met
1

<210> SEQ ID NO 209
<211> LENGTH: 6
<212> TYPE: PRT
<213> ORGANISM: Artificial Sequence
<220> FEATURE:
<223> OTHER INFORMATION: chemically synthesized

<400> SEQUENCE: 209

Tyr Trp Gly Ser Leu Ile
1               5

<210> SEQ ID NO 210
<211> LENGTH: 3
<212> TYPE: PRT
<213> ORGANISM: Artificial Sequence
<220> FEATURE:
<223> OTHER INFORMATION: chemically synthesized

<400> SEQUENCE: 210

Ser Ala Met
1

<210> SEQ ID NO 211
<211> LENGTH: 6
<212> TYPE: PRT
<213> ORGANISM: Artificial Sequence
<220> FEATURE:
<223> OTHER INFORMATION: chemically synthesized

<400> SEQUENCE: 211

Ser Ser Tyr Ser Leu Ile
1               5

<210> SEQ ID NO 212
<211> LENGTH: 5
<212> TYPE: PRT
<213> ORGANISM: Artificial Sequence
<220> FEATURE:
<223> OTHER INFORMATION: chemically synthesized

<400> SEQUENCE: 212

Tyr Ser Tyr Ala Phe
1               5

<210> SEQ ID NO 213
<211> LENGTH: 5
<212> TYPE: PRT
<213> ORGANISM: Artificial Sequence
<220> FEATURE:
<223> OTHER INFORMATION: chemically synthesized

<400> SEQUENCE: 213

Tyr Ser Trp Leu Ile
1               5

<210> SEQ ID NO 214
<211> LENGTH: 8
```

```
<212> TYPE: PRT
<213> ORGANISM: Artificial Sequence
<220> FEATURE:
<223> OTHER INFORMATION: chemically synthesized

<400> SEQUENCE: 214

Tyr Ser Gly Val Ser Tyr Gly Met
1               5

<210> SEQ ID NO 215
<211> LENGTH: 6
<212> TYPE: PRT
<213> ORGANISM: Artificial Sequence
<220> FEATURE:
<223> OTHER INFORMATION: chemically synthesized

<400> SEQUENCE: 215

Tyr Tyr Gly Ser His Tyr
1               5

<210> SEQ ID NO 216
<211> LENGTH: 10
<212> TYPE: PRT
<213> ORGANISM: Artificial Sequence
<220> FEATURE:
<223> OTHER INFORMATION: chemically synthesized

<400> SEQUENCE: 216

Gly Ala Trp Ser Phe Val Tyr Gly Gly Met
1               5                   10

<210> SEQ ID NO 217
<211> LENGTH: 6
<212> TYPE: PRT
<213> ORGANISM: Artificial Sequence
<220> FEATURE:
<223> OTHER INFORMATION: chemically synthesized

<400> SEQUENCE: 217

Tyr Tyr Gly Ser His Tyr
1               5

<210> SEQ ID NO 218
<211> LENGTH: 5
<212> TYPE: PRT
<213> ORGANISM: Artificial Sequence
<220> FEATURE:
<223> OTHER INFORMATION: chemically synthesized

<400> SEQUENCE: 218

Ser Gly Tyr Gly Leu
1               5

<210> SEQ ID NO 219
<211> LENGTH: 6
<212> TYPE: PRT
<213> ORGANISM: Artificial Sequence
<220> FEATURE:
<223> OTHER INFORMATION: chemically synthesized

<400> SEQUENCE: 219

Ser Ser Tyr Ser Leu Ile
1               5

<210> SEQ ID NO 220
<211> LENGTH: 10
<212> TYPE: PRT
```

<210> SEQ ID NO 220
<211> LENGTH: 10 (implied)
<212> TYPE: PRT
<213> ORGANISM: Artificial Sequence
<220> FEATURE:
<223> OTHER INFORMATION: chemically synthesized

<400> SEQUENCE: 220

Ser Trp Ser Trp Ala Ala Ala Ser Gly Met
1               5                   10

<210> SEQ ID NO 221
<211> LENGTH: 6
<212> TYPE: PRT
<213> ORGANISM: Artificial Sequence
<220> FEATURE:
<223> OTHER INFORMATION: chemically synthesized

<400> SEQUENCE: 221

Tyr Tyr Gly Ala Leu Phe
1               5

<210> SEQ ID NO 222
<211> LENGTH: 10
<212> TYPE: PRT
<213> ORGANISM: Artificial Sequence
<220> FEATURE:
<223> OTHER INFORMATION: chemically synthesized

<400> SEQUENCE: 222

Tyr Trp His Gly Ser Tyr Ala Ala Gly Met
1               5                   10

<210> SEQ ID NO 223
<211> LENGTH: 25
<212> TYPE: DNA
<213> ORGANISM: Artificial Sequence
<220> FEATURE:
<223> OTHER INFORMATION: chemically synthesized

<400> SEQUENCE: 223
aatgatacgg cgaccaccga gatct                                      25

<210> SEQ ID NO 224
<211> LENGTH: 35
<212> TYPE: DNA
<213> ORGANISM: Artificial Sequence
<220> FEATURE:
<223> OTHER INFORMATION: chemically synthesized

<400> SEQUENCE: 224
gcagccggaa gacttcgcaa cttattactg tcagc                           35

<210> SEQ ID NO 225
<211> LENGTH: 24
<212> TYPE: DNA
<213> ORGANISM: Artificial Sequence
<220> FEATURE:
<223> OTHER INFORMATION: chemically synthesized

<400> SEQUENCE: 225
caagcagaag acggcatacg agat                                       24

<210> SEQ ID NO 226
<211> LENGTH: 5
<212> TYPE: DNA
<213> ORGANISM: Artificial Sequence
<220> FEATURE:
<223> OTHER INFORMATION: chemically synthesized
<220> FEATURE:

<220> FEATURE:
<221> NAME/KEY: misc_feature
<222> LOCATION: (1)..(5)
<223> OTHER INFORMATION: n is a, t, c or g

<400> SEQUENCE: 226 nnnnn                                                                   5

<210> SEQ ID NO 227
<211> LENGTH: 30
<212> TYPE: DNA
<213> ORGANISM: Artificial Sequence
<220> FEATURE:
<223> OTHER INFORMATION: chemically synthesized

<400> SEQUENCE: 227
ggtgaccagg gttccttgac cccagtagtc                                       30

<210> SEQ ID NO 228
<211> LENGTH: 36
<212> TYPE: DNA
<213> ORGANISM: Artificial Sequence
<220> FEATURE:
<223> OTHER INFORMATION: chemically synthesized

<400> SEQUENCE: 228
cagccggaag acttcgcaac ttattactgt cagcaa                                36

<210> SEQ ID NO 229
<211> LENGTH: 30
<212> TYPE: DNA
<213> ORGANISM: Artificial Sequence
<220> FEATURE:
<223> OTHER INFORMATION: chemically synthesized

<400> SEQUENCE: 229
gactactggg gtcaaggaac cctggtcacc                                       30

<210> SEQ ID NO 230
<211> LENGTH: 30
<212> TYPE: DNA
<213> ORGANISM: Artificial Sequence
<220> FEATURE:
<223> OTHER INFORMATION: chemically synthesized

<400> SEQUENCE: 230
ggtgaccagg gttccttgac cccagtagtc                                       30

<210> SEQ ID NO 231
<211> LENGTH: 58
<212> TYPE: DNA
<213> ORGANISM: Artificial Sequence
<220> FEATURE:
<223> OTHER INFORMATION: chemically synthesized

<400> SEQUENCE: 231
aatgatacgg cgaccaccga gatctacact ctttccctac acgacgctct tccgatct       58

<210> SEQ ID NO 232
<211> LENGTH: 8
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (1)..(8)
<223> OTHER INFORMATION: n is a, t, c or g

<400> SEQUENCE: 232 nnnnnnnn                                                                8

<210> SEQ ID NO 233
<211> LENGTH: 30
<212> TYPE: DNA
<213> ORGANISM: Artificial Sequence
<220> FEATURE:
<223> OTHER INFORMATION: chemically synthesized

<400> SEQUENCE: 233
ggtgaccagg gttccttgac cccagtagtc                                       30

<210> SEQ ID NO 234
<211> LENGTH: 37
<212> TYPE: DNA
<213> ORGANISM: Artificial Sequence
<220> FEATURE:
<223> OTHER INFORMATION: chemically synthesized

<400> SEQUENCE: 234
cggtctcggc attcctgctg aaccgctctt ccgatct                               37

<210> SEQ ID NO 235
<211> LENGTH: 36
<212> TYPE: DNA
<213> ORGANISM: Artificial Sequence
<220> FEATURE:
<223> OTHER INFORMATION: chemically synthesized

<400> SEQUENCE: 235
cagccggaag acttcgcaac ttattactgt cagcaa                                36

<210> SEQ ID NO 236
<211> LENGTH: 30
<212> TYPE: DNA
<213> ORGANISM: Artificial Sequence
<220> FEATURE:
<223> OTHER INFORMATION: chemically synthesized

<400> SEQUENCE: 236
ccatctcatc cctgcgtgtc tccgactcag                                       30

<210> SEQ ID NO 237
<211> LENGTH: 20
<212> TYPE: DNA
<213> ORGANISM: Artificial Sequence
<220> FEATURE:
<223> OTHER INFORMATION: chemically synthesized

<400> SEQUENCE: 237
aggacactgc cgtctattat                                                  20

<210> SEQ ID NO 238
<211> LENGTH: 23
<212> TYPE: DNA
<213> ORGANISM: Artificial Sequence
<220> FEATURE:
<223> OTHER INFORMATION: chemically synthesized

<400> SEQUENCE: 238
cctctctatg ggcagtcggt gat                                              23

<210> SEQ ID NO 239

```
<211> LENGTH: 20
<212> TYPE: DNA
<213> ORGANISM: Artificial Sequence
<220> FEATURE:
<223> OTHER INFORMATION: chemically synthesized

<400> SEQUENCE: 239
aggacactgc cgtctattat                                                    20

<210> SEQ ID NO 240
<211> LENGTH: 5
<212> TYPE: PRT
<213> ORGANISM: Artificial Sequence
<220> FEATURE:
<223> OTHER INFORMATION: chemically synthesized

<400> SEQUENCE: 240

Ser Val Ser Ser Ala
1               5

<210> SEQ ID NO 241
<211> LENGTH: 7
<212> TYPE: PRT
<213> ORGANISM: Artificial Sequence
<220> FEATURE:
<223> OTHER INFORMATION: chemically synthesized

<400> SEQUENCE: 241

Ser Ala Ser Ser Leu Tyr Ser
1               5

<210> SEQ ID NO 242
<211> LENGTH: 6
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(4)
<223> OTHER INFORMATION: Xaa is Y, S, G, A, F, W, H, P or V
<220> FEATURE:
<221> NAME/KEY: MISC_FEATURE
<222> LOCATION: (5)..(5)
<223> OTHER INFORMATION: Xaa is P or L
<220> FEATURE:
<221> NAME/KEY: MISC_FEATURE
<222> LOCATION: (6)..(6)
<223> OTHER INFORMATION: Xaa is I or L

<400> SEQUENCE: 242

Xaa Xaa Xaa Xaa Xaa Xaa
1               5

<210> SEQ ID NO 243
<211> LENGTH: 6
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Xaa is I or L
<220> FEATURE:
<221> NAME/KEY: MISC_FEATURE
<222> LOCATION: (2)..(5)
<223> OTHER INFORMATION: Xaa is Y or S
<220> FEATURE:
<221> NAME/KEY: MISC_FEATURE
<222> LOCATION: (6)..(6)
```

```
<223> OTHER INFORMATION: Xaa is I or M

<400> SEQUENCE: 243

Xaa Xaa Xaa Xaa Xaa Xaa
1               5

<210> SEQ ID NO 244
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Xaa is Y or S
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa is Y or S
<220> FEATURE:
<221> NAME/KEY: MISC_FEATURE
<222> LOCATION: (5)..(5)
<223> OTHER INFORMATION: Xaa is P or S
<220> FEATURE:
<221> NAME/KEY: MISC_FEATURE
<222> LOCATION: (6)..(6)
<223> OTHER INFORMATION: Xaa is Y or S
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa is G or S
<220> FEATURE:
<221> NAME/KEY: MISC_FEATURE
<222> LOCATION: (9)..(9)
<223> OTHER INFORMATION: Xaa is Y or S
<220> FEATURE:
<221> NAME/KEY: MISC_FEATURE
<222> LOCATION: (11)..(11)
<223> OTHER INFORMATION: Xaa is Y or S

<400> SEQUENCE: 244

Xaa Ile Xaa Xaa Xaa Xaa Xaa Xaa Xaa Thr Xaa
1               5                   10

<210> SEQ ID NO 245
<211> LENGTH: 6
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (2)..(6)
<223> OTHER INFORMATION: Xaa is Y, S or, G

<400> SEQUENCE: 245

Gln Xaa Xaa Xaa Xaa Xaa
1               5

<210> SEQ ID NO 246
<211> LENGTH: 6
<212> TYPE: PRT
<213> ORGANISM: Artificial Sequence
<220> FEATURE:
```

<223> OTHER INFORMATION: chemically synthesized
<220> FEATURE:
<221> NAME/KEY: MISC_FEATURE
<222> LOCATION: (1)..(1)
<223> OTHER INFORMATION: Xaa is Y, S or G
<220> FEATURE:
<221> NAME/KEY: MISC_FEATURE
<222> LOCATION: (4)..(4)
<223> OTHER INFORMATION: Xaa is Y, S or G

<400> SEQUENCE: 246

Xaa Ala Ser Xaa Leu Tyr
1               5

<210> SEQ ID NO 247
<211> LENGTH: 6
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Xaa is I or L
<220> FEATURE:
<221> NAME/KEY: MISC_FEATURE
<222> LOCATION: (2)..(5)
<223> OTHER INFORMATION: Xaa is Y, S or G
<220> FEATURE:
<221> NAME/KEY: MISC_FEATURE
<222> LOCATION: (6)..(6)
<223> OTHER INFORMATION: Xaa is I or M

<400> SEQUENCE: 247

Xaa Xaa Xaa Xaa Xaa Xaa
1               5

<210> SEQ ID NO 248
<211> LENGTH: 5037
<212> TYPE: DNA
<213> ORGANISM: Artificial Sequence
<220> FEATURE:
<223> OTHER INFORMATION: chemically synthesized

<400> SEQUENCE: 248

| | | |
|---|---|---|
| ggaaattgta aacgttaata ttttgttaaa attcgcgtta aattttttgtt aaatcagctc | 60 |
| atttttttaac caataggccg aaatcggcaa atcccttat aaatcaaaag aatagaccga | 120 |
| gatagggttg agtgttgttc cagtttggaa caagagtcca ctattaaaga acgtggactc | 180 |
| caacgtcaaa gggcgaaaaa ccgtctatca gggcgatggc ccactacgtg aaccatcacc | 240 |
| ctaatcaagt tttttggggt cgaggtgccg taaagcacta aatcggaacc ctaaagggag | 300 |
| ccccgattt agagcttgac ggggaaagcc ggcgaacgtg gcgagaaagg aagggaagaa | 360 |
| agcgaaagga gcgggcgcta gggcgctggc aagtgtagcg gtcacgctgc gcgtaaccac | 420 |
| cacacccgcc gcgcttaatg cgccgctaca gggcgcgtcg cgccattcgc cattcaggct | 480 |
| gcgcaactgt tgggaagggc gatcggtgcg ggcctcttcg ctattacgcg catgcgacca | 540 |
| acagcggttg attgatcagg tagagggggc gctgtacgag gtaaagcccg atgccagcat | 600 |
| tcctgacgac gatacggagc tgctgcgcga ttacgtaaag aagttattga agcatcctcg | 660 |
| tcagtaaaaa gttaatcttt tcaacagctg tcataaagtt gtcacggccg agacttatag | 720 |
| tcgctttgtt tttatttttt aatgtatttg taactagtac gcaagttcac gtaaaaggg | 780 |
| tatgtagagg ttgaggtgat tttatgaaaa agaatatcgc atttcttctt gcatctatgt | 840 |
| tcgtttttc tattgctaca aatgcctatg catccgatat ccagatgacc cagtcccga | 900 |

```
gctccctgtc cgcctctgtg ggcgataggg tcaccatcac ctgccgtgcc agtcagtccg    960
tgtccagcgc tgtagcctgg tatcaacaga aaccaggaaa agctccgaag cttctgattt   1020
actcggcatc cagcctctac tctggagtcc cttctcgctt tctctggtagc cgttccggga   1080
cggatttcac tctgaccatc agcagtctgc agccggaaga cttcgcaact tattactgtc   1140
agcaatcttc ttattctctg atcacgttcg acagggtac caaggtggag atcaaacgaa   1200
ctgtggctgc accatctgtc ttcatcttcc cgccatctga ttcacagttg aaatctggaa   1260
ctgcctctgt tgtgtgcctg ctgaataact tctatcccag agaggccaaa gtacagtgga   1320
aggtggataa cgccctccaa tcgggtaact cccaggagag tgtcacagag caggacagca   1380
aggacagcac ctacagcctc agcagcaccc tgacgctgag caaagcagac tacgaaaaac   1440
ataaagtcta cgcctgcgaa gtcacccatc agggcctgag ctcgcccgtc acaaagagct   1500
tcaacagggg agagtgtggt ggttctgatt acaaagatga cgatgacaaa taattaactc   1560
gaggctgagc aaagcagact actaataaca taaagtctac gccggacgca tcgtggccct   1620
agtacgcaag ttcacgtaaa aagggtaact agaggttgag gtgatttat gaaaaagaat   1680
atcgcatttc ttcttgcatc tatgttcgtt ttttctattg ctacaaacgc gtacgctgag   1740
atctccgagg ttcagctggt ggagtctggc ggtggcctgg tgcagccagg gggctcactc   1800
cgtttgtcct gtgcagcttc tggcttcaac ttttcttctt cttctataca ctgggtgcgt   1860
caggccccgg gtaagggcct ggaatgggtt gcatctattt cttcttctta tggctatact   1920
tattatgccg atagcgtcaa gggccgtttc actataagcg cagacacatc caaaaacaca   1980
gcctacctac aaatgaacag cttaagagct gaggacactg ccgtctatta ttgtgctcgc   2040
actgttcgtg gatccaaaaa accgtacttc tctggttggg ctatggacta ctggggtcaa   2100
ggaaccctgg tcaccgtctc ctcggcctcc accaagggtc catcggtctt ccccctggca   2160
ccctcctcca agagcacctc tgggggcaca gcggccctgg gctgcctggt caaggactac   2220
ttccccgaac cggtgacggt gtcgtggaac tcaggcgccc tgaccagcgg cgtgcacacc   2280
ttcccggctg tcctacagtc ctcaggactc tactccctca gcagcgtggt gaccgtgccc   2340
tccagcagct gggcaccca gacctacatc tgcaacgtga atcacaagcc cagcaacacc   2400
aaggtcgaca gaaaagttga gcccaaatct tgtgacaaaa ctcacacatg cggccggccc   2460
tctggttccg gtgattttga ttatgaaaag atggcaaacg ctaataaggg ggctatgacc   2520
gaaaatgccg atgaaaacgc gctacagtct gacgctaaag gcaaacttga ttctgtcgct   2580
actgattacg gtgctgctat cgatggtttc attggtgacg tttccggcct tgctaatggt   2640
aatggtgcta ctggtgattt tgctggctct aattcccaaa tggctcaagt cggtgacggt   2700
gataattcac ctttaatgaa taatttccgt caatatttac cttccctccc tcaatcggtt   2760
gaatgtcgcc cttttgtctt tagcgctggt aaaccatatg aattttctat tgattgtgac   2820
aaaataaact tattccgtgg tgtctttgcg tttcttttat atgttgccac ctttatgtat   2880
gtatttttcta cgtttgctaa catactgcgt aataaggagt cttaaagctc caattcgccc   2940
tatagtgagt cgtattacaa ttcactggcc gtcgttttac aacgtcgtga ctgggaaaac   3000
cctggcgtta cccaacttaa tcgccttgca gcacatcccc ctttcgccag ctgcattaat   3060
gaatcggcca acgcgcgggg agaggcggtt tgcgtattgg gcgctcttcc gcttcctcgc   3120
tcactgactc gctgcgctcg gtcgttcggc tgcggcgagc ggtatcagct cactcaaagg   3180
cggtaatacg gttatccaca gaatcagggg ataacgcagg aaagaacatg tgagcaaaag   3240
```

-continued

```
gccagcaaaa ggccaggaac cgtaaaaagg ccgcgttgct ggcgtttttc cataggctcc    3300 gccccctga cgagcatcac aaaaatcgac gctcaagtca gaggtggcga acccgacag     3360 gactataaag ataccaggcg tttccccctg gaagctccct cgtgcgctct cctgttccga    3420
ccctgccgct taccggatac ctgtccgcct ttctcccttc gggaagcgtg gcgctttctc    3480
atagctcacg ctgtaggtat ctcagttcgg tgtaggtcgt tcgctccaag ctgggctgtg    3540
tgcacgaacc ccccgttcag cccgaccgct gcgccttatc cggtaactat cgtcttgagt    3600
ccaacccggt aagacacgac ttatcgccac tggcagcagc cactggtaac aggattagca    3660
gagcgaggta tgtaggcggt gctacagagt tcttgaagtg gtggcctaac tacggctaca    3720
ctagaaggac agtatttggt atctgcgctc tgctgaagcc agttaccttc ggaaaaagag    3780
ttggtagctc ttgatccggc aaacaaacca ccgctggtag cggtggtttt tttgtttgca    3840
agcagcagat tacgcgcaga aaaaaggat ctcaagaaga tcctttgatc ttttctacgg     3900
ggtctgacgc tcagtggaac gaaaactcac gttaagggat tttggtcatg agattatcaa    3960
aaaggatctt cacctagatc cttttaaatt aaaaatgaag ttttaaatca atctaaagta    4020
tatatgagta aacttggtct gacagttacc aatgcttaat cagtgaggca cctatctcag    4080
cgatctgtct atttcgttca tccatagttg cctgactccc cgtcgtgtag ataactacga    4140
tacgggaggg cttaccatct ggccccagtg ctgcaatgat accgcgagac ccacgctcac    4200
cggctccaga tttatcagca ataaaccagc cagccggaag ggccgagcgc agaagtggtc    4260
ctgcaacttt atccgcctcc atccagtcta ttaattgttg ccgggaagct agagtaagta    4320
gttcgccagt taatagtttg cgcaacgttg ttgccattgc tacaggcatc gtggtgtcac    4380
gctcgtcgtt tggtatggct tcattcagct ccggttccca acgatcaagg cgagttacat    4440
gatcccccat gttgtgcaaa aaagcggtta gctccttcgg tcctccgatc gttgtcagaa    4500
gtaagttggc cgcagtgtta tcactcatgg ttatggcagc actgcataat tctcttactg    4560
tcatgccatc cgtaagatgc ttttctgtga ctggtgagta ctcaaccaag tcattctgag    4620
aatagtgtat gcggcgaccg agttgctctt gcccggcgtc aatacgggat aataccgcgc    4680
cacatagcag aactttaaaa gtgctcatca ttggaaaacg ttcttcgggg cgaaaactct    4740
caaggatctt accgctgttg agatccagtt cgatgtaacc cactcgtgca cccaactgat    4800
cttcagcatc ttttactttc accagcgttt ctgggtgagc aaaaacagga aggcaaaatg    4860
ccgcaaaaaa gggaataagg gcgacacgga aatgttgaat actcatactc ttcctttttc    4920
aatattattg aagcatttat cagggttatt gtctcatgag cggatacata tttgaatgta    4980
tttagaaaaa taaacaaata ggggttccgc gcacatttcc ccgaaaagtg ccacctg      5037
```

<210> SEQ ID NO 249
<211> LENGTH: 6526
<212> TYPE: DNA
<213> ORGANISM: Artificial Sequence
<220> FEATURE:
<223> OTHER INFORMATION: chemically synthesized

<400> SEQUENCE: 249

```
gaattcccga caccatcgaa tggtgcaaaa cctttcgcgg tatggcatga tagcgcccgg     60
aagagagtca attcagggtg gtgaatgtga aaccagtaac gttatacgat gtcgcagagt    120
atgccggtgt ctcttatcag accgtttccc gcgtggtgaa ccaggccagc cacgtttctg    180
cgaaaacgcg ggaaaaagtg gaagcggcga tggcggagct gaattacatt cccaaccgcg    240
tggcacaaca actggcgggc aaacagtcgt tgctgattgg cgttgccacc tccagtctgg    300
```

```
ccctgcacgc gccgtcgcaa attgtcgcgg cgattaaatc tcgcgccgat caactgggtg      360
ccagcgtggt ggtgtcgatg gtagaacgaa gcggcgtcga agcctgtaaa gcggcggtgc      420
acaatcttct cgcgcaacgc gtcagtgggc tgatcattaa ctatccgctg atgaccagg       480 atgccattgc tgtggaagct gcctgcacta atgttccggc gttatttctt gatgtctctg      540
accagacacc catcaacagt attattttct cccatgaaga cggtacgcga ctgggcgtgg      600
agcatctggt cgcattgggt caccagcaaa tcgcgctgtt agcgggccca ttaagttctg      660
tctcggcgcg tctgcgtctg gctggctggc ataaatatct cactcgcaat caaattcagc      720
cgatagcgga acgggaaggc gactggagtg ccatgtccgg ttttcaacaa accatgcaaa      780
tgctgaatga gggcatcgtt cccactgcga tgctggttgc caacgatcag atggcgctgg      840
gcgcaatgcg cgccattacc gagtccgggc tgcgcgttgg tgcggatatc tcggtagtgg      900
gatacgacga taccgaagac agctcatgtt atatcccgcc gttaaccacc atcaaacagg      960
attttcgcct gctggggcaa accagcgtgg accgcttgct gcaactctct cagggccagg     1020
cggtgaaggg caatcagctg ttgcccgtct cactggtgaa agaaaaacc accctggcgc      1080 ccaatacgca aaccgcctct ccccgcgcgt tggccgattc attaatgcag ctggcacgac     1140
aggtttcccg actggaaagc gggcagtgag cgcaacgcaa ttaatgtgag ttagctcact     1200
cattaggcac aattctcatg tttgacagct tatcatcgac tgcacggtgc accaatgctt     1260
ctggcgtcag gcagccatcg gaagctgtgg tatggctgtg caggtcgtaa atcactgcat     1320
aattcgtgtc gctcaaggcg cactcccgtt ctggataatg tttttgcgc cgacatcata      1380 acggttctgg caaatattct gaaatgagct gttgacaatt aatcatcggc tcgtataatg     1440
tgtggaattg tgagcggata caatttcac acaggaaaca gccagtccgt ttaggtgttt      1500
tcacgagcac ttcaccaaca aggaccatag attatgaaaa agaatatcgc atttcttctt     1560
gcatctatgt tcgttttttc tattgctaca aatgcctatg catccgatta caaagatgac     1620
gatgacaaag gcggtggcga tatccagatg acccagtccc cgagctccct gtccgcctct     1680
gtgggcgata gggtcaccat cacctgccgt gccagtcagt ccgtgtccag cgctgtagcc     1740
tggtatcaac agaaaccagg aaaagctccg aagcttctga tttactcggc atccagcctc     1800
tactctggag tccttctcg cttctctggt agccgttccg ggacggattt cactctgacc      1860
atcagcagtc tgcagccgga agacttcgca acttattact gtcagcaatc ttcttattct     1920
ctgatcacgt tcggacaggg taccaaggtg gagatcaaag gtactactgc cgctagtggt     1980
agtagtggtg gcagtagcag tggtgccgag gttcagctgg tggagtctgg cggtggcctg     2040
gtgcagccag ggggctcact ccgtttgtcc tgtgcagctt ctggcttcaa ctttcttct      2100 tcttctatac actgggtgcg tcaggccccg ggtaagggcc tggaatgggt tgcatctatt     2160
tcttcttctt atggctatac ttattatgcc gatagcgtca agggccgttt cactataagc     2220
gcagacacat ccaaaaacac agcctaccta caaatgaaca gcttaagagc tgaggacact     2280
gccgtctatt attgtgctcg cactgttcgt ggatccaaaa accgtactt ctctggttgg      2340 gctatggact actggggtca aggaaccctg gtcaccgtct cctcggccga caaaactcac     2400
acatgcggcc ggccctctgg ttccggtgat tttgattatg aaaagatggc aaacgctaat     2460 aaggggcta tgaccgaaaa tgccgatgaa aacgcgctac agtctgacgc taaaggcaaa      2520
cttgattctg tcgctactga ttacggtgct gctatcgatg gtttcattgg tgacgtttcc     2580
ggccttgcta atggtaatgg tgctactggt gattttgctg gctctaattc ccaaatggct     2640
```

```
caagtcggtg acggtgataa ttcaccttta atgaataatt tccgtcaata tttaccttcc    2700
ctccctcaat cggttgaatg tcgccctttt gtctttagcg ctggtaaacc atatgaattt    2760
tctattgatt gtgacaaaat aaacttattc cgtggtgtct ttgcgtttct tttatatgtt    2820
gccacctttn tgtatgtatt ttctacgttt gctaacatac tgcgtaataa ggagtcttaa    2880
tcatgccagt tcttttggct agcgccgccc tataccttgt ctgcctcccc gcgttgcgtc    2940
gcggtgcatg gagccgggcc acctcgacct gaatggaagc cggcggcacc tcgctaacgg    3000
attcaccact ccaagaattg gagccaatca attcttgcgg agaactgtga atgcgcaaac    3060
caaccctggg cagaacatat ccatcgcgtc cgccatctcc agcagccgca cgcggcgcat    3120
ctcgggcagc gttgggtcct ggccacgggt gcgcatgatc gtgctcctgt cgttgaggac    3180
ccggctaggc tggcggggtt gccttactgg ttagcagaat gaatcaccga tacgcgagcg    3240
aacgtgaagc gactgctgct gcaaaacgtc tgcgacctga gcaacaacat gaatggtctt    3300
cggtttccgt gtttcgtaaa gtctggaaac gcggaagtca gcgccctgca ccattatgtt    3360
ccggatctgc atcgcaggat gctgctggct accctgtgga acacctacat ctgtattaac    3420
gaagcgctgg cattgaccct gagtgatttt tctctggtcc cgccgcatcc ataccgccag    3480
ttgtttaccc tcacaacgtt ccagtaaccg ggcatgttca tcatcagtaa cccgtatcgt    3540
gagcatcctc tctcgtttca tcggtatcat taccccatg aacagaaatt ccccccttaca    3600 cggaggcatc aagtgaccaa acaggaaaaa accgccctta acatggcccg ctttatcaga    3660
agccagacat taacgcttct ggagaaactc aacgagctgg acgcggatga acaggcagac    3720
atctgtgaat cgcttcacga ccacgctgat gagctttacc gcaggatccg gaaattgtaa    3780
acgttaatat tttgttaaaa ttcgcgttaa atttttgtta aatcagctca ttttttaacc    3840
aataggccga atcggcaaa atcccttata atcaaaaga atagaccgag atagggttga    3900
gtgttgttcc agtttggaac aagagtccac tattaaagaa cgtggactcc aacgtcaaag    3960
ggcgaaaaac cgtctatcag ggctatggcc cactacgtga accatcaccc taatcaagtt    4020
ttttggggtc gaggtgccgt aaagcactaa atcggaaccc taagggagc cccgatttta    4080 gagcttgacg gggaaagccg gcgaacgtgg cgagaaagga agggaagaaa gcgaaaggag    4140
cgggcgctag ggcgctggca agtgtagcgg tcacgctgcg cgtaaccacc acaccgccg    4200 cgcttaatgc gccgctacag ggcgcgtccg gatcctgcct cgcgcgtttc ggtgatgacg    4260
gtgaaaacct ctgacacatg cagctcccgg agacggtcac agcttgtctg taagcggatg    4320
ccgggagcag acaagcccgt cagggcgcgt cagcgggtgt tggcgggtgt cggggcgcag    4380
ccatgaccca gtcacgtagc gatagcggag tgtatactgg cttaactatg cggcatcaga    4440
gcagattgta ctgagagtgc accatatgcg gtgtgaaata ccgcacagat gcgtaaggag    4500
aaaataccgc atcaggcgct cttccgcttc ctcgctcact gactcgctgc gctcggtcgt    4560
tcggctgcgg cgagcggtat cagctcactc aaaggcggta atacggttat ccacagaatc    4620
aggggataac gcaggaaaga acatgtgagc aaaaggccag caaaaggcca ggaaccgtaa    4680
aaaggccgcg ttgctggcgt ttttccatag gctccgcccc cctgacgagc atcacaaaaa    4740
tcgacgctca agtcagaggt ggcgaaaccc gacaggacta taaagatacc aggcgtttcc    4800
ccctggaagc tccctcgtgc gctctcctgt tccgaccctg ccgcttaccg gatacctgtc    4860
cgcctttctc ccttcgggaa gcgtggcgct ttctcatagc tcacgctgta ggtatctcag    4920
ttcggtgtag tcgttcgct ccaagctggg ctgtgtgcac gaaccccccg ttcagcccga    4980
ccgctgcgcc ttatccggta actatcgtct tgagtccaac ccggtaagac acgacttatc    5040
```

```
gccactggca gcagccactg gtaacaggat tagcagagcg aggtatgtag gcggtgctac    5100
agagttcttg aagtggtggc ctaactacgg ctacactaga aggacagtat ttggtatctg    5160
cgctctgctg aagccagtta ccttcggaaa aagagttggt agctcttgat ccggcaaaca    5220
aaccaccgct ggtagcggtg gttttttttgt ttgcaagcag cagattacgc gcagaaaaaa    5280
aggatctcaa gaagatcctt tgatcttttc tacggggtct gacgctcagt ggaacgaaaa    5340
ctcacgttaa gggattttgg tcatgagatt atcaaaaagg atcttcacct agatcctttt    5400
aaattaaaaa tgaagtttta aatcaatcta agtatatat gagtaaactt ggtctgacag    5460
ttaccaatgc ttaatcagtg aggcacctat ctcagcgatc tgtctatttc gttcatccat    5520
agttgcctga ctccccgtcg tgtagataac tacgatacgg agggcttac catctggccc    5580 cagtgctgca atgataccgc gagacccacg ctcaccggct ccagatttat cagcaataaa    5640
ccagccagcc ggaagggccg agcgcagaag tggtcctgca actttatccg cctccatcca    5700
gtctattaat tgttgccggg aagctagagt aagtagttcg ccagttaata gtttgcgcaa    5760
cgttgttgcc attgctgcag gcatcgtggt gtcacgctcg tcgtttggta tggcttcatt    5820
cagctccggt tcccaacgat caaggcgagt tacatgatcc cccatgttgt gcaaaaaagc    5880
ggttagctcc ttcggtcctc cgatcgttgt cagaagtaag ttggccgcag tgttatcact    5940
catggttatg gcagcactgc ataattctct tactgtcatg ccatccgtaa gatgcttttc    6000
tgtgactggt gagtactcaa ccaagtcatt ctgagaatag tgtatgcggc gaccgagttg    6060
ctcttgcccg gcgtcaacac gggataatac cgcgccacat agcagaactt taaaagtgct    6120
catcattgga aaacgttctt cggggcgaaa actctcaagg atcttaccgc tgttgagatc    6180
cagttcgatg taacccactc gtgcacccaa ctgatcttca gcatcttta ctttcaccag    6240 cgtttctggg tgagcaaaaa caggaaggca aaatgccgca aaaagggaa taagggcgac    6300 acggaaatgt tgaatactca tactcttcct ttttcaatat tattgaagca tttatcaggg    6360
ttattgtctc atgagcggat acatatttga atgtatttag aaaaataaac aataggggt    6420 tccgcgcaca tttccccgaa aagtgccacc tgacgtctaa gaaaccatta ttatcatgac    6480
attaacctat aaaaataggc gtatcacgag gccctttcgt cttcaa              6526
```

<210> SEQ ID NO 250
<211> LENGTH: 18
<212> TYPE: DNA
<213> ORGANISM: Artificial Sequence
<220> FEATURE:
<223> OTHER INFORMATION: chemically synthesized

<400> SEQUENCE: 250
ccagtaatga acaacagc                                                   18

<210> SEQ ID NO 251
<211> LENGTH: 18
<212> TYPE: DNA
<213> ORGANISM: Artificial Sequence
<220> FEATURE:
<223> OTHER INFORMATION: chemically synthesized

<400> SEQUENCE: 251
agccggaacc caaccgcg                                                   18

<210> SEQ ID NO 252
<211> LENGTH: 21
<212> TYPE: DNA

```
<213> ORGANISM: Artificial Sequence
<220> FEATURE:
<223> OTHER INFORMATION: chemically synthesized

<400> SEQUENCE: 252
agcgtaaaca gaagaacccc a                                               21

<210> SEQ ID NO 253
<211> LENGTH: 18
<212> TYPE: DNA
<213> ORGANISM: Artificial Sequence
<220> FEATURE:
<223> OTHER INFORMATION: chemically synthesized

<400> SEQUENCE: 253
accccaccag tagtaaga                                                   18

<210> SEQ ID NO 254
<211> LENGTH: 21
<212> TYPE: DNA
<213> ORGANISM: Artificial Sequence
<220> FEATURE:
<223> OTHER INFORMATION: chemically synthesized

<400> SEQUENCE: 254
gtacggaatg tacggatgcg g                                               21

<210> SEQ ID NO 255
<211> LENGTH: 10
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (1)..(9)
<223> OTHER INFORMATION: n is a, t, c or g

<400> SEQUENCE: 255 nnnnnnnnnc                                                            10

<210> SEQ ID NO 256
<211> LENGTH: 6
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (2)..(6)
<223> OTHER INFORMATION: Xaa is Y, S or G

<400> SEQUENCE: 256

Gln Xaa Xaa Xaa Xaa Xaa
1               5

<210> SEQ ID NO 257
<211> LENGTH: 6
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Xaa is Y, S or G
<220> FEATURE:
<221> NAME/KEY: MISC_FEATURE
<222> LOCATION: (4)..(4)
```

```
<223> OTHER INFORMATION: Xaa is Y, S or G

<400> SEQUENCE: 257

Xaa Ala Ser Xaa Leu Tyr
1               5

<210> SEQ ID NO 258
<211> LENGTH: 14
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(8)
<223> OTHER INFORMATION: Xaa is Y, S, G, A, F, W, H, P or V
<220> FEATURE:
<221> NAME/KEY: MISC_FEATURE
<222> LOCATION: (9)..(12)
<223> OTHER INFORMATION: Xaa is Y, S, G, A, F, W, H, P, V, or absent
<220> FEATURE:
<221> NAME/KEY: MISC_FEATURE
<222> LOCATION: (13)..(13)
<223> OTHER INFORMATION: Xaa is P or L
<220> FEATURE:
<221> NAME/KEY: MISC_FEATURE
<222> LOCATION: (14)..(14)
<223> OTHER INFORMATION: Xaa is F or I

<400> SEQUENCE: 258

Xaa Xaa Xaa Xaa Xaa Xaa Xaa Xaa Xaa Xaa Xaa Xaa Xaa Xaa
1               5                   10

<210> SEQ ID NO 259
<211> LENGTH: 6
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Xaa is I or L
<220> FEATURE:
<221> NAME/KEY: MISC_FEATURE
<222> LOCATION: (2)..(5)
<223> OTHER INFORMATION: Xaa is Y, S or G
<220> FEATURE:
<221> NAME/KEY: MISC_FEATURE
<222> LOCATION: (6)..(6)
<223> OTHER INFORMATION: Xaa is I or M

<400> SEQUENCE: 259

Xaa Xaa Xaa Xaa Xaa Xaa
1               5

<210> SEQ ID NO 260
<211> LENGTH: 10
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Xaa is Y, S or G
<220> FEATURE:
<221> NAME/KEY: MISC_FEATURE
<222> LOCATION: (3)..(3)
<223> OTHER INFORMATION: Xaa is Y, S or G
<220> FEATURE:
<221> NAME/KEY: MISC_FEATURE
<222> LOCATION: (4)..(4)
```

```
<223> OTHER INFORMATION: Xaa is P or S
<220> FEATURE:
<221> NAME/KEY: MISC_FEATURE
<222> LOCATION: (5)..(6)
<223> OTHER INFORMATION: Xaa is Y, S or G
<220> FEATURE:
<221> NAME/KEY: MISC_FEATURE
<222> LOCATION: (7)..(7)
<223> OTHER INFORMATION: Xaa is G or S
<220> FEATURE:
<221> NAME/KEY: MISC_FEATURE
<222> LOCATION: (8)..(8)
<223> OTHER INFORMATION: Xaa is Y, S or G
<220> FEATURE:
<221> NAME/KEY: misc_feature
<222> LOCATION: (10)..(10)
<223> OTHER INFORMATION: Xaa can be any naturally occurring amino acid

<400> SEQUENCE: 260

Xaa Ile Xaa Xaa Xaa Xaa Xaa Xaa Thr Xaa
1               5                   10

<210> SEQ ID NO 261
<211> LENGTH: 23
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (2)..(6)
<223> OTHER INFORMATION: Xaa is Y, S, G, A, F, W, H, P or V
<220> FEATURE:
<221> NAME/KEY: MISC_FEATURE
<222> LOCATION: (7)..(20)
<223> OTHER INFORMATION: Xaa is Y, S, G, A, F, W, H, P, V, or absent
<220> FEATURE:
<221> NAME/KEY: MISC_FEATURE
<222> LOCATION: (21)..(21)
<223> OTHER INFORMATION: Xaa is A or G
<220> FEATURE:
<221> NAME/KEY: MISC_FEATURE
<222> LOCATION: (22)..(22)
<223> OTHER INFORMATION: Xaa is F, I, L or M

<400> SEQUENCE: 261

Arg Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Asp
            20

<210> SEQ ID NO 262
<211> LENGTH: 12
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (3)..(5)
<223> OTHER INFORMATION: Xaa is Y, S, G, A, F, W, H, P or V
<220> FEATURE:
<221> NAME/KEY: MISC_FEATURE
<222> LOCATION: (6)..(9)
<223> OTHER INFORMATION: Xaa is Y, S, G, A, F, W, H, P, V, or absent
<220> FEATURE:
<221> NAME/KEY: MISC_FEATURE
<222> LOCATION: (10)..(10)
<223> OTHER INFORMATION: Xaa is P or L
<220> FEATURE:
<221> NAME/KEY: MISC_FEATURE
<222> LOCATION: (11)..(11)
<223> OTHER INFORMATION: Xaa is I or L
```

```
<400> SEQUENCE: 262

Gln Gln Xaa Xaa Xaa Xaa Xaa Xaa Xaa Xaa Thr
1               5                   10

<210> SEQ ID NO 263
<211> LENGTH: 6
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Xaa is I or L
<220> FEATURE:
<221> NAME/KEY: MISC_FEATURE
<222> LOCATION: (2)..(5)
<223> OTHER INFORMATION: Xaa is Y or S
<220> FEATURE:
<221> NAME/KEY: MISC_FEATURE
<222> LOCATION: (6)..(6)
<223> OTHER INFORMATION: Xaa is I or M

<400> SEQUENCE: 263

Xaa Xaa Xaa Xaa Xaa Xaa
1               5

<210> SEQ ID NO 264
<211> LENGTH: 10
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: Xaa is Y or S
<220> FEATURE:
<221> NAME/KEY: MISC_FEATURE
<222> LOCATION: (3)..(3)
<223> OTHER INFORMATION: Xaa is Y or S
<220> FEATURE:
<221> NAME/KEY: MISC_FEATURE
<222> LOCATION: (4)..(4)
<223> OTHER INFORMATION: Xaa is P or S
<220> FEATURE:
<221> NAME/KEY: MISC_FEATURE
<222> LOCATION: (5)..(6)
<223> OTHER INFORMATION: Xaa is Y or S
<220> FEATURE:
<221> NAME/KEY: MISC_FEATURE
<222> LOCATION: (7)..(7)
<223> OTHER INFORMATION: Xaa is G or S
<220> FEATURE:
<221> NAME/KEY: MISC_FEATURE
<222> LOCATION: (8)..(8)
<223> OTHER INFORMATION: Xaa is Y or S
<220> FEATURE:
<221> NAME/KEY: MISC_FEATURE
<222> LOCATION: (10)..(10)
<223> OTHER INFORMATION: Xaa is Y or S

<400> SEQUENCE: 264

Xaa Ile Xaa Xaa Xaa Xaa Xaa Xaa Thr Xaa
1               5                   10

<210> SEQ ID NO 265
<211> LENGTH: 26
<212> TYPE: PRT
<213> ORGANISM: Artificial Sequence
<220> FEATURE:
<223> OTHER INFORMATION: chemically synthesized
<220> FEATURE:
```

```
<221> NAME/KEY: MISC_FEATURE
<222> LOCATION: (2)..(6)
<223> OTHER INFORMATION: Xaa is Y, S, G, A, F, W, H, P or V
<220> FEATURE:
<221> NAME/KEY: MISC_FEATURE
<222> LOCATION: (7)..(23)
<223> OTHER INFORMATION: Xaa is Y, S, G, A, F, W, H, P, V, or absent
<220> FEATURE:
<221> NAME/KEY: MISC_FEATURE
<222> LOCATION: (24)..(24)
<223> OTHER INFORMATION: Xaa is A or G
<220> FEATURE:
<221> NAME/KEY: MISC_FEATURE
<222> LOCATION: (25)..(25)
<223> OTHER INFORMATION: Xaa is F, I, L or M

<400> SEQUENCE: 265

Arg Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Asp
            20                  25

<210> SEQ ID NO 266
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: X is Y, S, or G
<220> FEATURE:
<221> NAME/KEY: MISC_FEATURE
<222> LOCATION: (3)..(3)
<223> OTHER INFORMATION: X is Y, S, or G
<220> FEATURE:
<221> NAME/KEY: MISC_FEATURE
<222> LOCATION: (4)..(4)
<223> OTHER INFORMATION: X is P or S
<220> FEATURE:
<221> NAME/KEY: MISC_FEATURE
<222> LOCATION: (5)..(6)
<223> OTHER INFORMATION: X is Y, S, or G
<220> FEATURE:
<221> NAME/KEY: MISC_FEATURE
<222> LOCATION: (7)..(7)
<223> OTHER INFORMATION: X is G or S
<220> FEATURE:
<221> NAME/KEY: MISC_FEATURE
<222> LOCATION: (8)..(8)
<223> OTHER INFORMATION: X is Y, S, or G
<220> FEATURE:
<221> NAME/KEY: MISC_FEATURE
<222> LOCATION: (10)..(10)
<223> OTHER INFORMATION: X is Y, S, or G

<400> SEQUENCE: 266

Xaa Ile Xaa Xaa Xaa Xaa Xaa Xaa Thr Xaa
1               5                   10
```

MOLECULAR DISPLAY SYSTEM

RELATED APPLICATIONS

This application is a continuation of U.S. patent application Ser. No. 13/629,520, filed Sep. 27, 2012, now abandoned, which claims the benefit of provisional application U.S. Ser. No. 61/539,546 filed Sep. 27, 2011, the contents of which are herein incorporated by reference in their entirety.

INCORPORATION OF SEQUENCE LISTING

A computer readable form of the Sequence Listing "Substitute_Sequence_Listing_2223-P56672US00" (75,606 bytes) amended on Apr. 3, 2020 is hereby incorporated by reference.

FIELD OF INVENTION

This invention relates to the field of screening for affinity reagents to a molecular target, and more specifically to molecular display methods used in conjunction with sequencing.

BACKGROUND

Molecular display technologies are widely used to screen for potential affinity binders to a specific target molecule, however, there is potential for improving thereon. For example, phage display antibody technologies are used for isolating antibody fragments specific to antigens of interest, but selection of libraries against cell-surface antigens remains very challenging. The heterogeneity of the cell-surface and, accordingly, the relatively low concentration of the target antigen, give rise to large numbers of background phage clones. These phage clones may be non-specific binding clones, or may be specific for antigens other than the desired cell-surface target. Consequently, poor enrichment for binding phage clones is typically observed in cell selections. However, many proteins require the membrane environment for proper folding and stability and, as such, the ability to select phage-displayed antibody libraries against cell-surface epitopes remains crucial. If a protein is not properly folded, certain epitopes may not be available for binding by, for example, an affinity reagent. Likewise, proteins that are part of large complexes or associated with DNA, histones or other subcellular structures contain epitopes that are not necessarily made available for binding following traditional purification methods. For example, the properties of multi-pass membrane G-protein coupled receptors make their expression and purification very difficult, yet they are particularly relevant drug targets [1, 2]. Indeed, the high specificity of monoclonal antibodies, combined with their ability to engage immune mechanisms, makes this class of biologics of particular interest in the treatment of numerous cancers and infectious diseases [3,4,5]. A reliable selection methodology for targeting exposed epitopes (e.g. cell-surface epitopes), which eliminates the need for highly purified antigens, would significantly expand the range of antigens that could be targeted by therapeutic monoclonal antibodies.

Phage display selection strategies to reduce background binding to cells have included negative or competitive pre-absorption steps against multiple cell-lines [6, 7, 8, 9, 10] and various strategies to remove unbound from bound phage, including centrifugation through a density gradient [11, 12] and the pathfinder approach [13, 14]. Although these methods may help to enrich for phage clones specific to the antigen of interest, the number of unique antibody fragments recovered by these methods often remains relatively low, as phage display methodologies typically exhibit an affinity based selection pressure that promotes sequence convergence in later rounds of selection. New strategies are required to identify less prevalent clones that may exhibit desirable binding properties.

SUMMARY OF THE INVENTION

The methods described herein provide a rapid, efficient method of identifying binding agents, e.g., antibodies and antigen-binding fragments thereof, that specifically bind to cell-surface targets and other cell-surface expressed antigens. These methods include deep sequencing/high-throughput sequencing followed by a recovery method, also referred to herein as a rescue strategy. As used herein, the term "deep sequencing" and variations thereof refers to the number of times a nucleotide is read during the sequencing process. Deep sequencing indicates that the coverage, or depth, of the process is many times larger than the length of the sequence under study. Suitable deep sequencing methods include the methods described herein or any other art-recognized techniques. Suitable rescue strategies include the clonal ELISA assays and PCR rescue strategies described herein or any other art-recognized techniques. The methods provided herein do not require additional purification and/or isolation steps prior to identification and recovery of the binding agent, e.g., antibody or antigen-binding fragment thereof.

The methods provided herein are useful in identifying binding agents, e.g., antibodies and antigen-binding fragments thereof, which are not highly expressed in a given display. For example, the methods provided herein are useful in identifying polypeptide sequences that comprise less than 25%, less than 20%, less than 15%, less than 10%, less than 5%, less than 4%, less than 3%, less than 2%, less than 1%, less than 0.5% and/or less than 0.25% of the selection pool.

The methods provided herein are useful in differential selection strategies, for example, to identify binding agents that bind a given cell-surface target only when the target exhibits a particular modification, a particular conformation or other identifying characteristic. The methods provided herein are also useful in differential selection strategies, for example, to identify binding agents that bind a given cell-surface target only under certain metabolic or other biological conditions. The methods provided herein are also useful in differential selection strategies, for example, to identify binding agents that bind a given cell-surface target only in the presence of an effector, a target-binding partner or other molecule that must be present to enable binding between the genetically encoded binding agent and the target.

The methods provided herein are useful for identifying binding agents, particularly, binding polypeptides including antibodies and antigen-binding fragments thereof, also referred to herein as immunologically active fragments. In some embodiments, the antibody or antigen-binding fragment thereof is a monoclonal antibody, domain antibody, single chain, Fab fragment, a F(ab')$_2$ fragment, a scFv, a scab, a dAb, a single domain heavy chain antibody, and a single domain light chain antibody. In some embodiments, such an antibody or immunologically active fragment thereof that binds a given antigen, e.g., a cell-surface target, is a mouse, chimeric, humanized or fully human monoclonal antibody.

In some embodiments, the cell-surface target is selected from the group consisting of HER2, CD133, ErbB3, Fzd7, ROR1, ROR2, exon16 deleted ErbB2, and ITGA11. In some embodiments, the cell-surface target includes a modification that is required for epitope binding, such as, for example, an O-linked N-acetylglucosamine (O-GlcNAc) modification.

These cell-surface targets are expressed on mammalian cells. Suitable mammalian cells for use in the methods provided herein include, but are not limited to, cells such as 293, 293T, C2C12, and/or MC7 cells.

The methods provided herein are used in combination with phage-display libraries referred to herein as Libraries F and G, but those of ordinary skill in the art will appreciate that these methods can be used in conjunction with any peptide/polypeptide display system in which cell-surface targets/antigens are expressed. Library G is an scFv-phage library that was constructed by introducing degenerate codons into positions in CDR-H1, CDR-H2, CDR-H3, CDR-L1, CDR-L2 and CDR-L3 of a single human ScFv framework. Library F is an Fab-phage library that was constructed by introducing degenerate codons into positions in CDR-H1, CDR-H2, CDR-H3 and CDR-L3 of a single human Fab framework. Library F was constructed using an anti-maltose binding protein Fab as a template.

In an aspect, there is provided a method for identifying and/or recovering at least one genetically encoded affinity reagent specific for a target molecule, the method comprising: providing a molecular display system which displays a library of potential genetically encoded affinity reagents; screening the library against the target molecule to produce positive and negative selection pools; sequencing genetically encoded affinity reagents in each of the positive and negative selection pools; identifying at least one sequence that is more abundant in the positive selection pool as compared to the negative selection pool; and recovering at least one clone corresponding to the sequence.

In a further aspect, there is provided an antibody or antibody fragment comprising any one of CDR regions outlined in FIG. 2, FIG. 5 or FIG. 9. Preferably, the antibody or antibody fragment is selected from the group consisting of antibodies or antibody fragments comprising CDRL3, CDRH1, CDRH2 and CDRH3 of any one of clones WY574B, WY574E, WY574F, WY677C and WY677D described herein, the CDRH3 regions shown in FIG. 5 or the combinations of CDRL3 and CDRH3 regions shown in FIG. 9. In one embodiment, the antibody or antibody fragment is useful for the treatment of cancer, e.g., Her-2 positive cancer, preferably selected from the group consisting of breast cancer, ovarian cancer, uterine cancer and stomach cancer.

The invention provides antibodies and antigen-binding fragments thereof that bind HER2 and include a variable heavy chain complementarity determining region 1 (CDR-H1) comprising an amino acid sequence selected from the group consisting of SEQ ID NOs: 18, 22, 26, 30 and 34; a variable heavy chain complementarity determining region 2 (CDR-H2) comprising an amino acid sequence selected from the group consisting of SEQ ID NOs: 19, 23, 27, 31 and 35; a variable heavy chain complementarity determining region 3 (CDR-H3) comprising an amino acid sequence selected from the group consisting of SEQ ID NOs: 20, 24, 28, 32 and 36. In some embodiments, these anti-HER2 antibodies and antigen-binding fragments thereof also include a variable light chain complementarity determining region 1 (CDR-L1) comprising the amino acid sequence SVSSA (SEQ ID NO: 240); a variable light chain complementarity determining region 2 (CDR-L2) comprising the amino acid sequence SASSLYS (SEQ ID NO: 241); and a variable light chain complementarity determining region 3 (CDR-L3) comprising an amino acid sequence selected from the group consisting of SEQ ID NOs: 17, 21, 25, 29 and 33.

The invention provides antibodies and antigen-binding fragments thereof that bind HER2 and include a CDR-L1 comprising the amino acid sequence SVSSA (SEQ ID NO: 240), a CDR-L2 that includes the amino acid sequence SASSLYS (SEQ ID NO: 241), a CDR-L3 comprising the amino acid sequence $X_1$-$X_2$-$X_3$-$X_4$-$X_5$-$X_6$ (SEQ ID NO: 242), where $X_1$, $X_2$, $X_3$, and $X_4$ are Y, S, G, A, F, W, H, P or V and $X_5$ is P or L and $X_6$ is I or L; a CDR-H1 comprising the amino acid sequence $X_1$-$X_2$-$X_3$-$X_4$-$X_5$-$X_6$ (SEQ ID NO: 243), where $X_1$ is I or L, $X_2$, $X_3$, $X_4$, and $X_5$ are Y or S and where $X_6$ is I or M; and a CDR-H2 comprising the amino acid sequence $X_1$-I-$X_2$-$X_3$-$X_4$-$X_5$-$X_6$-$X_7$-$X_8$-T-$X_9$ (SEQ ID NO: 244), where $X_1$, $X_2$, $X_4$, $X_5$, $X_6$, $X_8$, and $X_9$ is Y or S, $X_3$ is P or S, and where $X_7$ is G or S; and a CDR-H3 comprising an amino acid sequence selected from the group consisting of SEQ ID NOs: 37-136.

The invention provides antibodies and antigen-binding fragments thereof that bind CD133 and include a CDR-L1 comprising the amino acid sequence the amino acid sequence Q-$X_1$-$X_2$-$X_3$-$X_4$-$X_5$ (SEQ ID NO: 245), where $X_1$, $X_2$, $X_3$, $X_4$, and $X_5$ are Y, S or, G; a CDR-L2 comprising the amino acid sequence $X_1$-A-S-$X_2$-L-Y (SEQ ID NO: 246), where $X_1$ and $X_2$ are Y, S or, G; a CDR-L3 comprising an amino acid sequence selected from the group consisting of SEQ ID NOs: 137, 139, 141, 143, 145, 147, 149, 151, 153, 155, 157 and 159; a CDR-H1 that includes the amino acid sequence $X_1$-$X_2$-$X_3$-$X_4$-$X_5$-$X_6$ (SEQ ID NO: 247), where $X_1$ is I or L, $X_2$, $X_3$, $X_4$, and $X_5$ are Y, S or G and where $X_6$ is I or M; a CDR-H2 that includes the amino acid sequence $X_1$-I-$X_2$-$X_3$-$X_4$-$X_5$-$X_6$-$X_7$-$X_8$-T-$X_9$ (SEQ ID NO: 266), where $X_1$, $X_2$, $X_4$, $X_5$, $X_6$, $X_8$, and $X_9$ is Y, S or G, $X_3$ is P or S, and where $X_7$ is G or S; and a CDR-H3 comprising an amino acid sequence selected from the group consisting of SEQ ID NOs: 138, 140, 142, 144, 146, 148, 150, 152, 154, 156, 158 and 160.

The invention provides antibodies and antigen-binding fragments thereof that bind ErbB3 and include a CDR-L1 comprising the amino acid sequence the amino acid sequence Q-$X_1$-$X_2$-$X_3$-$X_4$-$X_5$ (SEQ ID NO: 245), where $X_1$, $X_2$, $X_3$, $X_4$, and $X_5$ are Y, S or, G; a CDR-L2 comprising the amino acid sequence $X_1$-A-S-$X_2$-L-Y (SEQ ID NO: 246), where $X_1$ and $X_2$ are Y, S or, G; a CDR-L3 comprising an amino acid sequence selected from the group consisting of SEQ ID NOs: 161, 163, 165, 167, 169, 171, 173 and 175; a CDR-H1 that includes the amino acid sequence $X_1$-$X_2$-$X_3$-$X_4$-$X_5$-$X_6$ (SEQ ID NO: 247), where $X_1$ is I or L, $X_2$, $X_3$, $X_4$, and $X_5$ are Y, S or G and where $X_6$ is I or M; a CDR-H2 that includes the amino acid sequence $X_1$-I-$X_2$-$X_3$-$X_4$-$X_5$-$X_6$-$X_7$-$X_8$-T-$X_9$ (SEQ ID NO: 266), where $X_1$, $X_2$, $X_4$, $X_5$, $X_6$, $X_8$, and $X_9$ is Y, S or G, $X_3$ is P or S, and where $X_7$ is G or S; and a CDR-H3 comprising an amino acid sequence selected from the group consisting of SEQ ID NOs: 162, 164, 166, 168, 170, 172, 174 and 176.

The invention provides antibodies and antigen-binding fragments thereof that bind Fzd7 and include a CDR-L1 comprising the amino acid sequence SVSSA (SEQ ID NO: 240), a CDR-L2 that includes the amino acid sequence SASSLYS (SEQ ID NO: 241), a CDR-L3 comprising an amino acid sequence selected from the group consisting of SEQ ID NOs: 177, 179 and 181; a CDR-H1 comprising the amino acid sequence $X_1$-$X_2$-$X_3$-$X_4$-$X_5$-$X_6$ (SEQ ID NO: 243), where $X_1$ is I or L, $X_2$, $X_3$, $X_4$, and $X_5$ are Y or S and where $X_6$ is I or M; and a CDR-H2 comprising the amino acid sequence $X_1$-I-$X_2$-$X_3$-$X_4$-$X_5$-$X_6$-$X_7$-$X_8$-T-$X_9$ (SEQ ID NO: 244), where $X_1$, $X_2$, $X_4$, $X_5$, $X_6$, $X_8$, and $X_9$ is Y or S, $X_3$ is P or S, and where $X_7$ is G or S; and a CDR-H3 comprising an amino acid sequence selected from the group consisting of SEQ ID NOs: 178, 180 and 182.

The invention provides antibodies and antigen-binding fragments thereof that bind ROR1 and include a CDR-L1 comprising the amino acid sequence SVSSA (SEQ ID NO: 240), a CDR-L2 that includes the amino acid sequence SASSLYS (SEQ ID NO: 241), a CDR-L3 comprising an amino acid sequence selected from the group consisting of SEQ ID NOs: 183, 185 and 187; a CDR-H1 comprising the amino acid sequence $X_1$-$X_2$-$X_3$-$X_4$-$X_5$-$X_6$ (SEQ ID NO: 243), where $X_1$ is I or L, $X_2$, $X_3$, $X_4$, and $X_5$ are Y or S and where $X_6$ is I or M; and a CDR-H2 comprising the amino acid sequence $X_1$-I-$X_2$-$X_3$-$X_4$-$X_5$-$X_6$-$X_7$-$X_8$-T-$X_9$ (SEQ ID NO: 244), where $X_1$, $X_2$, $X_4$, $X_5$, $X_6$, $X_8$, and $X_9$ is Y or S, $X_3$ is P or S, and where $X_7$ is G or S; and a CDR-H3 comprising an amino acid sequence selected from the group consisting of SEQ ID NOs: 184, 186 and 188.

The invention provides antibodies and antigen-binding fragments thereof that bind ROR2 and include a CDR-L1 comprising the amino acid sequence SVSSA (SEQ ID NO: 240), a CDR-L2 that includes the amino acid sequence SASSLYS (SEQ ID NO: 241), a CDR-L3 comprising an amino acid sequence selected from the group consisting of SEQ ID NOs: 189, 191, 193, 195, 197 and 199; a CDR-H1 comprising the amino acid sequence $X_1$-$X_2$-$X_3$-$X_4$-$X_5$-$X_6$ (SEQ ID NO: 243), where $X_1$ is I or L, $X_2$, $X_3$, $X_4$, and $X_5$ are Y or S and where $X_6$ is I or M; and a CDR-H2 comprising the amino acid sequence $X_1$-I-$X_2$-$X_3$-$X_4$-$X_5$-$X_6$-$X_7$-$X_8$-T-$X_9$ (SEQ ID NO: 244), where $X_1$, $X_2$, $X_4$, $X_5$, $X_6$, $X_8$, and $X_9$ is Y or S, $X_3$ is P or S, and where $X_7$ is G or S; and a CDR-H3 comprising an amino acid sequence selected from the group consisting of SEQ ID NOs: 190, 192, 194, 196, 198 and 200.

The invention provides antibodies and antigen-binding fragments thereof that bind an ErbB2 variant known as exon 16 deleted ErbB2 and include a CDR-L1 comprising the amino acid sequence SVSSA (SEQ ID NO: 240), a CDR-L2 that includes the amino acid sequence SASSLYS (SEQ ID NO: 241), a CDR-L3 comprising an amino acid sequence selected from the group consisting of SEQ ID NOs: 201, 203 and 205; a CDR-H1 comprising the amino acid sequence $X_1$-$X_2$-$X_3$-$X_4$-$X_5$-$X_6$ (SEQ ID NO: 243), where $X_1$ is I or L, $X_2$, $X_3$, $X_4$, and $X_5$ are Y or S and where $X_6$ is I or M; and a CDR-H2 comprising the amino acid sequence $X_1$-I-$X_2$-$X_3$-$X_4$-$X_5$-$X_6$-$X_7$-$X_8$-T-$X_9$ (SEQ ID NO: 244), where $X_1$, $X_2$, $X_4$, $X_5$, $X_6$, $X_8$, and $X_9$ is Y or S, $X_3$ is P or S, and where $X_7$ is G or S; and a CDR-H3 comprising an amino acid sequence selected from the group consisting of SEQ ID NOs: 202, 204 and 206.

The invention provides antibodies and antigen-binding fragments thereof that bind ITGA11 and include a CDR-L1 comprising the amino acid sequence SVSSA (SEQ ID NO: 240), a CDR-L2 that includes the amino acid sequence SASSLYS (SEQ ID NO: 241), a CDR-L3 comprising an amino acid sequence selected from the group consisting of SEQ ID NOs: 207, 209, 211 and 213; a CDR-H1 comprising the amino acid sequence $X_1$-$X_2$-$X_3$-$X_4$-$X_5$-$X_6$ (SEQ ID NO: 243), where $X_1$ is I or L, $X_2$, $X_3$, $X_4$, and $X_5$ are Y or S and where $X_6$ is I or M; and a CDR-H2 comprising the amino acid sequence $X_1$-I-$X_2$-$X_3$-$X_4$-$X_5$-$X_6$-$X_7$-$X_8$-T-$X_9$ (SEQ ID NO: 244), where $X_1$, $X_2$, $X_4$, $X_5$, $X_6$, $X_8$, and $X_9$ is Y or S, $X_3$ is P or S, and where $X_7$ is G or S; and a CDR-H3 comprising an amino acid sequence selected from the group consisting of SEQ ID NOs: 208, 210, 212 and 214.

The invention provides antibodies and antigen-binding fragments thereof that recognize a modification known as O-GlcNac modification and include a CDR-L1 comprising the amino acid sequence SVSSA (SEQ ID NO: 240), a CDR-L2 that includes the amino acid sequence SASSLYS (SEQ ID NO: 241), a CDR-L3 comprising an amino acid sequence selected from the group consisting of SEQ ID NOs: 215, 217, 219 and 221; a CDR-H1 comprising the amino acid sequence $X_1$-$X_2$-$X_3$-$X_4$-$X_5$-$X_6$ (SEQ ID NO: 243), where $X_1$ is I or L, $X_2$, $X_3$, $X_4$, and $X_5$ are Y or S and where $X_6$ is I or M; and a CDR-H2 comprising the amino acid sequence $X_1$-I-$X_2$-$X_3$-$X_4$-$X_5$-$X_6$-$X_7$-$X_8$-T-$X_9$ (SEQ ID NO: 244), where $X_1$, $X_2$, $X_4$, $X_5$, $X_6$, $X_8$, and $X_9$ is Y or S, $X_3$ is P or S, and where $X_7$ is G or S; and a CDR-H3 comprising an amino acid sequence selected from the group consisting of SEQ ID NOs: 216, 218, 220 and 222.

In a further aspect, there is provided a method of treating cancer, e.g., Her-2 positive cancer, preferably selected from the group consisting of breast cancer, ovarian cancer, uterine cancer and stomach cancer, in a patient comprising administering to the patient a therapeutically effective amount of the antibody or antibody fragment described herein.

In a further aspect, there is provided a method of treating a disorder that is associated with aberrant expression and/or activity of the cell-surface target against which the antibody has been selected, comprising administering to the patient a therapeutically effective amount of the antibody or antibody fragment described herein.

In a further aspect, there is provided a use of the antibody or antibody fragment described herein for the treatment of cancer, e.g., Her-2 positive cancer, preferably selected from the group consisting of breast cancer, ovarian cancer, uterine cancer and stomach cancer.

In a further aspect, there is provided a use of the antibody or antibody fragment described herein for the treatment of a disorder that is associated with aberrant expression and/or activity of the cell-surface target against which the antibody has been selected.

In a further aspect, there is provided a use of the antibody or antibody fragment described herein in the preparation of a medicament for the treatment of Her-2 positive cancer, preferably selected from the group consisting of breast cancer, ovarian cancer, uterine cancer and stomach cancer.

In a further aspect, there is provided a use of the antibody or antibody fragment described herein in the preparation of a medicament for the treatment of a disorder that is associated with aberrant expression and/or activity of the cell-surface target against which the antibody has been selected.

BRIEF DESCRIPTION OF THE FIGURES

Embodiments of the invention may best be understood by referring to the following description and accompanying drawings. In the description and drawings, like numerals refer to like structures or processes. In the drawings:

FIG. 1A is a flow chart of the selection strategy used to isolate Fab clones specific for cell-surface displayed Her2. The positive selection begins a pre-absorption step in which the library phage are incubated with untransfected 293T cells. After incubation, the mixture is pelleted to remove the library clones bound to the cells. These clones are likely specific for cell-surface epitopes that are not of interest, or are non-specific binding clones. The phage of interest for subsequent steps are circled in red. The library phage remaining in the supernatant are incubated with the Her2 transfected 293T cells, non-binding phage are washed away, and the phage bound to the transfected cells are amplified in an *E. coli* host. The amplified phage are then purified and used in the next round of selection. In parallel, the negative selection is carried out by incubating library phage with untransfected 293T cells. Phage clones that do not bind to the cells are washed away, and the remaining bound phage (circled in red) are amplified in an *E. coli* host for the next round of selection.

FIG. 2 shows Her2 specific clones rescued from the positive selection pool. Five clones were rescued from the Her2 positive selection output pool by PCR amplification with primers specific to their unique CDR H3 sequence. The total number of times each CDRH3 was observed in the positive and negative selection pools is listed. The abundance of each sequence in the positive pool is also listed, as a percentage of the total number of sequences isolated. The CDR loops are defined by the IMGT nomenclature (Lefranc, Pommie, Ruiz et al (2003) Dev Comp Immunol 27, 55-77).

FIG. 3A shows the analysis of Fab binding to cell-surface Her2 by flow cytometry. Fabs WY574B (left panel), WY574E (middle panel), and WY 547F (right panel) were tested for binding to Her2 and EGFR transfected 293T cells. Binding of the anti-Her2 Fab proteins was detected using an Alexa488-conjugated secondary antibody (AF488) against a Flag-epitope on the C terminus of the Fab light-chain. The stained anti-Her2 transfected population is shown in green, the stained EGFR transfected population is shown in blue, and the unstained Her2 transfected population is shown in gray. The AF-488 positive cell gate is indicated. FIG. 3B shows that the Fabs were also testing for binding to Her2 positive (BT474) and negative (T47D) human breast cancer cell-lines, using the same secondary detection as in (a). The stained BT474 population is shown in green in the bottom panel, with the unstained population shown in gray. The stained T47D cell population is indicated in blue.

(FIG. 4A) 293T cells were seeded on coverslips coated with 50 mg/ml poly-D-lysine for 24 h followed by transient transfection of plasmid encoding HER2. (FIG. 4B) BT474 and T47D breast cancer cells were seeded onto uncoated coverslips. 48 h post-transfection or post-seeding, the cells were fixed with 3.7% formaldehyde without permeabilization and stained with anti-HER2 Fab protein (5 mg/ml) followed Alexa488-conjugated secondary antibody against a Flag-epitope on the C terminus of the Fab light-chain. The nuclei were stained using the Hoechst dye. The images were acquired using the WaveFX spinning disk confocal microscope by Quorom Technologies Inc. Composite images of the 'xy' and 'yz' planes are represented (scale bar, 10 um).

FIG. 5 shows the 100 most frequent CDRH3 sequences obtained from Illumina sequencing of the positive selection pool. The 100 most frequently observed CDR H3 sequences (positions 107-117 per IMGT) obtained from the round 3 positive selection output are listed, starting with the most frequently observed sequence. The number of counts reflects the number of times each sequence was observed in the positive or negative selection pool, or in the unselected naïve library. Sequences highlighted in yellow represent those clones that were rescued from the positive selection pool. Sequence number 13 corresponds to the wild type sequence that was used as the template in the library construction process.

(FIG. 6A) Two primer sets specific for both CDRH3 and CDRL3 are used to make recovery more specific. (FIG. 6B) Three primer sets are used to amplify three fragments in a strategy that makes use of both the CDRH3 and CDRL3 sequences, as well as unique Nsi1 and Nhe1 restriction sites in the library phage vector.

FIG. 9 shows the phage-Fab clones that were rescued from the positive selection pool.

FIG. 10 shows deep sequencing strategies to decode variable complementarity determining regions (CDRs) in pools of synthetic antibody fragments. The region of the phagemid encoding the Fab scaffold (solid black line) and its six CDRs (white boxes labeled L1, L2, L3, H1, H2, H3) is shown. PCR primers to generate amplicon sequencing libraries are shown as solid black arrows. Sequencing read orientations are shown as white block arrows. Strategies 1 and 2 are compatible with Illumina platforms and decode two or more CDRs. Strategy 3 is compatible with IonTorrent platforms and decodes only CDR-H3.

DETAILED DESCRIPTION

Figure 1B:
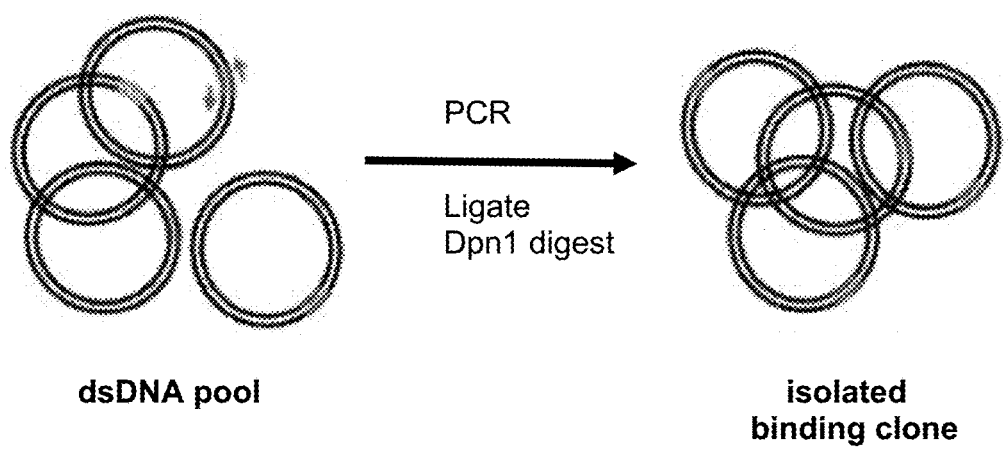
FIG. 1B shows Phage clones being rescued from the positive selection output pool using a PCR strategy in which abutting forward and reverse PCR primers (shown in red) anneal to the unique heavy chain CDR3 sequence (represented by the colored portion of the circular DNA molecules). PCR amplification results in synthesis of the complete phagemid vector. Ligation of the PCR product yields closed, circular, double-stranded DNA that can be transformed into bacteria for rescue. Dpn1 digestion of the PCR product degrades undesired phagemid DNA present from the positive selection pool (represented in gray), due to the presence of methylated Dpn1 recognition sites. As a consequence of in vitro synthesis, the PCR product is not methylated and, therefore, is not recognized by Dpn1.

There is described herein the development of a new method for selecting for affinity reagents against a target molecule.

In a specific example, there is described a new method for selecting phage display libraries against cell-surface expressed antigens. This methodology, termed CellectSeq, combines the use of phage-displayed synthetic antibody libraries and high throughput DNA sequencing technology. In the synthetic library approach, the antigen binding site contains 'man-made' diversity, which is introduced into human framework regions based on existing knowledge of antibody structure and function [15]. Consequently, synthetic libraries can be biased towards antibody clones with favorable properties, such as high stability and expression. The use of high throughput DNA sequencing enables the rapid identification of high affinity clones specific to cells that express the antigen of interest. Moreover, the methodology we report here allows rare binding clones, which may compose as little as 0.25% of the selection pool, to be identified and successfully rescued.

As an initial model system, we selected synthetic antibody libraries against cells transiently transfected to express the human epidermal growth factor receptor 2 (Her2, also known as ErbB2). A member of the human epidermal growth factor receptor (EGFR) family, Her2 is a transmembrane tyrosine kinase receptor involved in signalling pathways that promote cell proliferation and survival [16, 17]. Her2 is overexpressed in approximately 20 to 25% of invasive breast cancers [18, 19], and its overexpression correlates with increased tumor aggressiveness, an increased chance of recurrence, and poor prognosis in breast cancer patients [20, 21]. We selected phage-displayed synthetic antibody libraries against 293T cells transiently transfected to express Her2 and, in parallel, untransfected 293T cells. After three rounds of selection, each output pool was subjected to Illumina deep sequencing. We found that comparing the deep sequencing results of the positive and negative selection pools could identify Her2 specific clones. We were able to rescue clones unique to the positive selection pool using primers specific to the third hypervariable loop of the antibody heavy chain (CDR H3), and demonstrated that the rescued clones bind specifically and with high affinity to our target antigen, Her2. Our results suggest that the use of deep sequencing enables efficient identification of antibody fragments specific to target antigens presented on cell-surfaces.

While the initial model system used synthetic antibody libraries screened against cells expressing HER2, it is understood that the methods described herein are useful to identify binding agents that recognize any number of targets that are expressed on a cell-surface.

In an aspect, there is provided a method for identifying and/or recovering at least one genetically encoded affinity reagent specific for a target molecule, the method comprising: providing a molecular display system which displays a library of potential genetically encoded affinity reagents; screening the library against the target molecule to produce positive and negative selection pools, preferably with multiple rounds of selection; sequencing genetically encoded affinity reagents in each of the positive and negative selection pools; identifying at least one sequence that is more abundant in the positive selection pool as compared to the negative selection pool; and recovering at least one clone corresponding to the sequence.

As used herein, "affinity reagent" is any molecule that specifically binds to a target molecule, for example, to identify, track, capture or influence the activity of the target molecule. The affinity reagents identified or recovered by the methods described herein are "genetically encoded", for example an antibody, peptide or nucleic acid, and are thus capable of being sequenced. As used herein, the terms "protein", "polypeptide" and "peptide" are used interchangeably to refer to two or more amino acids linked together.

As used herein, "molecular display system" is any system capable of presenting a library of potential affinity reagents to screen for potential binders to a target molecule or ligand, for example, through in vitro protein evolution. Examples of display systems include phage display, bacterial display, yeast display, ribosome display and mRNA display. In one embodiment of the method, phage display is used.

In some embodiments, the sequencing is deep/high-throughput sequencing. Examples of deep/high-throughput sequencing include Lynx Therapeutics' Massively Parallel Signature Sequencing (MPSS), Polony sequencing, 454 pyrosequencing, Illumina (Solexa) sequencing, SOLiD sequencing, Ion semiconductor sequencing (Ion Torrent by Life Technologies™), and DNA nanoball sequencing. In a preferable embodiment, Illumina sequencing is used.

In some embodiments, the rescue strategy is a clonal ELISA assay, a PCR-based rescue strategy, including the clonal ELISA assay and PCR-based rescue strategies described herein.

In some embodiments, the affinity reagents are selected from the group consisting of nucleic acid molecules and polypeptides. In one embodiment, the affinity reagents are antibodies, preferably synthetic antibodies, and further preferably the library is a synthetic Fab or scFv library.

In some embodiments, each of the affinity reagents in the library contains unique sequence tags and the sequencing identifies the unique sequence tags. Preferably, the at least one clone is recovered by annealing primers specific for the unique sequence tags. For example, in a preferred embodiment, the library is a synthetic Fab library and the unique sequence tag is in the CDR H3 region.

In some embodiments, the target molecule is a cell surface protein. In further embodiments, the screening is performed against the target molecule presented on a cell surface. In some embodiments, the screening is performed against the target molecule presented on a mammalian cell surface.

In some embodiments, the sequences identified are more abundant in the positive selection pool as compared to the negative selection pool by a factor of at least 2, and in increasing preferably at least 3, at least 4 and at least 5.

The methods provided herein are used in combination with phage-display libraries referred to herein as Libraries F and G, but those of ordinary skill in the art will appreciate that these methods can be used in conjunction with any peptide/polypeptide display system in which cell-surface targets/antigens are expressed.

Library G is an scFv-phage library that was constructed by introducing degenerate codons into positions in CDR-H1, CDR-H2, CDR-H3, CDR-L1, CDR-L2 and CDR-L3 of a single human ScFv framework. The library has a total diversity of $1.08 \times 10^{11}$ unique clones, and the details of the library design are shown in Table 2 below, where the bolding in the CDR-L3 and CDR-H3 regions represents positions that were replaced by random loops of all possible varying lengths, as indicated.

TABLE 1

| CDR Sequences of Library G clones |
|---|

| CDR-L1 (SEQ ID NO: 256) |
|---|

| Position | 27 | 28 | 29 | 30 | 31 | 32 |
|---|---|---|---|---|---|---|
| | Q | YSG | YSG | YSG | YSG | YSG |

| CDR-L2 (SEQ ID NO: 257) |
|---|

| Position | 50 | 51 | 52 | 53 | 54 | 55 |
|---|---|---|---|---|---|---|
| | YSG | A | S | YSG | L | Y |

| CDR-L3 (SEQ ID NO: 258) |
|---|

Loop Length (8-12 aa)

| Position | 91 | 92 | 93 | 94 | 95 | 96 |
|---|---|---|---|---|---|---|
| | Z | Z | Z | Z | PL | Fl |

TABLE 1-continued

CDR Sequences of Library G clones

CDR-H1 (SEQ ID NO: 259)

| Position | 29 | 30 | 31 | 32 | 33 | 34 |
|---|---|---|---|---|---|---|
| | IL | YSG | YSG | YSG | YSG | IM |

CDR-H2 (SEQ ID NO: 260)

| Position | 50 | 51 | 52 | 52a | 53 | 54 | 55 | 56 | 57 | 58 |
|---|---|---|---|---|---|---|---|---|---|---|
| | YSG | I | YSG | PS | YSG | YSG | GS | YSG | T | YSG |

CDR-H3 (SEQ ID NO: 261)

Loop Length (7-19 aa)

| Position | 98 | 99 | 100 | 101 | 102 | 103 | 104 | 104a | 104b | 104c | 105 |
|---|---|---|---|---|---|---|---|---|---|---|---|
| | R | Z | Z | Z | Z | Z | Z | Z | AG | FILM | D |

Z = 25% Y, 20% S, 20% G, 10% A, and 5% each of F, W, H, P, V

The nucleotide sequence of the vector encoding Library G is shown below:

| FEATURES | Location/Qualifiers |
|---|---|
| rep_origin | 3764 . . . 4235<br>/note = "f1 origin" |
| sig_peptide | 1534 . . . 1602<br>/note = "ST2 secr signal" |
| promoter | 21 . . . 52<br>/note = "LacIq promoter" |
| promoter | 1412 . . . 1439<br>/note = "pTac promoter" |
| ORF | 87 . . . 1169<br>/note = "LacIq" |
| ORF | complement(5461 . . . 6321)<br>/note = "AmpR" |
| ORF | 2416 . . . 2880<br>/note = "III gene (truncated)" |
| misc_feature | 2008 . . . 2385<br>/note = "VH" |
| misc_feature | 1639 . . . 1959<br>/note = "VL" |
| misc_feature | 1960 . . . 2007<br>/note = "linker C3" |
| misc_feature | 2302 . . . 2346<br>/note = "CDRH3" |
| misc_feature | 2155 . . . 2184<br>/note = "CDRH2" |
| misc_feature | 1606 . . . 1629<br>/note = "FLAG tag" |
| misc_feature | 1786 . . . 1806<br>/note = "CDRL2" |
| misc_feature | 2092 . . . 2109<br>/note = "CDRH1" |
| misc_feature | 1909 . . . 1926<br>/note = "CDRL3" |
| misc_feature | 2389 . . . 2403<br>/note = "hinge" |
| misc_feature | 1720 . . . 1734<br>/note = "CDRL1" |

| FEATURES | Location/Qualifiers |
|---|---| misc_feature 2404 . . . 2415
/note = "dimerization domain"

(SEQ ID NO: 249)

```
   1 gaattcccga caccatcgaa tggtgcaaaa cctttcgcgg tatggcatga tagcgcccgg 61 aagagagtca attcagggtg gtgaatgtga aaccagtaac gttatacgat gtcgcagagt 121 atgccggtgt ctcttatcag accgtttccc gcgtggtgaa ccaggccagc cacgtttctg 181 cgaaaacgcg ggaaaaagtg gaagcggcga tggcggagct gaattacatt cccaaccgcg 241 tggcacaaca actggcgggc aaacagtcgt tgctgattgg cgttgccacc tccagtctgg 301 ccctgcacgc gccgtcgcaa attgtcgcgg cgattaaatc tcgcgccgat caactgggtg 361 ccagcgtggt ggtgtcgatg gtagaacgaa gcggcgtcga agcctgtaaa gcggcggtgc 421 acaatcttct cgcgcaacgc gtcagtgggc tgatcattaa ctatccgctg gatgaccagg 481 atgccattgc tgtggaagct gcctgcacta atgttccggc gttatttctt gatgtctctg 541 accagacacc catcaacagt attattttct cccatgaaga cggtacgcga ctgggcgtgg 601 agcatctggt cgcattgggt caccagcaaa tcgcgctgtt agcgggccca ttaagttctg 661 tctcggcgcg tctgcgtctg gctggctggc ataaatatct cactcgcaat caaattcagc 721 cgatagcgga acgggaaggc gactggagtg ccatgtccgg ttttcaacaa accatgcaaa 781 tgctgaatga gggcatcgtt cccactgcga tgctggttgc caacgatcag atggcgctgg 841 gcgcaatgcg cgccattacc gagtccgggc tgcgcgttgg tgcggatatc tcggtagtgg 901 gatacgacga taccgaagac agctcatgtt atatcccgcc gttaaccacc atcaaacagg 961 attttcgcct gctggggcaa accagcgtgg accgcttgct gcaactctct cagggccagg 1021 cggtgaaggg caatcagctg ttgcccgtct cactggtgaa aagaaaaacc accctggcgc 1081 ccaatacgca aaccgcctct ccccgcgcgt tggccgattc attaatgcag ctggcacgac 1141 aggtttcccg actggaaagc gggcagtgag cgcaacgcaa ttaatgtgag ttagctcact 1201 cattaggcac aattctcatg tttgacagct tatcatcgac tgcacggtgc accaatgctt 1261 ctggcgtcag cagccatcg gaagctgtgg tatggctgtg caggtcgtaa atcactgcat 1321 aattcgtgtc gctcaaggcg cactcccgtt ctggataatg ttttttgcgc cgacatcata 1381 acggttctgg caaatattct gaaatgagct gttgacaatt aatcatcggc tcgtataatg 1441 tgtggaattg tgagcggata acaatttcac acaggaaaca gccagtccgt ttaggtgttt 1501 tcacgagcac ttcaccaaca aggaccatag attatgaaaa agaatatcgc atttcttctt 1561 gcatctatgt tcgttttttc tattgctaca aatgcctatg catccgatta caaagatgac 1621 gatgacaaag gcggtggcga tatccagatg acccagtccc cgagctccct gtccgcctct 1681 gtgggcgata gggtcaccat cacctgccgt gccagtcagt ccgtgtccag cgctgtagcc 1741 tggtatcaac agaaaccagg aaaagctccg aagcttctga tttactcggc atccagcctc 1801 tactctggag tcccttctcg cttctctggt agccgttccg ggacggattt cactctgacc 1861 atcagcagtc tgcagccgga agacttcgca acttattact gtcagcaatc ttcttattct 1921 ctgatcacgt tcggacaggg taccaaggtg gagatcaaag gtactactgc cgctagtggt 1981 agtagtggtg gcagtagcag tggtgccgag gttcagctgg tggagtctgg cggtggcctg 2041 gtgcagccag ggggctcact ccgtttgtcc tgtgcagctt ctggcttcaa ctttcttct 2101 tcttctatac actgggtgcg tcaggccccg ggtaagggcc tggaatgggt tgcatctatt
```

-continued

| FEATURES | Location/Qualifiers |
|---|---|

```
2161 tcttcttctt atggctatac ttattatgcc gatagcgtca agggccgttt cactataagc
2221 gcagacacat ccaaaaacac agcctaccta caaatgaaca gcttaagagc tgaggacact
2281 gccgtctatt attgtgctcg cactgttcgt ggatccaaaa aaccgtactt ctctggttgg
2341 gctatggact actggggtca aggaaccctg gtcaccgtct cctcggccga caaaactcac
2401 acatgcggcc ggccctctgg ttccggtgat tttgattatg aaaagatggc aaacgctaat
2461 aagggggcta tgaccgaaaa tgccgatgaa aacgcgctac agtctgacgc taaaggcaaa
2521 cttgattctg tcgctactga ttacggtgct gctatcgatg gtttcattgg tgacgtttcc
2581 ggccttgcta atggtaatgg tgctactggt gattttgctg gctctaattc ccaaatggct
2641 caagtcggtg acggtgataa ttaccttta atgaataatt ccgtcaata tttaccttcc
2701 ctccctcaat cggttgaatg tcgcccttt gtctttagcg ctggtaaacc atatgaattt
2761 tctattgatt gtgacaaaat aaacttattc cgtggtgtct ttgcgtttct tttatatgtt
2821 gccacctta tgtatgtatt ttctacgttt gctaacatac tgcgtaataa ggagtcttaa
2881 tcatgccagt tcttttggct agcgccgccc tataccttgt ctgcctcccc gcgttgcgtc
2941 gcggtgcatg gagccgggcc acctcgacct gaatggaagc cggcggcacc tcgctaacgg
3001 attcaccact ccaagaattg gagccaatca attcttgcgg agaactgtga atgcgcaaac
3061 caacccttgg cagaacatat ccatcgcgtc cgccatctcc agcagccgca cgcggcgcat
3121 ctcgggcagc gttgggtcct ggccacgggt gcgcatgatc gtgctcctgt cgttgaggac
3181 ccggctaggc tggcggggtt gccttactgg ttagcagaat gaatcaccga tacgcgagcg
3241 aacgtgaagc gactgctgct gcaaaacgtc tgcgacctga gcaacaacat gaatggtctt
3301 cggtttccgt gtttcgtaaa gtctggaaac gcggaagtca gcgccctgca ccattatgtt
3361 ccggatctgc atcgcaggat gctgctggct accctgtgga acacctacat ctgtattaac
3421 gaagcgctgg cattgaccct gagtgatttt tctctggtcc cgccgcatcc ataccgccag
3481 ttgtttaccc tcacaacgtt ccagtaaccg ggcatgttca tcatcagtaa cccgtatcgt
3541 gagcatcctc tctcgtttca tcggtatcat taccccatg aacagaaatt cccccttaca
3601 cggaggcatc aagtgaccaa acaggaaaaa accgccctta acatggcccg ctttatcaga
3661 agccagacat taacgcttct ggagaaactc aacgagctgg acgcggatga acaggcagac
3721 atctgtgaat cgcttcacga ccacgctgat gagctttacc gcaggatccg gaaattgtaa
3781 acgttaatat tttgttaaaa ttcgcgttaa attttttgtta aatcagctca ttttttaacc
3841 aataggccga atcggcaaa atcccttata aatcaaaaga atagaccgag atagggttga
3901 gtgttgttcc agtttggaac aagagtccac tattaaagaa cgtggactcc aacgtcaaag
3961 ggcgaaaaac cgtctatcag ggctatggcc cactacgtga accatcaccc taatcaagtt
4021 ttttggggtc gaggtgccgt aaagcactaa atcggaaccc taagggagc ccccgattta
4081 gagcttgacg gggaaagccg gcgaacgtgg cgagaaagga agggaagaaa gcgaaaggag
4141 cgggcgctag gcgctggca agtgtagcgg tcacgctgcg cgtaaccacc acacccgccg
4201 cgcttaatgc gccgctacag ggcgcgtccg gatcctgcct cgcgcgtttc ggtgatgacg
4261 gtgaaaacct ctgacacatg cagctcccgg agacggtcac agcttgtctg taagcggatg
4321 ccgggagcag acaagcccgt cagggcgcgt cagcgggtgt tggcgggtgt cggggcgcag
4381 ccatgaccca gtcacgtagc gatagcggag tgtatactgg cttaactatg cggcatcaga
4441 gcagattgta ctgagagtgc accatatgcg gtgtgaaata ccgcacagat gcgtaaggag
```

| FEATURES | Location/Qualifiers |
|---|---|

```
4501 aaaataccgc atcaggcgct cttccgcttc ctcgctcact gactcgctgc gctcggtcgt 4561 tcggctgcgg cgagcggtat cagctcactc aaaggcggta atacggttat ccacagaatc 4621 aggggataac gcaggaaaga acatgtgagc aaaaggccag caaaaggcca ggaaccgtaa 4681 aaaggccgcg ttgctggcgt ttttccatag gctccgcccc cctgacgagc atcacaaaaa 4741 tcgacgctca agtcagaggt ggcgaaaccc gacaggacta taaagatacc aggcgtttcc 4801 ccctggaagc tccctcgtgc gctctcctgt tccgaccctg ccgcttaccg gatacctgtc 4861 cgcctttctc ccttcgggaa gcgtggcgct ttctcatagc tcacgctgta ggtatctcag 4921 ttcggtgtag gtcgttcgct ccaagctggg ctgtgtgcac gaaccccccg ttcagcccga 4981 ccgctgcgcc ttatccggta actatcgtct tgagtccaac ccggtaagac acgacttatc 5041 gccactggca gcagccactg gtaacaggat tagcagagcg aggtatgtag gcggtgctac 5101 agagttcttg aagtggtggc ctaactacgg ctacactaga aggacagtat ttggtatctg 5161 cgctctgctg aagccagtta ccttcggaaa aagagttggt agctcttgat ccggcaaaca 5221 aaccaccgct ggtagcggtg gtttttttgt ttgcaagcag cagattacgc gcagaaaaaa 5281 aggatctcaa gaagatcctt tgatcttttc tacggggtct gacgctcagt ggaacgaaaa 5341 ctcacgttaa gggattttgg tcatgagatt atcaaaaagg atcttcacct agatcctttt 5401 aaattaaaaa tgaagtttta aatcaatcta agtatatat gagtaaactt ggtctgacag 5461 ttaccaatgc ttaatcagtg aggcacctat ctcagcgatc tgtctatttc gttcatccat 5521 agttgcctga ctccccgtcg tgtagataac tacgatacgg gagggcttac catctggccc 5581 cagtgctgca atgataccgc gagacccacg ctcaccggct ccagatttat cagcaataaa 5641 ccagccagcc ggaagggccg agcgcagaag tggtcctgca actttatccg cctccatcca 5701 gtctattaat tgttgccggg aagctagagt aagtagttcg ccagttaata gtttgcgcaa 5761 cgttgttgcc attgctgcag gcatcgtggt gtcacgctcg tcgtttggta tggcttcatt 5821 cagctccggt tcccaacgat caaggcgagt tacatgatcc cccatgttgt gcaaaaaagc 5881 ggttagctcc ttcggtcctc cgatcgttgt cagaagtaag ttggccgcag tgttatcact 5941 catggttatg gcagcactgc ataattctct tactgtcatg ccatccgtaa gatgcttttc 6001 tgtgactggt gagtactcaa ccaagtcatt ctgagaatag tgtatgcggc gaccgagttg 6061 ctcttgcccg gcgtcaacac gggataatac cgcgccacat agcagaactt taaaagtgct 6121 catcattgga aaacgttctt cggggcgaaa actctcaagg atcttaccgc tgttgagatc 6181 cagttcgatg taacccactc gtgcacccaa ctgatcttca gcatctttta ctttcaccag 6241 cgtttctggg tgagcaaaaa caggaaggca aaatgccgca aaaaagggaa taagggcgac 6301 acggaaatgt tgaatactca tactcttcct ttttcaatat tattgaagca tttatcaggg 6361 ttattgtctc atgagcggat acatatttga atgtatttag aaaaataaac aaataggggt 6421 tccgcgcaca tttccccgaa aagtgccacc tgacgtctaa gaaaccatta ttatcatgac 6481 attaacctat aaaaataggc gtatcacgag gccctttcgt cttcaa
```

Library F is an Fab-phage library that was constructed by introducing degenerate codons into positions in CDR-H1, CDR-H2, CDR-H3 and CDR-L3 of a single human Fab framework. The loop length of the CDR-L3 and/or CDR-H3 in Library F can vary as shown in the table below. The library has a total diversity of $3 \times 10^{10}$ unique clones, and the details of the library design are shown in Table 2 below, where the bolding in the CDR-L3 and CDR-H3 regions represents positions that were replaced by random loops of all possible varying lengths, as indicated.

TABLE 2

CDR Sequences of Library F Clones

CDR-L3 (SEQ ID NO: 262)

Loop Length (8-12 aa)

| Q | Q | Z | Z | Z | Z | PL | IL | T |

CDR-H1 (SEQ ID NO: 263)

| Position | 29 | 30 | 31 | 32 | 33 | 34 |
|---|---|---|---|---|---|---|
|  | IL | YS | YS | YS | YS | IM |

TABLE 2-continued

CDR Sequences of Library F Clones

CDR-H2 (SEQ ID NO: 264)

| Position | 50 | 51 | 52 | 52a | 53 | 54 | 55 | 56 | 57 | 58 |
|---|---|---|---|---|---|---|---|---|---|---|
|  | YS | I | YS | PS | YS | YS | GS | YS | T | YS |

CDR-H3 (SEQ ID NO: 265)

Loop Length (5-22 aa)

| Position | 94 | 95 | 96 | 97 | 98 | 99 | 100 | 100a | 100b | 100c | 101 |
|---|---|---|---|---|---|---|---|---|---|---|---|
|  | R | Z | Z | Z | Z | Z | Z | Z | AG | FILM | D |

Z = 25% Y, 20% S, 20% G, 10% A, and 5% each of F, W, H, P, V

The nucleotide sequence of the vector encoding Library F is shown below:

```
FEATURES       Location/Qualifiers
promoter       536 . . . 752
               /note = "Pho A"

ORF            complement(4052 . . . 4913)
               /note = "AmpR"

ORF            2461 . . . 2925
               /note = "III gene (G2-CT)"

sig_peptide    804 . . . 872
               /note = " ST2 secr signal"

sig_peptide    1669 . . . 1737
               /note = "ST2 secr signal"

misc_feature   1747 . . . 2124
               /note = "VH"

misc_feature   1197 . . . 1526
               /note = "CL"

misc_feature   876 . . . 1196
               /note = "VL"

misc_feature   2125 . . . 2433
               /note = "CH1"

misc_feature   2041 . . . 2085
               /note = "CDRH3"

misc_feature   1894 . . . 1923
               /note = "CDRH2"

misc_feature   1527 . . . 1550
               /note = "FLAG tag"

misc_feature   1023 . . . 1043
               /note = "CDRL2"

misc_feature   1146 . . . 1163
               /note = "CDRL3"

misc_feature   1831 . . . 1848
               /note = "CDRH1"

misc_feature   2434 . . . 2448
               /note = "Hinge"

misc_feature   957 . . . 971
               /note = "CDRL1"
```

-continued

| FEATURES | Location/Qualifiers |
|---|---| misc_feature 2449 . . . 2460
/note = "dimerization domain"

(SEQ ID NO: 248)

```
   1 ggaaattgta aacgttaata ttttgttaaa attcgcgtta aattttttgtt aaatcagctc 61 atttttttaac caataggccg aaatcggcaa aatcccttat aaatcaaaag aatagaccga 121 gataggggttg agtgttgttc cagtttggaa caagagtcca ctattaaaga acgtggactc 181 caacgtcaaa gggcgaaaaa ccgtctatca gggcgatggc ccactacgtg aaccatcacc 241 ctaatcaagt ttttttgggt cgaggtgccg taaagcacta aatcggaacc ctaaagggag 301 cccccgattt agagcttgac ggggaaagcc ggcgaacgtg gcgagaaagg aagggaagaa 361 agcgaaagga gcgggcgcta gggcgctggc aagtgtagcg gtcacgctgc gcgtaaccac 421 cacacccgcc gcgcttaatg cgccgctaca gggcgcgtcg cgccattcgc cattcaggct 481 gcgcaactgt tgggaagggc gatcggtgcg ggcctcttcg ctattacgcg catgcgacca 541 acagcggttg attgatcagg tagagggggc gctgtacgag gtaaagcccg atgccagcat 601 tcctgacgac gatacggagc tgctgcgcga ttacgtaaag aagttattga agcatcctcg 661 tcagtaaaaa gttaatctttt tcaacagctg tcataaagtt gtcacggccg agacttatag 721 tcgctttgtt tttatttttt aatgtatttg taactagtac gcaagttcac gtaaaaaggg 781 tatgtagagg ttgaggtgat tttatgaaaa agaatatcgc atttcttctt gcatctatgt 841 tcgttttttc tattgctaca aatgcctatg catccgatat ccagatgacc cagtccccga 901 gctccctgtc cgcctctgtg ggcgataggg tcaccatcac ctgccgtgcc agtcagtccg 961 tgtccagcgc tgtagcctgg tatcaacaga accaggaaaa agctccgaag cttctgattt 1021 actcggcatc cagcctctac tctggagtcc cttctcgctt ctctggtagc cgttccggga 1081 cggatttcac tctgaccatc agcagtctgc agccggaaga cttcgcaact tattactgtc 1141 agcaatcttc ttattctctg atcacgttcg gacagggtac caaggtggag atcaaacgaa 1201 ctgtggctgc accatctgtc ttcatcttcc cgccatctga ttcacagttg aaatctggaa 1261 ctgcctctgt tgtgtgcctg ctgaataact tctatcccag agaggccaaa gtacagtgga 1321 aggtggataa cgccctccaa tcgggtaact cccaggagag tgtcacagag caggacagca 1381 aggacagcac ctacagcctc agcagcaccc tgacgctgag caaagcagac tacgaaaaac 1441 ataaagtcta cgcctgcgaa gtcacccatc agggcctgag ctcgcccgtc acaaagagct 1501 tcaacagggg agagtgtggt ggttctgatt acaaagatga cgatgacaaa taattaactc 1561 gaggctgagc aaagcagact actaataaca taaagtctac gccggacgca tcgtggccct 1621 agtacgcaag ttcacgtaaa aagggtaact agaggttgag gtgattttat gaaaagaat 1681 atcgcatttc ttcttgcatc tatgttcgtt ttttctattg ctacaaacgc gtacgctgag 1741 atctccgagg ttcagctggt ggagtctggc ggtggcctgg tgcagccagg gggctcactc 1801 cgtttgtcct gtgcagcttc tggcttcaac ttttcttctt cttctataca ctgggtgcgt 1861 caggccccgg gtaagggcct ggaatgggtt gcatctattt cttcttctta tggctatact 1921 tattatgccg atagcgtcaa gggccgtttc actataagcg cagacacatc caaaaacaca 1981 gcctacctac aaatgaacag cttaagagct gaggacactg ccgtctatta ttgtgctcgc 2041 actgttcgtg gatccaaaaa accgtacttc tctggttggg ctatggacta ctggggtcaa 2101 ggaaccctgg tcaccgtctc ctcggcctcc accaagggtc catcggtctt cccccctggca
```

| FEATURES | Location/Qualifiers |
|---|---|
| 2161 | ccctcctcca agagcacctc tgggggcaca gcggccctgg gctgcctggt caaggactac |
| 2221 | ttccccgaac cggtgacggt gtcgtggaac tcaggcgccc tgaccagcgg cgtgcacacc |
| 2281 | ttcccggctg tcctacagtc ctcaggactc tactccctca gcagcgtggt gaccgtgccc |
| 2341 | tccagcagct tgggcaccca gacctacatc tgcaacgtga atcacaagcc cagcaacacc |
| 2401 | aaggtcgaca agaaagttga gcccaaatct tgtgacaaaa ctcacacatg cggccggccc |
| 2461 | tctggttccg gtgattttga ttatgaaaag atggcaaacg ctaataaggg ggctatgacc |
| 2521 | gaaaatgccg atgaaaacgc gctacagtct gacgctaaag gcaaacttga ttctgtcgct |
| 2581 | actgattacg gtgctgctat cgatggtttc attggtgacg tttccggcct tgctaatggt |
| 2641 | aatggtgcta ctggtgattt tgctggctct aattcccaaa tggctcaagt cggtgacggt |
| 2701 | gataattcac ctttaatgaa taatttccgt caatatttac cttccctccc tcaatcggtt |
| 2761 | gaatgtcgcc cttttgtctt tagcgctggt aaaccatatg aattttctat tgattgtgac |
| 2821 | aaaataaact tattccgtgg tgtctttgcg tttcttttat atgttgccac ctttatgtat |
| 2881 | gtattttcta cgtttgctaa catactgcgt aataaggagt cttaaagctc caattcgccc |
| 2941 | tatagtgagt cgtattacaa ttcactggcc gtcgttttac aacgtcgtga ctgggaaaac |
| 3001 | cctggcgtta cccaacttaa tcgccttgca gcacatcccc ctttcgccag ctgcattaat |
| 3061 | gaatcggcca acgcgcgggg agaggcggtt tgcgtattgg gcgctcttcc gcttcctcgc |
| 3121 | tcactgactc gctgcgctcg gtcgttcggc tgcggcgagc ggtatcagct cactcaaagg |
| 3181 | cggtaatacg gttatccaca gaatcagggg ataacgcagg aaagaacatg tgagcaaaag |
| 3241 | gccagcaaaa ggccaggaac cgtaaaaagg ccgcgttgct ggcgtttttc cataggctcc |
| 3301 | gcccccctga cgagcatcac aaaaatcgac gctcaagtca gaggtggcga acccgacag |
| 3361 | gactataaag ataccaggcg tttccccctg gaagctccct cgtgcgctct cctgttccga |
| 3421 | ccctgccgct taccggatac ctgtccgcct ttctcccttc gggaagcgtg gcgctttctc |
| 3481 | atagctcacg ctgtaggtat ctcagttcgg tgtaggtcgt tcgctccaag ctgggctgtg |
| 3541 | tgcacgaacc ccccgttcag cccgaccgct gcgccttatc cggtaactat cgtcttgagt |
| 3601 | ccaacccggt aagacacgac ttatcgccac tggcagcagc cactggtaac aggattagca |
| 3661 | gagcgaggta tgtaggcggt gctacagagt tcttgaagtg gtggcctaac tacggctaca |
| 3721 | ctagaaggac agtatttggt atctgcgctc tgctgaagcc agttaccttc ggaaaaagag |
| 3781 | ttggtagctc ttgatccggc aaacaaacca ccgctggtag cggtggtttt tttgtttgca |
| 3841 | agcagcagat tacgcgcaga aaaaaggat ctcaagaaga tcctttgatc ttttctacgg |
| 3901 | ggtctgacgc tcagtggaac gaaaactcac gttaagggat tttggtcatg agattatcaa |
| 3961 | aaaggatctt cacctagatc cttttaaatt aaaaatgaag ttttaaatca atctaaagta |
| 4021 | tatatgagta aacttggtct gacagttacc aatgcttaat cagtgaggca cctatctcag |
| 4081 | cgatctgtct atttcgttca tccatagttg cctgactccc cgtcgtgtag ataactacga |
| 4141 | tacgggaggg cttaccatct ggccccagtg ctgcaatgat accgcgagac ccacgctcac |
| 4201 | cggctccaga tttatcagca ataaaccagc cagccggaag ggccgagcgc agaagtggtc |
| 4261 | ctgcaacttt atccgcctcc atccagtcta ttaattgttg ccgggaagct agagtaagta |
| 4321 | gttcgccagt taatagtttg cgcaacgttg ttgccattgc tacaggcatc gtggtgtcac |
| 4381 | gctcgtcgtt tggtatggct tcattcagct ccggttccca acgatcaagg cgagttacat |
| 4441 | gatcccccat gttgtgcaaa aaagcggtta gctccttcgg tcctccgatc gttgtcagaa |

| FEATURES | Location/Qualifiers |
|---|---|

```
4501 gtaagttggc cgcagtgtta tcactcatgg ttatggcagc actgcataat tctcttactg 4561 tcatgccatc cgtaagatgc ttttctgtga ctggtgagta ctcaaccaag tcattctgag 4621 aatagtgtat gcggcgaccg agttgctctt gcccggcgtc aatacgggat aataccgcgc 4681 cacatagcag aactttaaaa gtgctcatca ttggaaaacg ttcttcgggg cgaaaactct 4741 caaggatctt accgctgttg agatccagtt cgatgtaacc cactcgtgca cccaactgat 4801 cttcagcatc ttttactttc accagcgttt ctgggtgagc aaaaacagga aggcaaaatg 4861 ccgcaaaaaa gggaataagg gcgacacgga aatgttgaat actcatactc ttccttttc 4921 aatattattg aagcatttat cagggttatt gtctcatgag cggatacata tttgaatgta 4981 tttagaaaaa taaacaaata ggggttccgc gcacatttcc ccgaaaagtg ccacctg
```

Figure 9:
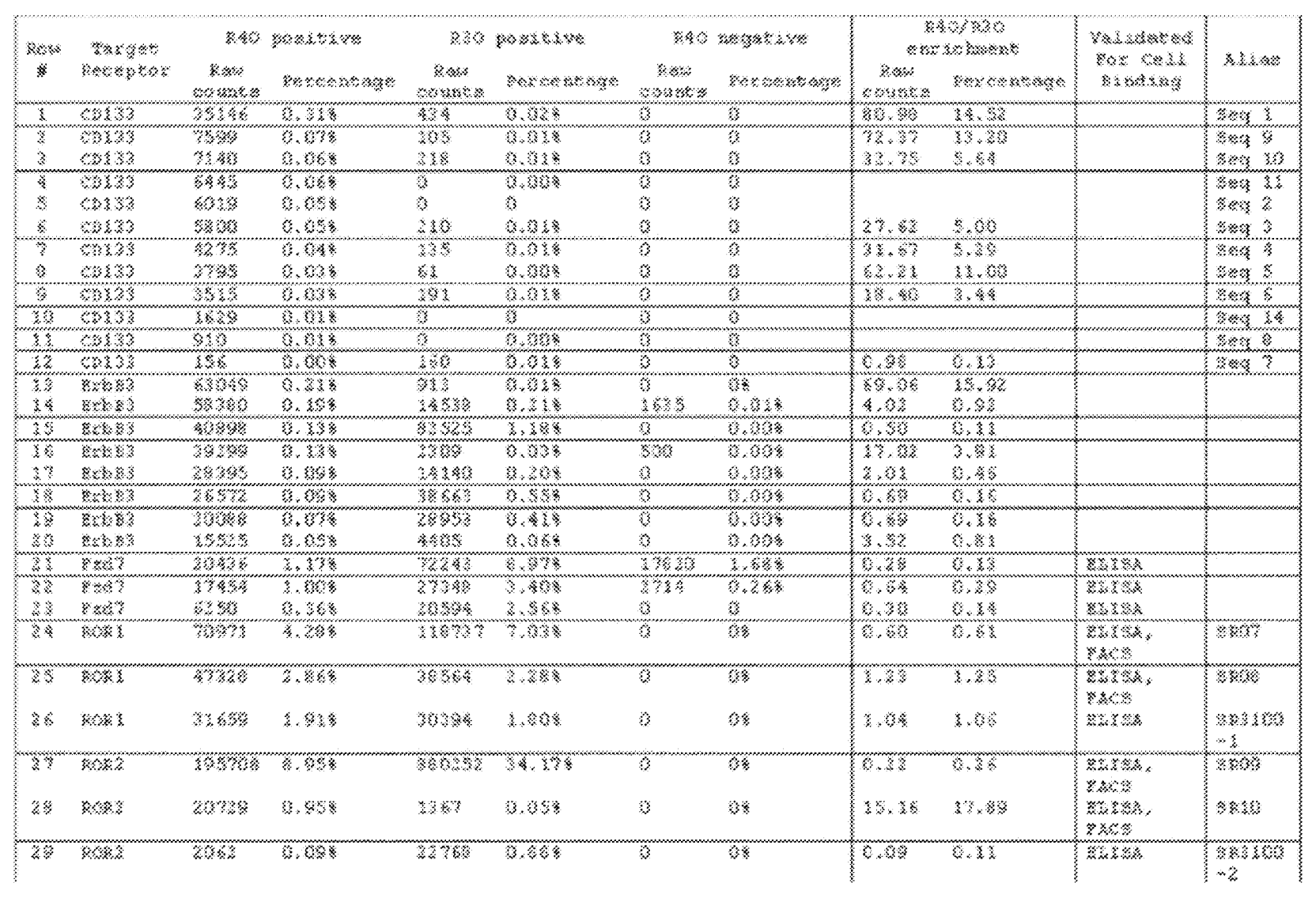

In a further aspect, there is provided an antibody or antibody fragment comprising any one of CDR regions outlined in FIG. 2, FIG. 5 or FIG. 9. For antibodies or antigen-binding fragments thereof shown in FIG. 2 or derived from those shown in FIG. 2, the antibody or fragment contains a CDR-L1 that includes the amino acid sequence SVSSA (SEQ ID NO: 240), a CDR-L2 that includes the amino acid sequence SASSLYS (SEQ ID NO: 241), and one of the combinations of CDR-L3, CDR-H1, CDR-H2 and CDR-H3 shown in FIG. 2.

For antibodies or antigen-binding fragments thereof shown in FIG. 5 or derived from those shown in FIG. 5, the antibody or fragment contains a CDR-L1 that includes the amino acid sequence SVSSA (SEQ ID NO: 240), a CDR-L2 that includes the amino acid sequence SASSLYS (SEQ ID NO: 241), a CDR-L3 that includes the amino acid sequence $X_1$-$X_2$-$X_3$-$X_4$-$X_5$-$X_6$ (SEQ ID NO: 242), where $X_1$, $X_2$, $X_3$, and $X_4$ are Y, S, G, A, F, W, H, P or V and $X_5$ is P or L and $X_6$ is I or L; a CDR-H1 that includes the amino acid sequence $X_1$-$X_2$-$X_3$-$X_4$-$X_5$-$X_6$ (SEQ ID NO: 243), where $X_1$ is I or L, $X_2$, $X_3$, $X_4$, and $X_5$ are Y or S and where $X_6$ is I or M; and a CDR-H2 that includes the amino acid sequence $X_1$-I-$X_2$-$X_3$-$X_4$-$X_5$-$X_6$-$X_7$-$X_8$-T-$X_9$ (SEQ ID NO: 244), where $X_1$, $X_3$, $X_5$, $X_8$, and $X_{10}$ is Y or S, $X_4$ is P or S, and where $X_7$ is G or S; and one of the CDR-H3 sequences shown in FIG. 5.

For antibodies or antigen-binding fragments thereof shown in FIG. 9 or derived from those shown in FIG. 9 and were identified from Library F, the antibody or fragment contains a CDR-L1 that includes the amino acid sequence SVSSA (SEQ ID NO: 240), a CDR-L2 that includes the amino acid sequence SASSLYS (SEQ ID NO: 241), a CDR-L3 that includes the amino acid sequence $X_1$-$X_2$-$X_3$-$X_4$-$X_5$-$X_6$ (SEQ ID NO: 242), where $X_1$, $X_2$, $X_3$, and $X_4$ are Y, S, G, A, F, W, H, P or V and $X_5$ is P or L and $X_6$ is I or L; a CDR-H1 that includes the amino acid sequence $X_1$-$X_2$-$X_3$-$X_4$-$X_5$-$X_6$ (SEQ ID NO: 243), where $X_1$ is I or L, $X_2$, $X_3$, $X_4$, and $X_5$ are Y or S and where $X_6$ is I or M; and a CDR-H2 that includes the amino acid sequence $X_1$-I-$X_2$-$X_3$-$X_4$-$X_5$-$X_6$-$X_7$-$X_8$-T-$X_9$ (SEQ ID NO: 244), where $X_1$, $X_3$, $X_5$, $X_8$, and $X_{10}$ is Y or S, $X_4$ is P or S, and where $X_7$ is G or S; and one of the combinations of CDR-L3 and CDR-H3 sequences shown in FIG. 9 (where the Library column indicates F).

For antibodies or antigen-binding fragments thereof shown in FIG. 9 or derived from those shown in FIG. 9 and were identified from Library G, the antibody or fragment contains a CDR-L1 that includes the amino acid sequence Q-$X_1$-$X_2$-$X_3$-$X_4$-$X_5$ (SEQ ID NO: 245), where $X_1$, $X_2$, $X_3$, $X_4$, and $X_5$ are Y, S or, G; a CDR-L2 that includes the amino acid sequence $X_1$-A-S-$X_2$-L-Y (SEQ ID NO: 246), where $X_1$, and $X_3$ are Y, S or, G; a CDR-H1 that includes the amino acid sequence $X_1$-$X_2$-$X_3$-$X_4$-$X_5$-$X_6$ (SEQ ID NO: 247), where $X_1$ is I or L, $X_2$, $X_3$, $X_4$, and $X_5$ are Y, S or G and where $X_6$ is I or M; a CDR-H2 that includes the amino acid sequence $X_1$-I-$X_2$—$X_3$-$X_4$-$X_5$-$X_6$-$X_7$-$X_8$-T-$X_9$ (SEQ ID NO: 244), where $X_1$, $X_3$, $X_5$, $X_8$, and $X_{10}$ is Y, S or G, $X_4$ is P or S, and where $X_7$ is G or S; and one of the combinations of CDR-L3 and CDR-H3 sequences shown in FIG. 9 (where the Library column indicates G).

Preferably, the antibody or antibody fragment is selected from the group consisting of antibodies or antibody fragments comprising CDRL3, CDRH1, CDRH2 and CDRH3 of any one of clones WY574B, WY574E, WY574F, WY677C and WY677D described herein, the CDRH3 regions shown in FIG. 5 or the combinations of CDRL3 and CDRH3 regions shown in FIG. 9. In one embodiment, the antibody or antibody fragment is for the treatment of cancer, e.g., Her-2 positive cancer, preferably selected from the group consisting of breast cancer, ovarian cancer, uterine cancer and stomach cancer.

In a further aspect, there is provided a method of treating a disorder that is associated with aberrant expression and/or activity of the cell-surface target against which the antibody has been selected comprising administering to the patient a therapeutically effective amount of the antibody or antibody fragment described herein.

In a further aspect, there is provided a method of treating a cancer, such as a Her-2 positive cancer, preferably selected from the group consisting of breast cancer, ovarian cancer, uterine cancer and stomach cancer, in a patient comprising administering to the patient a therapeutically effective amount of the antibody or antibody fragment described herein.

In a further aspect, there is provided a use of the antibody or antibody fragment described herein for the treatment of a cancer, such as a Her-2 positive cancer, preferably selected from the group consisting of breast cancer, ovarian cancer, uterine cancer and stomach cancer.

In a further aspect, there is provided a use of the antibody or antibody fragment described herein in the preparation of a medicament for the treatment of a cancer, such as Her-2 positive cancer, preferably selected from the group consisting of breast cancer, ovarian cancer, uterine cancer and stomach cancer.

The following examples are illustrative of various aspects of the invention, and do not limit the broad aspects of the invention as disclosed herein.

EXAMPLES

Example 1. Rapid Isolation of Antibody Fragments to Cell-Surface Targets

The considerable heterogeneity of cell-surfaces makes selection of phage-displayed antibody libraries against cell-surface antigens challenging. We report the development of a unique methodology for rapidly isolating phage-displayed antibody fragments to cell-surface targets, using the oncogenic human epidermal growth factor receptor 2 (Her2) as a model. Synthetic phage-displayed libraries were selected in parallel on Her2-positive and negative cells. Following three rounds of selection, the output phage pools were analyzed by Illumina deep sequencing. Comparisons of the sequences from the positive and negative selection pool allowed sequences specific to the antigen-expressing cell-line to be readily identified from background phage clones. A PCR amplification strategy that used primers specific to the unique heavy chain third hypervariable loop enabled the recovery of clones from the positive selection pool, which represented 2.95% to 0.25% of the phage pool. Binding kinetics measured by surface plasmon resonance showed that all of the recovered antibody fragments bind to Her2 specifically and with high affinity. Three of the isolated antibody fragments were assayed for specific binding to Her2 expressed on the surface of transiently transfected cells and a Her2+ breast cancer cell-line by flow cytometry and immunofluorescence. These antibody fragments displayed specific binding to cell-surface Her2, demonstrating that our methodology, termed CellectSeq, is amenable to the rapid identification of high affinity antibody fragments specific to cell-surface epitopes. Together, these results suggest that the CellectSeq approach can increase the efficiency of library selections to cell-surface targets and eliminates the need for purified antigen.

Materials and Methods

Cell Culture 293T cells were cultured in Dulbecco's Modified Eagle medium (DMEM) supplemented with 10% heat inactivated fetal bovine serum (FBS). Human breast cancer cell lines T47D and BT474 cells were cultured in DMEM supplemented with 10% FBS and penicillin and streptomycin. All cells were cultured at 37° C. in a humid incubator with 5% $CO_2$.

Phage-Displayed Fab Library and Screening

Selections were performed using Library F, a single framework human Fab library constructed similarly to previously described libraries [28, 29]. Briefly, a phagemid vector was engineered to bivalent display a human Fab on the pIII protein of M13 bacteriophage. All three heavy chain CDRs and the light chain CDR3 were mutagenized using Kunkel mutagenesis and tailored oligonucleotide mixtures. Solvent assessable residues of CDRs H1 and H2 were restricted to tyrosine and serine residues, whereas CDRs H3 and L3 were allowed a much more complex chemical diversity of the following composition: 25% Tyr, 20% Ser, 20% Gly, 10% Ala, and 5% each of Phe, Trp, His, Pro and Val. The CDR H3 and L3 lengths were varied between 5 to 22 and 8 to 12 residues, respectively.

Library F was cycled through three rounds of selection, each consisting of a pre-absorption step followed by a positive selection step. For the pre-absorption step, 293T cells were trypsinized briefly and re-suspended in a single cell suspension in DMEM with 10% FBS. Ten million cells were pelleted at 1200 rpm for three minutes and cells were mixed with approximately $10^{12}$ cfu of library F phage in DMEM containing 10% FBS, 50 mM HEPES, 2 mM EDTA. The cells and library were incubated for 1.5 to 2 hours at 4° C. with gentle rocking, after which the cells were pelleted and the library supernatant was used in the following positive selection step.

For positive selection, 293T cells were harvested and plated at $2 \times 10^6$ cells in 150 mm tissue culture dishes (BD Falcon). Twenty-four hours after plating, cells were co-transfected with a Her2 expression plasmid (8 µg) and a GFP expression plasmid (2 pg) using Fugene 6 (Roche Applied Sciences), following the manufacturer's instructions. Approximately 48 hours post-transfection, cells were harvested as described above for the pre-absorption step. Five million cells were pelleted and re-suspended in the phage library supernatant from the pre-absorption step. The library and transfected cells were incubated for 2 hours at 4° C. with gentle shaking. Following incubation, cells were pelleted as before, the supernatant was discarded, and cells were re-suspended in cold phosphate-buffered saline (PBS). This process was repeated for a total of two washes for round one and three washes for rounds two and three. To obtain the negative selection pool for Illumina sequencing, Library F was also selected for three rounds against 5 million untransfected 293T cells, using the same methods described for the positive selection step.

Positively selected phage were amplified similarly to previous described methods [30]. Briefly, XL1blue cells were grown to an $OD_{600}$ of 0.8 in 2YT media containing 10 pg/ml tetracycline. Following washing of the positively selected cells, 3 ml of the XL1blue culture was added directly to the cell pellet. Cells and bacteria were incubated for 30 to 40 minutes at 37° C. with gentle shaking and approximately $10^{10}$ cfu of M13 K07 helper phage was added. The culture was incubated for 45 minutes at 37° C., shaking at 200 rpm, and then transferred to a 40 ml 2YT culture (100 pg/ml carbenicillin, 25 pg/ml kanamycin). The culture was grown overnight at 37° C., shaking at 200 rpm. The amplified phage culture was harvested for subsequent selection rounds as previously described [30].

Illumina Sequencing and PCR Amplification of Phagemid Clones

The round three positive and negative selection pool phage, along with the naïve library, were infected into XL1blue cells and grown overnight in 2YT supplement with 100 µg/ml carbenicillin. Cultures were miniprepped (Qiagen) to obtain phagemid DNA to use as the templates for a PCR with individual forward primers comprised of an adaptor sequence (5'AATGATACGGCGACCACCGAGA-TCTACACTCTTTCCCTACACGACGCTCTTCCGATCT-3') (SEQ ID NO: 1), a five base pair barcode sequence (positive pool: 5'-GAGTA-'3 (SEQ ID NO: 2); negative pool: 5'-CCAAA-'3 (SEQ ID NO: 3); naïve library: 5'-TT-GTT-3' (SEQ ID NO: 4)) and an annealing site to the third antibody framework region of the heavy chain (5'-GTCT-ATTATTGTGCTCGC-3') (SEQ ID NO: 5). For all phage pools, a reverse primer containing a second Illumina-compatible adaptor region (5'-CAAGCAGAAGACGGCATAC-GAGCTCTTC-3') (SEQ ID NO: 6) and an annealing site to the phagemid vector (5'-TCCTTGA- CCCCAGTAGTC-3') (SEQ ID NO: 7) was used. PCR reactions were performed with the high fidelity polymerase Phusion (Finnzyme) and 400 to 600 ng of template DNA. Reactions were subjected to 15 cycles of annealing and extension, consisting of 30 s at 57° C. and 45 s at 72° C. PCR products were digested with ExoI (USB), SAP (USB), and DpnI (NEB) and then purified on a PCR purification column (Qiagen). Successful amplification of the correct DNA fragment from each phage pool was verified by agarose gel electrophoresis. The amplified DNA fragments were pooled and subjected to Illumina DNA sequencing on an Illumina GAII, with 72 base pair reads. Each sequencing read was assigned to its correct pool on the basis of its unique barcode sequence. The reads were filtered according to their Phred score [31]. Since a constant aligner region was sequenced, these regions were used to optimize the phred score cutoffs. Briefly, all sequences with phred scores of 20 and higher for every base were kept. A tolerance number (5) of medium quality (phred score higher than 15) was allowed. DNA sequences were translated to decode the sequence of the heavy chain CDR3.

To rescue individual clones from the positive selection pool, primers (described below) were phosphorylated as previously described [30]. The phosphorylated primers were then used in a PCR reaction, in which phage pool DNA was used as a template. The amount of DNA template per reaction was varied between 1 to 100 ng. The amount of DNA template varied with the prevalence of the given clone in the Illumina pool, with greatest amount of DNA template (100 ng) being used in PCR reactions to rescue the least prevalent clones. Reactions were performed with the high fidelity polymerase Phusion (Finnzyme), using the manufacturer recommended conditions. Reactions were subjected to 30 to 35 cycles of annealing and extension, consisting of 30 s at 65 or 68° C. and 180 s at 72° C. PCR products were confirmed by agarose gel electrophoresis and approximately 50 ng of the PCR product was used directly in ligation reaction (400 U T4 ligase, NEB). Ligations were incubated overnight at room temperature, and then heat inactivated at 65° C. for 10 minutes. Following the PCR, DpnI (NEB) was added to digest template DNA present in the reactions and samples were transformed into chemically competent XL1blue cells. Rescued transformations were plated on 2YT agar plates with carbenicillin and incubated overnight at 37° C. Single colonies were inoculated into 96-well culture plates for overnight growth of single phage clones as previously described [30]. The heavy and light chains of individual phage clones were PCR amplified and the PCR products were sequenced to ensure the recovery of clones with the desired CDR H3.

Vectors and Primers

For PCR recovery the following phosphorylated forward and reverse primers were used to recover the phage-Fab clones:

```
WY574B:
5'-CCAGTAATGAACAACAGC-3',        (SEQ ID NO: 250)

5'-TACGGTTACGTTTCTGGT-3';        (SEQ ID NO: 8)

WY574E:
5'-AGCCGGAACCCAACCGCG-3',        (SEQ ID NO: 251)

5'-TACCCGTCTTACGGTTTG-3';        (SEQ ID NO: 9)

WY574F:
5'-AGCGTAAACAGAAGAACCCCA-3',     (SEQ ID NO: 252)

5'-TGGTCTCCGGCTTCTTGGTCT-3';     (SEQ ID NO: 10)

WY677C:
5'-ACCCCACCAGTAGTAAGA-3',        (SEQ ID NO: 253)

5'-CCGTGGTCTGGTTACTCT-3';        (SEQ ID NO: 11)

WY677D:
5'-GTACGGAATGTACGGATGCGG-3',     (SEQ ID NO: 254)

5'-TACTCTTACTGGGGTCCGTACTAC-3'.  (SEQ ID NO: 12)
```

Heavy ($V_H$) and light-chain ($V_L$) variable regions were amplified for sequencing with the following primers that add M13 forward and reverse binding sites, respectively:

```
VH:
                                 (SEQ ID NO: 13)
5'-TGTAAAACGACGGCCAGTGGACGCATCGTGGCCCTA-3', (SEQ ID NO: 14)
5'-CAGGAAACAGCTATGACCCCTTGGTGGAGGCCGAG-3';

VL:
                                 (SEQ ID NO: 15)
5'-TGTAAAACGACGGCCAGTCTGTCATAAAGTTGTCACGG-3', (SEQ ID NO: 16)
5'-CAGGAAACAGCTATGACCCCTTGGTACCCTGTCCG-3'
```

Her2 and EGFR were both expressed from pCDNA3 (Invitrogen) [32, 33], and GFP was expressed from a previously reported plasmid [34].

Protein Expression and Purification

Fab proteins were expressed in 55244 *E. coli* from the phage display phagemid engineered with an amber stop codon between the Fab and pIII proteins, introduced by a standard Kunkel mutagenesis reaction [30]. Single colonies of each clone were grown overnight at 30° C. in 2YT media supplemented with 50 µg/ml carbenicillin and 25 µg/ml kanamycin. Overnight cultures were centrifuged at 3000 g for 10 minutes and pellets were re-suspended in 25 ml of complete CRAP media [30]. Ten milliliters of the re-suspended culture was used to inoculate 1 L of CRAP media, which was subsequently grown for 24 to 27 hours at 30° C., pelleted, re-suspended in 25 ml of PBS, and frozen. After thawing, 15 mg of lysozyme (Bioshop) and 30 µl of DNase I (deoxyribonuclease I, Fermentus) was added to 30 ml of cell suspension and cells were lysed by sonication. Following centrifugation to pellet cell debris, Fab supernatants were loaded onto fast-flow rProtein A-Sepharose (GE Healthcare) pre-equilibrated in PBS. Columns were washed with PBS, eluted with 50 mM $NaH_2PO_4$, 100 mM $H_3PO_4$, 140 mM NaCl, pH 2.5. Eluates were neutralized with 1 M $Na_2HPO_4$, 140 mM NaCl. Recovered Fab proteins were analyzed by SDS-PAGE and quantified using a Bradford assay (Bio-Rad).

Surface Plasmon Resonance

The binding affinities and kinetic parameters for interactions between Her2 specific Fabs and recombinant Her2 (R&D Systems) were measured by surface plasmon resonance using a ProteOn XPR36 instrument (Bio-Rad). HER2 was immobilized on a GLC chip by standard amine coupling chemistry and serial dilutions of Fab in PBS with 0.05% Tween 20 were injected over the Her2 and blank channels (for reference subtraction) for 60 seconds at a flow rate of 100 µl/min, followed by ten minutes of buffer to monitor Fab dissociation. The chip surface was regenerated with 0.85% $H_3PO_4$ prior to new analyte injection. Kinetic parameters were determined by globally fitting a reference cell-subtracted concentration series to a 1:1 (Langmuir) binding model.

Flow Cytometry and Immunofluorescence Staining

For flow cytometric analysis of transfected 293T cells, $3 \times 10^6$ cells were plated on 10 cm dishes (BD Falcon). Twenty-four hours after plating, cells were transfected with 10 µg of a Her2, EGFR, or GFP expression vector using Fugene 6 (Roche Applied Sciences), following the manufacturer's instructions. Approximately 24 hours post-transfection, cells were harvested using a cell scraper into PBS containing 2% FBS (wash buffer). The cells were washed once with wash buffer and re-suspended into a single cell suspension. Approximately 1.0 to $1.5 \times 10^6$ cells were placed into 1.5 ml tubes for staining with individual Fab clones. First, cells were incubated for 45 minutes at room temperature in PBS containing 2% FBS to block non-specific epitopes. Next, cells were incubated with 2 µg of the Her2 specific Fabs (diluted in wash buffer) for 20 minutes at room temperature and then washed twice with wash buffer. The samples were incubated for 20 minutes at room temperature with a 1:100 dilution of anti-FLAG-Alexa488 secondary antibody (Cell Signaling) in wash buffer. Finally, cells were washed twice and re-suspended in 0.5 ml of PBS for analysis on a BD FacsAria I flow cytometer (BD Biosciences).

For flow cytometric analysis of Fab binding to the human cancer cell-lines, $5 \times 10^5$ BT474 and T47D cells were plated per well of 6-well plates (BD Falcon). Approximately 48 hours after plating, media was aspirated from the 6-well plates and cells were washed twice with cold PBS. Wells were then blocked with wash buffer for 45 minutes at 4° C. The blocking solution was aspirated and 4 µg of the Fab sample in 0.5 ml of wash buffer was added to the appropriate well. Wells were washed twice with wash buffer, and then incubated with secondary antibody as above for 30 minutes at 4° C. Wells were washed three times; cells were harvested into PBS using a cell scraper, and analyzed as above.

Immunofluorescence for cell-surface HER2 was carried out on intact cells seeded on round glass coverslips uncoated or coated with 50 µg/mL poly-D-lysine (BD Biosciences). 48 hours post-seeding or post-transfection with a plasmid encoding HER2, the cells were washed with ice-cold PBS containing 1 mM $MgCl_2$ and 1 mM $CaCl_2$ on ice. The subsequent steps were performed at 4° C., unless otherwise indicated. The cells were fixed for 10 min with 3% paraformaldehyde (Electron Microscopy Sciences) and then stained with anti-HER2 Fab protein (5 mg/ml) in 1% (wt/vol) BSA for 1 h followed by extensive washing and incubation with Alexa488-conjugated secondary antibody against a Flag-epitope on the C terminus of the Fab light-chain. The nuclei were stained using the Hoechst dye (Invitrogen) and then mounted with ProLong antifade reagent (Invitrogen). The images were acquired using the WaveFX spinning disk confocal microscope by Quorom Technologies Inc. Acquisition parameters were adjusted to exclude saturation of the pixels. For assessing binding specificity in HER2+ (BT474) and HER2-(T47D) cells, such parameters were kept constant between the two cell lines.

Results and Discussion

Library Screening Against Her2-Transfected Cells and Illumina Sequence Analysis

We subjected the synthetic Fab library F to three rounds of selection on 293T cells transiently transfected to express Her2 (FIG. 1a). To help reduce background from phage binding to undesired cell-surface epitopes and non-specific binding phage clones, the library was incubated with untransfected 293T cells prior to incubation with the Her2 expressing cells. These undesired background phage were removed with the cell pellet and the library phage left in solution were incubated with the Her2 transfected cells. After washing away non-binding phage, the remaining phage, which should include the Her2 specific binders (positive selection pool), were amplified in E. coli. We also carried out three rounds of selection against untransfected 293T cells. This negative selection was carried out with the rational that the sequences obtained from this pool represent undesired background clones that are unlikely to be Her2 specific binders. As such, comparing the sequences from the positive and negative selections should help readily identify sequences in the positive pool that arise from phage clones binding to undesired epitopes.

The positive and negative selection pools, and the naïve library, were next subjected to Illumina sequencing analysis. Of the 100 most frequently observed CDR H3 sequences in the positive pool, which represent anywhere from 0.06 to 14.94% of the total number of sequences obtained, 20 were also present in the negative selection pool (FIG. 5). A similar number of sequences, 20, from the positive selection pool also overlap with the naïve library pool. Sixteen of the sequences observed in the naïve library are also present in the negative selection pool. As expected, sequences in the naïve library exhibited a much greater degree of diversity than the sequences of the two selected pools.

PCR Recovery of Her2 Specific Clones from the Positive Selection Pool

Single clones of interest, identified from the Illumina sequencing results, were isolated from the positive selection output pool using a PCR based recovery method in which phosphorylated primers annealed to unique CDR H3 sequences (FIG. 1b). The primers were designed so that the 5' ends of the forward and reverse primers were abutting, resulting in the amplification of the complete phagemid clone vector. Following a blunt-end ligation and transformation into E. coli, single colonies can be isolated and sequenced to verify recovery of the desired CDR H3. Using this method, we successfully recovered five unique phage clones from the positive selection pool (FIG. 2). The successfully recovered clones vary in their abundance in the positive pool, with the least abundant clone representing only 0.25% of the pool. Of note, five of the PCR reactions we attempted failed to generate a PCR product. This may be due to their low abundance in the output pool used for the PCR template, as each of these five clones represented less than 0.5% of the pool.

Binding Kinetics of Recovered Anti-Her2 Clones

Kinetic analysis of the purified Fabs by SPR shows that the five recovered Fab clones bind to recombinant Her2 with high affinities (Table 3), with $K_D$ values ranging from 4 nM to 75 nM. These data suggest that the cell-surface selection methodology presented here can be used to rapidly recover multiple Fab clones that bind with high affinity to the target of interest. We chose three of the five Fab clones, WY547B, WY574E, and WY574F, for further analysis based on the observation that they exhibit a range of affinities encompassing the highest (WY574F), lowest (WY574E), and an intermediate (WY574B) affinity value.

TABLE 3

Binding Kinetics of anti-Her2 Fab clones

| Fab | $K_a$ ($M^{-1}s^{-1}$) | $K_d$ ($s^{-1}$) | $K_D$ (nM) |
| --- | --- | --- | --- |
| WY574B | $1.0 \times 10^5$ | $1.4 \times 10^{-3}$ | 14 |
| WY574E | $1.9 \times 10^5$ | $6.8 \times 10^{-4}$ | 4 |
| WY574F | $9.7 \times 10^3$ | $7.3 \times 10^{-4}$ | 75 |
| WY677C | $4.37 \times 10^4$ | $1.62 \times 10^{-3}$ | 37 |
| WY677D | $4.01 \times 10^5$ | $1.08 \times 10^{-2}$ | 27 |

Cell-Surface Specificity of Anti-Her2 Fabs

Next, the specificity of Fab clones WY574B, WY574E, and WY574E, was examined by flow-cytometry using 293T cells transiently transfected with Her2 or EGFR, which is also a member of the EGFR receptor family. A fluorescence shift was observed in the Her2-transfected cell population for all three Fab clones (FIG. 3a). A similar shift in fluorescence staining was not observed in the EGFR-transfected cell population or the unstained Her2-transfected 293T cell population. This data suggests that the recovered Fabs are binding specifically to the Her2 transfected cell population. We also evaluated the specificity of the Fab clones by flow-cytometric analysis with the Her2 positive breast cancer cell-line BT474 and the Her2 negative breast cancer cell-line T47D (FIG. 3b). As expected, a drastic shift in the fluorescence signal of the BT474 cell population was observed in the presence of the anti-Her2 Fabs. In contrast, little or no binding of the three Fabs was detected in the Her2 negative T47D cell population.

Figure 4A:
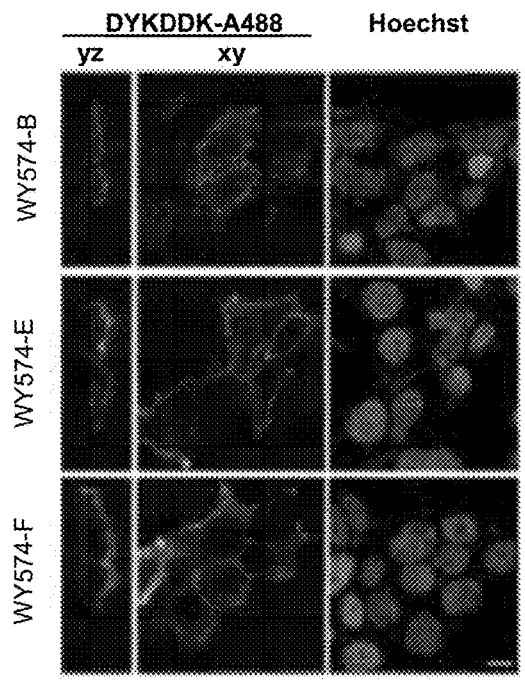
FIGS. 4A and 4B show the binding specificity of synthetic anti-HER2 antibodies against live cells.
Figure 4B:
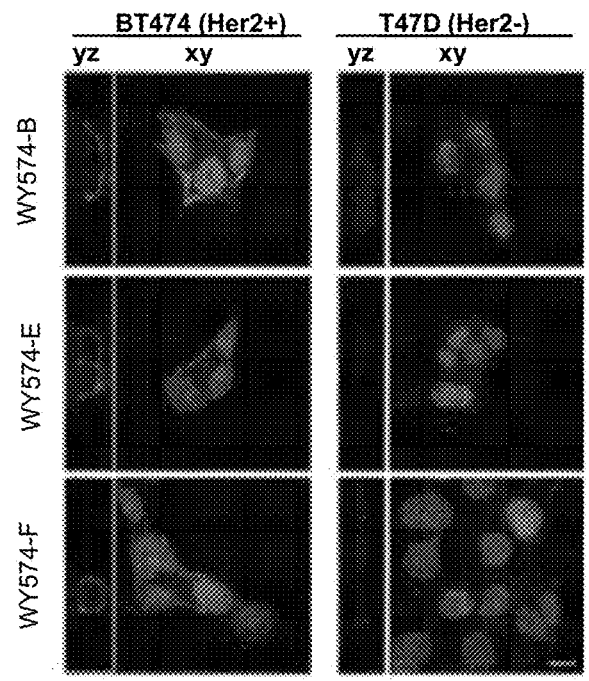

Finally, we sought to confirm the specificity of the three Fabs for Her2 presented on the cell-surface by immunofluorescent staining (IF) of Her2-transfected 293T cells and a Her2 expressing cancer cell-line. Fluorescent staining of each Fab clone was observed around the cell periphery in the Her2-transfected 293T cells (FIG. 4a). Consistent with staining pattern observed in the Her2-transfected cells, fluorescent staining of the Her2 positive BT474 cancer-cell line was also evident by IF (FIG. 4b). In contrast, no specific staining was observed for the Her2-negative T47D cancer cell-line. Collectively, these data strongly demonstrate that the recovered Fab clones bind specifically to Her2 presented in the context of the cell-surface.

Selection of phage-displayed antibody libraries against cell-surface antigens is often challenging, as the vast array of epitopes presented on the cell-surface gives rise to a high degree of background binding and poor enrichment of clones specific to the target of interest. A unique aspect of the methodology described here is the use of deep sequencing to identify phage clones specific to the cell-surface antigen of interest. Here, sequences distinctive/exclusive to the positive selection output pool represent clones that have a high probability of being specific for the target antigen. In addition, combining cell-surface selections with deep sequencing allows rare clones to be identified. It is unlikely that the degree of clonal diversity we observe by deep sequencing could be resolved using traditional phage display methodologies, in part because of the practical limitations of manually screening sufficient numbers of single phage clones to retrieve a similar level of sequence diversity. Although a variety of factors can influence clonal diversity during the selection process, such as the growth advantage of certain clones, selection methodologies also tend to preferentially enrich for higher affinity binders. As a consequence, the diversity of the sequences recovered in later rounds may be diminished. However, high throughput DNA sequencing is becoming an increasingly accessible technology, as evidenced by recent reports that made use of deep sequencing approaches to characterize human antibody libraries and V-gene repertoires of immunized mice [25, 26].

We reasoned that Her2 would be an ideal model given the existence of a well-characterized therapeutic monoclonal antibody specific for Her2, which is reflective of our goal of applying the CellectSeq methodology to isolating stable, high affinity, antibody fragments specific to therapeutically relevant cell-surface proteins. Trastuzumab (Genentech, also known as Herceptin) is a humanized IgG1 specific for the extracellular domain of Her2 [22], which is approved for clinical treatment of Her2 positive breast cancer. Although Trastuzumab represents a very successful therapeutic option for patients, not all Her2 positive cancers are responsive to Trastuzumab treatment [23]. In addition, resistance to Trastuzumab may also develop during the course of treatment [20, 24]. The synthetic antibody fragments we have identified using the CellectSeq method exhibit binding characteristics that are highly desirable for potential new therapeutic antibody candidates. Specifically, the synthetic antibody fragments we have isolated bind with both high affinity and specificity to Her2.

The five synthetic antibody fragments rescued from our positive selection pool exhibit specific binding to Her2, both by SPR analysis to recombinant Her2 and by flow-cytometry and IF to cell-surface Her2. However, it is also important to note that the methodology we report here may allow for the identification of antibody fragments specific for proteins that are over-expressed as a consequence of the over-expression of Her2 itself.

Of the ten unique CDR H3 clones we attempted to rescue, five failed to generate a PCR product. This may be due to factors that include the sequence and length of the CDR H3, the abundance of the template in the positive selection pool, or the design of the PCR primers. It is important to consider, however, that these factors were not optimized in this study. In light of this observation, the number of phagemid clones we successfully rescued is considerably high. Another important consideration is whether the methodology presented here introduces bias into the final sequence analysis. For example, many of the sequences in the naïve and negative selection pools that overlap with the positive selection pool are of very short length. However, this type of potential bias can be identified by comparing the abundance of given sequences in the positive pool to the negative pool. It is possible that shorter sequences were preferentially amplified during the PCR reaction used to recover the DNA that was subsequently submitted for Illumina sequencing. In addition, a previous analysis of the naïve Fab library did demonstrate that there was a bias towards shorter CDR H3 loop lengths, which was likely attributable to differences in the efficiency of the library mutagenesis reaction with oligos of different lengths. This issue may be addressed by comparison of the length distribution of the hypervariable regions sequenced by traditional Sanger methods to those sequenced in the deep sequencing analysis.

A limiting step to molecular display technologies is the need for correctly folded, purified antigen. For example, multi-domain membrane represent more than 70% of current drug targets due to their role in the progression and tumorigenesis of numerous cancers [1], yet the properties of these proteins makes their production and purification extremely difficult. The instability of membrane proteins also makes them challenging targets to work with during in vitro library selections, as many of these proteins depend on the membrane environment for their correct structure and function. The methodology reported here bypasses the need for purified antigen and allows library selection directly to cell-surface targets. Consequently, the CellectSeq methodology increases the likelihood that the selected antibodies will recognize epitopes on the native, functionally relevant structure of the target antigen. The ability to select for specifically binding phage clones without the need for purified antigen will significantly expand the range of antigens that can be targeted using phage display technology.

The described methods could also be tailored to the specific needs of the antigen of interest. For instance, the CellectSeq approach can be combined with protocols that involve screening libraries against cells in the presence of ligands, with the goal of targeting active forms of receptors [6]. In cases in which the target of interest may be a member of an oligomeric complex, the selection can be performed using cells co-transfected to express all of the relevant complex members, with the intention of isolating antibodies specific to the multimerized protein. One example of relevance here is Her2, as it known to homo- and heterodimerize with the other members of the EGFR family [27].

Example 2. PCR-Based Recovery of Antibody Fragments to Additional Cell-Surface Targets The rescue strategies described herein make use of both the unique H3 and L3 CDR sequences.

Figure 6A:
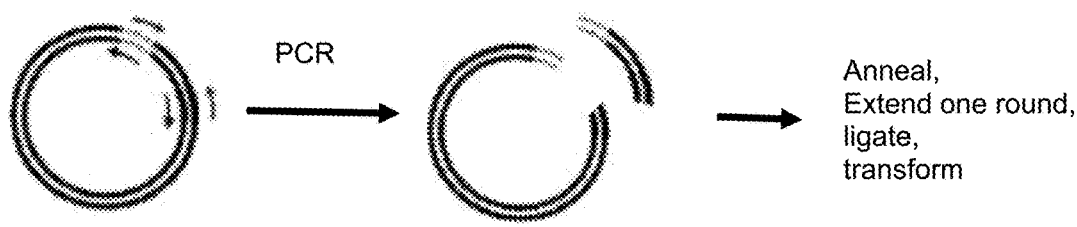
FIGS. 6A and 6B show rescue strategies that utilize both the unique heavy chain CDR3 (CDRH3) sequence and light chain CDR3 (CDRL3) sequences identified using the methods provided herein.
Figure 6B:
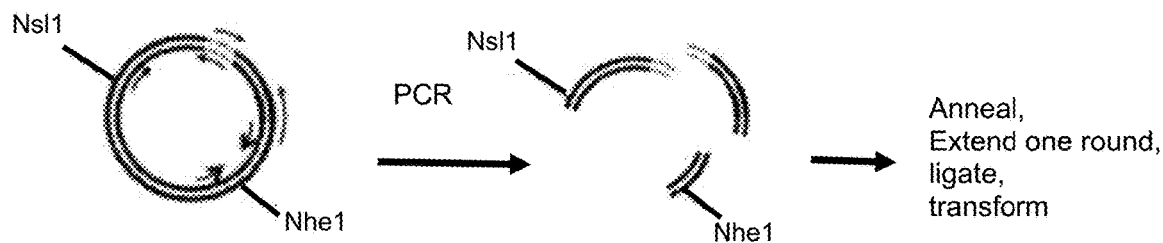

As an alternative to identifying positive Fabs by clonal cell ELISAs, two different PCR based recovery methods are used (FIGS. 6A, 6B). As depicted in FIG. 6A, two primer sets specific for both CDR H3 and L3 are used to make the recovery more specific. Primers are designed to anneal to the L3 and H3, and amplify two fragments, in both directions. This results in two fragments that both contain the L3 and H3 regions. The two fragments can be annealed, and then a single round of DNA extension is done. The resulting product can then be ligated and transformed into E. coli to recover the desired phage clone in the original library display vector. As depicted in FIG. 6B, three primer sets are used to amplify three fragments, in a strategy that makes use of both the H3 and L3 unique sequences and unique Nsi1 and Nhe1 sites in the library phage vector. The three fragments are annealed, extended by PCR, and subcloned into an IPTG inducible protein expression vector with compatible Nsi1 and Nhe1 restriction enzyme sites. The rescued Fab can be expressed directly from the resulting vector.

The phage-Fab clones that were rescued from the positive selection pool are shown in FIG. 9. Listed are the phage-Fab clones targeting various cell surface receptors that were successfully rescued from the positive selection pool. The following is displayed: the cell line used to express the antigen of interest; the phage-display library used for selection (F: Fab, G:scFv); the rescue strategy used to recover the clones (1. Clonal ELISA, 2. cdrH3 PCR, 3. cdrL3:cdrH3 PCR); the rank of the sequence in the round four positive selection pool based on raw counts which reflects the number of times the sequence was observed in the pool; the CDR L3 and H3 sequences obtained from the round four positive selection output; the raw counts and percentage those counts represent of the entire output pool for the round four and round three positive and negative pools; whether the rescued clones have been validated for cell binding. The conditions used for positive and negative selections are also annotated. Note that GUP is a cocktail of Glucosamine, Uridine and PugNAc.

Figure 7:
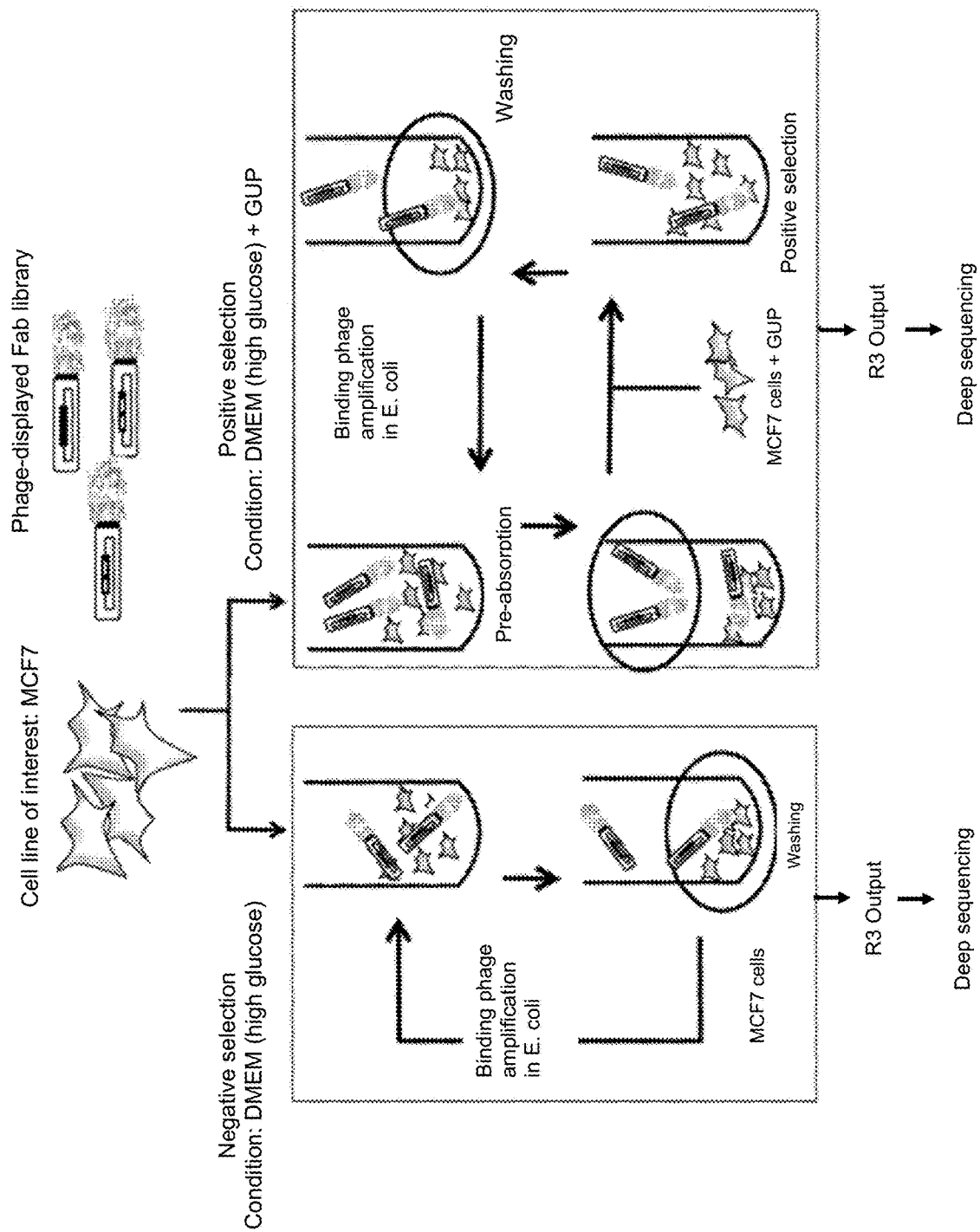
FIG. 7 is a flow chart of the selection strategy used to isolate Fab clones specific for cell surface O-GlcNAc-dependent epitopes.

Example 3. Rapid Isolation of Antibody Fragments Specific to Cell Growth Conditions FIG. 7 depicts a flow chart of the selection strategy used to isolate Fab clones specific for cell surface O-GlcNAc-dependent epitopes, demonstrating that the CellectSeq method can be used to isolate Fabs specific to cell growth conditions. The positive selection begins a pre-absorption step in which the library phage are incubated with MCF7 breast cancer cells grown in DMEM (Dulbecco's Modified Eagle Medium) (high glucose version) supplemented with 10% FBS. After incubation, the mixture is pelleted to remove the library clones bound to the cells. These clones are likely specific for cell-surface epitopes that are not of interest, or are non-specific binding clones. The library phage remaining in the supernatant are incubated with the MCF7 cells grown in DMEM (high glucose version) supplemented with 10% FBS plus 30 mM Glucosamine (G), 5 mM Uridine (U) and 50 µM PugNAc (P) (collectively referred to as GUP), non-binding phage are then washed away, and the phage bound to the GUP treated MCF7 cells are amplified in an E. coli host. The amplified phage are then purified and used in the next round of selection. In parallel, the negative selection is carried out by incubating library phage with MCF7 cells that have been grown in the absence of GUP treatment. Phage clones that do not bind to the cells are washed away, and the remaining bound phage are amplified in an E. coli host for the next round of selection. O-GlcNAc enrichment is achieved by adding GUP (a cocktail of Glucosamine, Uridine and PugNAc).

Figure 8:
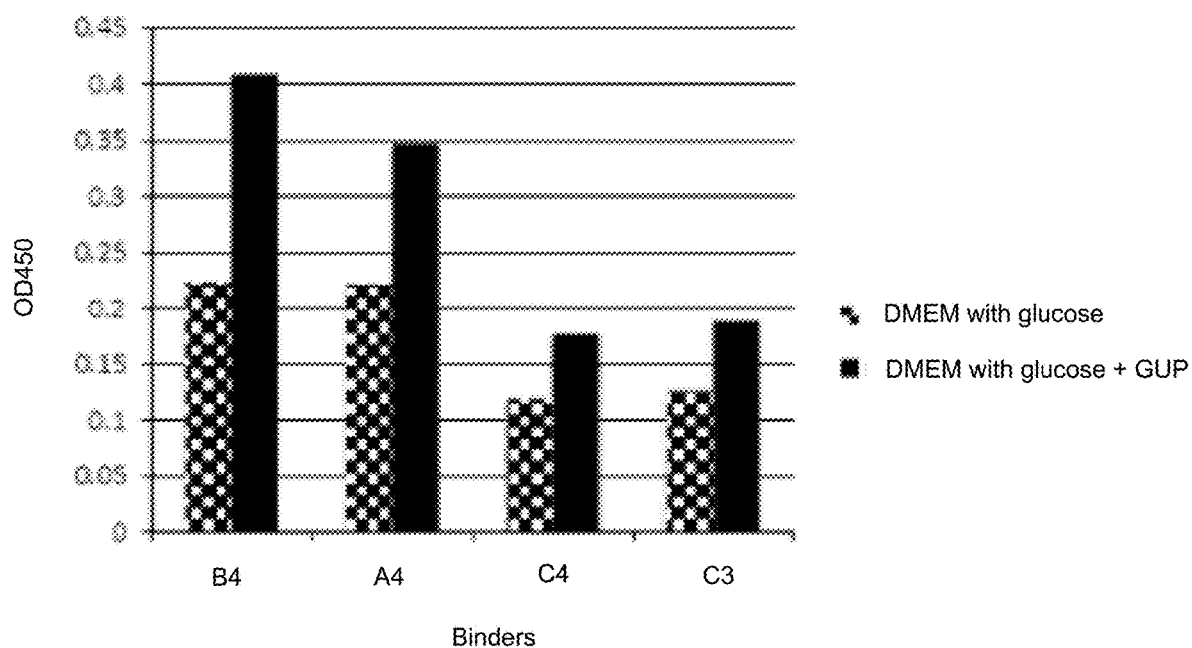
FIG. 8 is an ELISA graph of binders identified from the selection strategy used to identify Fab clones specific for cell surface O-GlcNAc-dependent epitopes.

FIG. 8 depicts an ELISA graph of binders chosen from R40 from the selection strategy used to isolated Fabs specific for surface O-GlcNAc-dependent epitopes. B4 binder ranked #1 with ratio of 1.8, A4 binder ranked #2 with ratio of 1.6, C4 binder ranked #4 with ratio of 1.5 and C3 binder ranked #7 with ratio 1.5.

Example 4. Deep Sequencing to Decode Variable Regions of Affinity Reagents

FIG. 10 provides diagrams for some deep/high-throughput sequencing strategies used to decode variable regions of affinity reagents in a positive or negative selection pool. In the examples shown here, one or more complementarity determining regions (CDRs) of synthetic antibodies are decoded by deep sequencing.

Materials and Methods

Positive and negative selection pool phages from rounds three and four were infected into XL1Blue cells and grown overnight in 2YT supplemented with 100 ug/ml carbenicillin. Cultures were miniprepped to obtain phagemid DNA and normalized to 25 ng/ul to use as templates for PCR. PCR primers added barcodes and platform-specific adapters, while amplifying one or more variable regions of the affinity reagent by annealing to adjacent regions of the affinity reagent framework.

Strategy 1: Illumina Sequencing of CDRs L3 and H3

The forward PCR primer was composed of a paired-end compatible Illumina adaptor sequence (5'AATGATACGGC-GACCACCGAGATCT-3') (SEQ ID NO: 223) and an annealing site upstream of CDR-L3 (5' GCAGCCG-GAAGACTTCGCAACTTATTACTGTCAGC-3') (SEQ ID NO: 224). The reverse PCR primer was composed of a paired-end compatible Illumina adaptor sequence (5' CAAGCAGAAGACGGCATACGAGAT-3') (SEQ ID NO: 225), a five base barcode (5'NNNNN-3') (SEQ ID NO: 226), and an annealing site downstream of CDR-H3 (5'GGTGAC-CAGGGTTCCTTGACCCCAGTAGTC-3') (SEQ ID NO: 227).

PCR reactions were performed with the high fidelity polymerase ExTaq (TaKaRa) and 400 ng of template phagemid DNA. Reactions were subjected to one denaturation step for 30 sec at 95° C., followed by 14 cycles of 30 sec at 94° C. and 60 sec at 72° C., with a final extension for 5 min at 72° C. PCR products were cleaned enzymatically with ExoI to remove residual primers, SAP to dephosphorylate dNTPs and Dpn1 to digest methylated phagemid template DNA. PCR products were quantitated using dsDNA-specific fluorescent dye (PicoGreen), normalized, pooled and purified by gel extraction of the correct fragment size (1007 bp).

The purified DNA fragments were subjected to Illumina DNA sequencing on GAIIx or HiSeq platforms, using custom read primers and read lengths: Read 1 forward (L3) primer (5' CAGCCGGAAGACTTCGCAACTTATTACT-GTCAGCAA-3') (SEQ ID NO: 228) for a minimum of 30 bases; Read 2 forward (barcode) primer (5' GAC-TACTGGGGTCAAGGAACCCTGGTCACC-3') (SEQ ID NO: 229) for a minimum of 5 bases; Read 3 reverse (H3) (5' GGTGACCAGGGTTCCTTGACCCCAGTAGTC-3') (SEQ ID NO: 230) for a minimum of 65 bases. Each sequencing read was assigned to its correct pool of the basis of its unique barcode sequence. The reads were filtered according to their Phred score [31]. Briefly, all sequences with phred scores of 20 or higher for every base were kept. DNA sequences were translated to decode the sequences of CDRs L3 and H3.

Strategy 2: Illumina Sequencing of CDRs L3 and H3, with Optional Sequencing of H2 and H1

The forward PCR primer was composed of a paired end Read 1 Illumina adaptor sequence (5'AATGATACGGC-GACCACCGAGATCTACACTCTTTCCCTACAC-GACGCTCTTCCGATCT-3) (SEQ ID NO: 231), barcode (5'NNNNNNNN-3') (SEQ ID NO: 232) and an annealing site downstream of CDR-H3 (5'GGTGACCAGGGTTCCT-TGACCCCAGTAGTC-3') (SEQ ID NO: 233). The reverse PCR primer was composed of a paired end Read 2 Illumina adaptor sequence (5' CGGTCTCGGCATTCCTGCTGAAC-CGCTCTTCCGATCT-3') (SEQ ID NO: 234), optional barcode (5'NNNNNN-3'), and an annealing site upstream of CDR-L3 (5' CAGCCGGAAGACTTCGCAACTTATTACT-GTCAGCAA-3') (SEQ ID NO: 235). PCR reactions were carried out using ExTaq, as described for Strategy 1.

The purified DNA fragments were subjected to Illumina DNA sequencing on GAIIx, HiSeq or Miseq platforms, using standard paired end read primers and 2×150 bp read lengths or longer, to span CDR-H2 and CDR-H1 in addition to barcode and CDR-H3 (read 1) or CDR-L3 (read 2).

Strategy 3: IonTorrent Sequencing of CDR H3

The forward PCR primer was composed of an IonTorrent Adapter A sequence (5' CCATCTCATCCCTGCGTGTCTC-CGACTCAG-3') (SEQ ID NO: 236), barcode (5' NNNNNNNNNC-3') (SEQ ID NO: 236) and an annealing site upstream of CDR-H3 (5'AGGACACTGCCGTCTAT-TAT-3') (SEQ ID NO: 237). The reverse PCR primer was composed of IonTorrent adapter P1 sequence (5' CCTCTC-TATGGGCAGTCGGTGAT-3') (SEQ ID NO: 238) and an annealing site downstream of CDR-H3 (5'AGGACACTGC-CGTCTATTAT-3') (SEQ ID NO: 239). PCR reactions were carried out using Phusion with one denaturation step at 98 C for 5 min, followed by 14 cycles of 5 sec at 98° C., 10 sec at 54° C., 15 sec at 72vC, with a final extension for 10 min at 72° C. Residual primers and dNTPs were removed using column (Qiagen), and PCR products were quantitated, normalized and pooled, for single end sequencing on an Ion-Torrent platform.

Although preferred embodiments of the invention have been described herein, it will be understood by those skilled in the art that variations may be made thereto without departing from the spirit of the invention or the scope of the appended claims. All references cited herein, including those in the attached reference list, are incorporated by reference.

REFERENCE LIST

1. Lundstrom K (2007) Structural genomics and drug discovery. J Cell Mol Med 11: 224-238.
2. Overington J P, Al-Lazikani B, Hopkins A L (2006) How many drug targets are there? Nat Rev Drug Discov 5: 993-996.
3. Adams G P, Weiner L M (2005) Monoclonal antibody therapy of cancer. Nat Biotechnol 23: 1147-1157.
4. Weiner L M, Surana R, Wang S (2010) Monoclonal antibodies: versatile platforms for cancer immunotherapy. Nat Rev Immunol 10: 317-327.
5. Burton D R (2002) Antibodies, viruses and vaccines. Nat Rev Immunol 2: 706-713.
6. Eisenhardt S U, Schwarz M, Bassler N, Peter K (2007) Subtractive single-chain antibody (scFv) phage-display: tailoring phage-display for high specificity against function-specific conformations of cell membrane molecules. Nat Protoc 2: 3063-3073.
7. Huie M A, Cheung M C, Muench M O, Becerril B, Kan Y W, et al. (2001) Antibodies to human fetal erythroid cells from a nonimmune phage antibody library. Proc Natl Acad Sci USA 98: 2682-2687.
8. Noronha E J, Wang X, Desai S A, Kageshita T, Ferrone S (1998) Limited diversity of human scFv fragments isolated by panning a synthetic phage-display scFv library with cultured human melanoma cells. J Immunol 161: 2968-2976.
9. Ridgway J B, Ng E, Kern J A, Lee J, Brush J, et al. (1999) Identification of a human anti-CD55 single-chain Fv by subtractive panning of a phage library using tumor and nontumor cell lines. Cancer Res 59: 2718-2723.
10. Van Ewijk W, de Kruif J, Germeraad W T, Berendes P, Ropke C, et al. (1997) Subtractive isolation of phage-displayed single-chain antibodies to thymic stromal cells by using intact thymic fragments. Proc Natl Acad Sci USA 94: 3903-3908.
11. Giordano R J, Cardo-Vila M, Landenranta J, Pasqualini R, Arap W (2001) Biopanning and rapid analysis of selective interactive ligands. Nat Med 7: 1249-1253.
12. Williams B R, Sharon J (2002) Polyclonal anti-colorectal cancer Fab phage display library selected in one round using density gradient centrifugation to separate antigen-bound and free phage. Immunol Lett 81: 141-148.
13. Osbourn J K, Derbyshire E J, Vaughan T J, Field A W, Johnson K S (1998) Pathfinder selection: in situ isolation of novel antibodies. Immunotechnology 3: 293-302.
14. Osbourn J K, Earnshaw J C, Johnson K S, Parmentier M, Timmermans V, et al. (1998) Directed selection of MIP-1 alpha neutralizing CCR5 antibodies from a phage display human antibody library. Nat Biotechnol 16: 778-781.
15. Sidhu S S, Fellouse F A (2006) Synthetic therapeutic antibodies. Nature Chem Biol 2: 682-688.
16. Yarden Y, Sliwkowski M X (2001) Untangling the ErbB signalling network. Nat Rev Mol Cell Biol 2: 127-137.
17. Zhou B P, Hung M C (2003) Dysregulation of cellular signaling by HER2/neu in breast cancer. Semin Oncol 30: 38-48.
18. Slamon D J, Clark G M, Wong S G, Levin W J, Ullrich A, et al. (1987) Human breast cancer: correlation of relapse and survival with amplification of the HER-2/neu oncogene. Science 235: 177-182.
19. Slamon D J, Godolphin W, Jones L A, Holt J A, Wong S G, et al. (1989) Studies of the HER-2/neu proto-oncogene in human breast and ovarian cancer. Science 244: 707-712.
20. Nahta R, Esteva F J (2003) HER-2-targeted therapy: lessons learned and future directions. Clin Cancer Res 9: 5078-5084.

21. Ross J S, Fletcher J A (1998) The HER-2/neu Oncogene in Breast Cancer: Prognostic Factor, Predictive Factor, and Target for Therapy. Oncologist 3: 237-252.
22. Carter P, Presta L, Gorman C M, Ridgway J B, Henner D, et al. (1992) Humanization of an anti-p185HER2 antibody for human cancer therapy. Proc Natl Acad Sci USA 89: 4285-4289.
23. Vogel C L, Cobleigh M A, Tripathy D, Gutheil J C, Harris L N, et al. (2002) Efficacy and safety of trastuzumab as a single agent in first-line treatment of HER2-overexpressing metastatic breast cancer. J Clin Oncol 20: 719-726.
24. Berns K, Horlings H M, Hennessy B T, Madiredjo M, Hijmans E M, et al. (2007) A functional genetic approach identifies the PI3K pathway as a major determinant of trastuzumab resistance in breast cancer. Cancer Cell 12: 395-402.
25. Ge X, Mazor Y, Hunicke-Smith S P, Ellington A D, Georgiou G Rapid construction and characterization of synthetic antibody libraries without DNA amplification. Biotechnol Bioeng 106: 347-357.
26. Reddy S T, Ge X, Miklos A E, Hughes R A, Kang S H, et al. Monoclonal antibodies isolated without screening by analyzing the variable-gene repertoire of plasma cells. Nat Biotechnol 28: 965-969.
27. Rubin I, Yarden Y (2001) The basic biology of HER2. Ann Oncol 12 Suppl 1: S3-8.
28. Fellouse F A, Pal G (2005) Methods for the Construction of Phage-Displayed Libraries. In: Sidhu S S, editor. Phage Display in Biotechnology and Drug Discovery. Boca Raton: CRC Press.
29. Fellouse F A, Esaki K, Birtalan S, Raptis D, Cancasci V J, et al. (2007) High-throughput generation of synthetic antibodies from highly functional minimalist phage-displayed libraries. J Mol Biol 373: 924-940.
30. Tonikian R, Zhang Y, Boone C, Sidhu S S (2007) Identifying specificity profiles for peptide recognition modules from phage-displayed peptide libraries. Nat Protoc 2: 1368-1386.
31. Cock P J, Fields C J, Goto N, Heuer M L, Rice P M The Sanger FASTQ file format for sequences with quality scores, and the Solexa/Illumina FASTQ variants. Nucleic Acids Res 38: 1767-1771.
32. Greulich H, Chen T H, Feng W, Janne P A, Alvarez J V, et al. (2005) Oncogenic transformation by inhibitor-sensitive and -resistant EGFR mutants. PLoS Med 2: e313.
33. Li Y M, Pan Y, Wei Y, Cheng X, Zhou B P, et al. (2004) Upregulation of CXCR4 is essential for HER2-mediated tumor metastasis. Cancer Cell 6: 459-469.
34. Sancak Y, Peterson T R, Shaul Y D, Lindquist R A, Thoreen C C, et al. (2008) The Rag GTPases bind raptor and mediate amino acid signaling to mTORC1. Science 320: 1496-1501.

What is claimed is:

1. A method of identifying a potential binder to a cell surface antigen, the method comprising:
   (a) providing a display library comprising clones, each of which displaying an antibody or antibody fragment, wherein the antibody or antibody fragment has an antibody variable region comprising:
   CDR L1 comprising an amino acid sequence identified as SEQ ID NO: 240;
   CDR L2 comprising an amino acid sequence identified as SEQ ID NO: 241;
   CDR-L3 comprising an amino acid sequence identified as SEQ ID NO: 262;
   CDR H1 comprising an amino acid sequence identified as SEQ ID NO: 263;
   CDR H2 comprising an amino acid sequence identified as SEQ ID NO: 264; and
   CDR-H3 comprising an amino acid sequence identified as SEQ ID NO: 265;
   wherein each of the clones comprises DNA encoding the antibody variable region displayed thereby;

(b) screening the library against a population of cells that express the cell surface antigen to produce a positive selection pool of library clones and against a population of cells for producing a negative selection pool of library clones;

(c) sequencing DNAs encoding antibody variable regions of the positive selection pool and of the negative selection pool; and (d) identifying, among the sequenced DNAs, DNA encoding an antibody variable region that is more abundant in the positive selection pool than in the negative selection pool, thereby identifying an antibody variable region that is more abundant in the positive selection pool than in the negative selection pool, thereby identifying a potential binder to the cell surface antigen.

2. The method of claim 1, further comprising a step of producing a purified antibody or antibody fragment, wherein the purified antibody or antibody fragment comprises the antibody variable region encoded by the DNA identified to be more abundant in the positive selection pool than in the negative selection pool.

3. The method of claim 1, wherein the display library is a phage-display library and the clones are phage clones.

4. The method of claim 1, wherein the antibody or antibody fragment is a Fab.

5. The method of claim 1, wherein the cell surface antigen is a protein, wherein the cells that express the cell surface antigen are cells of a cell line which are transfected to express the cell surface antigen, and wherein the cells for producing the negative selection pool are cells of the cell line which are not transfected to express the cell surface antigen.

6. The method of claim 1, wherein the sequencing is done by deep sequencing.

7. The method of claim 1, wherein step (b) comprises multiple rounds of screening the library against the population of cells that express the cell surface antigen and against the population of cells for producing a negative selection pool of library clones.

8. The method of claim 1, wherein step (d) comprises identifying DNA encoding an antibody variable region that is more abundant in the positive selection pool than in the negative selection pool by a factor selected from the group consisting of a factor of at least 2, a factor of at least 3, a factor of at least 4 and a factor of at least 5.

9. The method of claim 1, wherein the cell surface antigen is selected from the group consisting of HER2, CD133, ErbB3, Fzd7, RORI, ROR2, exon16 deleted ErbB2, ITGA11 and O-GlcNAc.

10. A method of identifying a binder to a cell surface antigen, the method comprising:

(a) providing a display library comprising clones, each of which displaying an antibody or antibody fragment, wherein the antibody or antibody fragment has an antibody variable region comprising:

CDR L1 comprising an amino acid sequence identified as SEQ ID NO: 240;

CDR L2 comprising an amino acid sequence identified as SEQ ID NO: 241;

CDR-L3 comprising an amino acid sequence identified as SEQ ID NO: 262;

CDR H1 comprising an amino acid sequence identified as SEQ ID NO: 263;

CDR H2 comprising an amino acid sequence identified as SEQ ID NO: 264; and

CDR-H3 comprising an amino acid sequence identified as SEQ ID NO: 265;

wherein each of the clones comprises DNA encoding the antibody variable region displayed thereby;

(b) screening the library against a population of cells that express the cell surface antigen to produce a positive selection pool of library clones and against a population of cells for producing a negative selection pool of library clones;

(c) sequencing DNAs encoding antibody variable regions of the positive selection pool and of the negative selection pool;

(d) identifying, among the sequenced DNAs, DNA encoding an antibody variable region that is more abundant in the positive selection pool than in the negative selection pool; and (e) producing a purified antibody or antibody fragment, wherein the purified antibody or antibody fragment comprises the antibody variable region encoded by the DNA identified to be more abundant in the positive selection pool than in the negative selection pool, and confirming that the purified antibody or antibody fragment binds to the cell surface antigen in purified form and/or binds to cells expressing the cell surface antigen, thereby identifying a binder to the cell surface antigen.

11. The method of claim 10, wherein the display library is a phage-display library and the clones are phage clones.

12. The method of claim 10, wherein the antibody or antibody fragment is a Fab.

13. The method of claim 10, wherein the cell surface antigen is a protein, wherein the cells that express the cell surface antigen are cells of a cell line which are transfected to express the cell surface antigen, and wherein the cells for producing the negative selection pool are cells of the cell line which are not transfected to express the cell surface antigen.

14. The method of claim 10, wherein the sequencing is done by deep sequencing.

15. The method of claim 10, wherein step (b) comprises multiple rounds of screening the library against the population of cells that express the cell surface antigen and against the population of cells for producing a negative selection pool of library clones.

16. The method of claim 10, wherein step (d) comprises identifying DNA encoding an antibody variable region that is more abundant in the positive selection pool than in the negative selection pool by a factor selected from the group consisting of a factor of at least 2, a factor of at least 3, a factor of at least 4 and a factor of at least 5.

17. The method of claim 10, wherein the cell surface antigen is selected from the group consisting of HER2, CD133, ErbB3, Fzd7, RORI, ROR2, exon16 deleted ErbB2, ITGA11 and O-GlcNAc.

18. The method of claim 1, wherein the CDR-L3 comprises an isoleucine residue flanking the C-terminal amino acid residue thereof.

19. The method of claim 10, wherein the CDR-L3 comprises an isoleucine residue flanking the C-terminal amino acid residue thereof.

* * * * *